United States Patent
Burren et al.

(10) Patent No.: US 12,208,236 B2
(45) Date of Patent: Jan. 28, 2025

(54) INJECTION OR INFUSION DEVICE COMPRISING AN IMPROVED HOUSING AND RELEASE LINER FOR REMOVING STERILE BARRIER FILMS USING THE RELEASE LINER

(71) Applicant: Ypsomed AG, Burgdorf (CH)

(72) Inventors: Stefan Burren, Schwarzenburg (CH);
Mario Bernhard, Burgdorf (CH);
Susanne Schenker, Aarwangen (CH);
Andres Mellenberger, Koppigen (CH);
Christian Schrul, Burgdorf (CH);
Markus Tschirren, Burgdorf (CH)

(73) Assignee: Ypsomed AG, Burgdorf (CH)

( * ) Notice: Subject to any disclaimer, the term of this patent is extended or adjusted under 35 U.S.C. 154(b) by 1176 days.

(21) Appl. No.: 17/016,933

(22) Filed: Sep. 10, 2020

(65) Prior Publication Data
US 2020/0405951 A1 Dec. 31, 2020

Related U.S. Application Data

(63) Continuation of application No. PCT/IB2019/051359, filed on Feb. 20, 2019.

(30) Foreign Application Priority Data

Mar. 15, 2018 (EP) ..................................... 18161873
Mar. 27, 2018 (EP) ..................................... 18164145
Nov. 22, 2018 (EP) ..................................... 18207849

(51) Int. Cl.
*A61M 5/142* (2006.01)
*A61M 5/162* (2006.01)
*A61M 5/28* (2006.01)

(52) U.S. Cl.
CPC ........ *A61M 5/14248* (2013.01); *A61M 5/162* (2013.01); *A61M 5/285* (2013.01); *A61M 2005/14252* (2013.01)

(58) Field of Classification Search
CPC ...... A61M 2205/13; A61M 2039/0686; A61M 2005/247; A61M 2005/2492;
(Continued)

(56) References Cited

U.S. PATENT DOCUMENTS 3,260,147 A * 7/1966 Farabee ............... B26D 1/0006
                                                   112/129
3,260,149 A * 7/1966 Deaver ................... F16B 35/00
                                                    40/200
(Continued)

FOREIGN PATENT DOCUMENTS

EP 2512552 B1 2/2015
EP 3260147 A1 12/2017
(Continued)

OTHER PUBLICATIONS

Extended European Search Report received for European patent application No. 18164145.7, issued on Nov. 12, 2018, 6 page.
(Continued)

*Primary Examiner* — Jason E Flick
*Assistant Examiner* — Adam J. Cermak
(74) *Attorney, Agent, or Firm* — Dorsey & Whitney LLP

(57) ABSTRACT

An injection device configured for attachment to the skin of a patient includes a housing and a skin adhesive layer attached to an external surface of the housing for attaching the injection device to the skin of a patient. A release liner covering the skin adhesive layer prevents the injection device from attaching to the skin. A film with one end connected to a surface inside of the housing forms a removable sterile barrier and the other end connected to an external
(Continued)

surface of the release liner without contacting the skin adhesive layer. The housing, skin adhesive layer and release liner each include a notch defining a passage for the film so that the second end of the film can extend from the interior to the exterior of the housing.

19 Claims, 25 Drawing Sheets

(58) Field of Classification Search
CPC ...... A61M 2025/0035; A61M 5/14248; A61M 5/2466; A61M 5/285; A61M 5/2455; A61J 1/1406; A61J 1/2024
See application file for complete search history.

(56) References Cited

U.S. PATENT DOCUMENTS

| | | | | |
|---|---|---|---|---|
| 3,260,151 | A * | 7/1966 | Jones | B25B 31/005 269/48.3 |
| 3,909,910 | A * | 10/1975 | Rowe | F16L 29/00 D24/129 |
| 4,019,512 | A * | 4/1977 | Tenczar | A61M 39/14 604/905 |
| 5,019,047 | A * | 5/1991 | Kriesel | A61M 5/152 604/890.1 |
| 6,382,442 | B1 * | 5/2002 | Thibault | A61J 1/1406 215/325 |
| 6,679,529 | B2 | 1/2004 | Johnson et al. | |
| 6,843,782 | B2 * | 1/2005 | Gross | A61M 5/50 604/110 |
| 8,315,687 | B2 * | 11/2012 | Cross | A61B 5/282 600/509 |
| 9,248,232 | B2 * | 2/2016 | Yodfat | A61B 5/14532 |
| 9,427,529 | B2 * | 8/2016 | Cabiri | A61M 5/14248 |
| 10,758,721 | B2 * | 9/2020 | Sonderegger | A61M 5/158 |
| 2001/0056262 | A1 * | 12/2001 | Cabiri | A61M 5/14248 604/180 |
| 2003/0030272 | A1 * | 2/2003 | Johnson | F16L 29/00 285/70 |
| 2004/0116866 | A1 * | 6/2004 | Gorman | A61M 37/00 604/93.01 |
| 2008/0048436 | A1 | 2/2008 | Matkovich et al. | |
| 2009/0095290 | A1 | 4/2009 | Cain et al. | |
| 2011/0166512 | A1 | 7/2011 | Both et al. | |
| 2012/0316506 | A1 * | 12/2012 | Sonderegger | A61M 5/1626 604/180 |
| 2014/0008366 | A1 | 1/2014 | Genosar | |
| 2015/0105691 | A1 * | 4/2015 | Hadvary | A61B 17/3403 604/110 |
| 2015/0217058 | A1 | 8/2015 | Hooven et al. | |
| 2015/0320990 | A1 * | 11/2015 | Burton | A61M 5/1454 604/173 |
| 2016/0089056 | A1 | 3/2016 | Limaye et al. | |
| 2016/0199568 | A1 | 7/2016 | Mcnall et al. | |
| 2016/0220798 | A1 * | 8/2016 | Netzel | A61M 5/14244 |
| 2016/0256665 | A1 | 9/2016 | Doshi et al. | |
| 2016/0310663 | A1 * | 10/2016 | Dantsker | A61M 5/31571 |
| 2016/0310665 | A1 * | 10/2016 | Hwang | C09J 7/21 |
| 2017/0020423 | A1 * | 1/2017 | Fujita | A61M 5/14248 |
| 2017/0259015 | A1 | 9/2017 | Caspers | |
| 2018/0353704 | A1 * | 12/2018 | Helmer | A61M 5/2466 |
| 2019/0240417 | A1 * | 8/2019 | Hostettler | A61M 5/31511 |
| 2019/0274924 | A1 * | 9/2019 | Barmaimon | A61L 2/07 |
| 2019/0374707 | A1 * | 12/2019 | Damestani | A61M 5/1456 |
| 2020/0001068 | A1 * | 1/2020 | Donze | A61M 5/5086 |
| 2020/0297917 | A1 * | 9/2020 | Helmer | A61M 5/001 |
| 2020/0316290 | A1 * | 10/2020 | Bourelle | A61M 5/31 |
| 2020/0397984 | A1 * | 12/2020 | Reed | A61M 25/02 |
| 2020/0405950 | A1 | 12/2020 | Burren et al. | |
| 2020/0405951 | A1 * | 12/2020 | Burren | A61M 5/14248 |
| 2020/0405952 | A1 * | 12/2020 | Rytz | A61M 5/46 |
| 2021/0001048 | A1 * | 1/2021 | Schrul | A61M 5/14248 |
| 2021/0030949 | A1 * | 2/2021 | Damiano | A61M 5/162 |
| 2021/0038805 | A1 * | 2/2021 | Goldstein | A61M 5/172 |
| 2021/0093849 | A1 * | 4/2021 | Stumpe | A61M 5/158 |
| 2021/0128844 | A1 * | 5/2021 | Boyaval | A61M 5/326 |
| 2021/0170095 | A1 * | 6/2021 | Diperna | A61M 5/16809 |
| 2021/0260279 | A1 * | 8/2021 | Boyaval | A61M 5/178 |

FOREIGN PATENT DOCUMENTS

| | | | |
|---|---|---|---|
| EP | 3260149 A1 | 12/2017 | |
| EP | 3260151 A1 | 12/2017 | |
| EP | 3052166 B1 | 4/2019 | |
| EP | 3539591 A1 | 9/2019 | |
| EP | 3539592 A1 | 9/2019 | |
| EP | 3539596 A1 * | 9/2019 | ........ A61M 5/14248 |
| EP | 3545997 A1 | 10/2019 | |
| EP | 3582825 A1 | 12/2019 | |
| EP | 3697475 A1 | 8/2020 | |
| WO | WO-9959665 A1 * | 11/1999 | ........... A61M 25/02 |
| WO | 2006067217 A2 | 6/2006 | |
| WO | 2008068695 A1 | 6/2008 | |
| WO | WO-2011015659 A1 * | 2/2011 | ............... A61B 5/00 |
| WO | 2011064780 A2 | 6/2011 | |
| WO | WO-2011075099 A1 * | 6/2011 | ........ A61M 37/0015 |
| WO | 2017089271 A1 | 6/2017 | |
| WO | 2017089286 A1 | 6/2017 | |
| WO | 2017219155 A1 | 12/2017 | |
| WO | 2018151890 A1 | 8/2018 | |
| WO | 2019175688 A1 | 9/2019 | |
| WO | 2019175689 A1 | 9/2019 | |
| WO | 2019175690 A1 | 9/2019 | |
| WO | 2019186375 A1 | 10/2019 | |

OTHER PUBLICATIONS

International Search Report and Written Opinion received for International Application No. PCT/IB2019/051357 mailed on May 7, 2019, 12 pages.
International Search Report and Written Opinion received for International Application No. PCT/IB2019/051358, mailed on May 15, 2019, 9 pages.
International Search Report and Written Opinion received for International Application No. PCT/IB2019/051359, mailed on May 15, 2019, 10 pages.
International Search Report and Written Opinion received for International Application No. PCT/IB2019/052421, mailed on Aug. 6, 2019, 10 pages.
International Preliminary Report on Patentability received for International Application No. PCT/IB2019/051357, mailed on Sep. 15, 2020.
International Preliminary Report on Patentability received for International Application No. PCT/IB2019/051358, mailed on Sep. 15, 2020.
International Preliminary Report on Patentability received for International Application No. PCT/IB2019/051359, mailed on Sep. 15, 2020.
International Preliminary Report on Patentability Received for International Application No. PCT/IB2019/052421, mailed on Sep. 29, 2020, 6 pages.

* cited by examiner

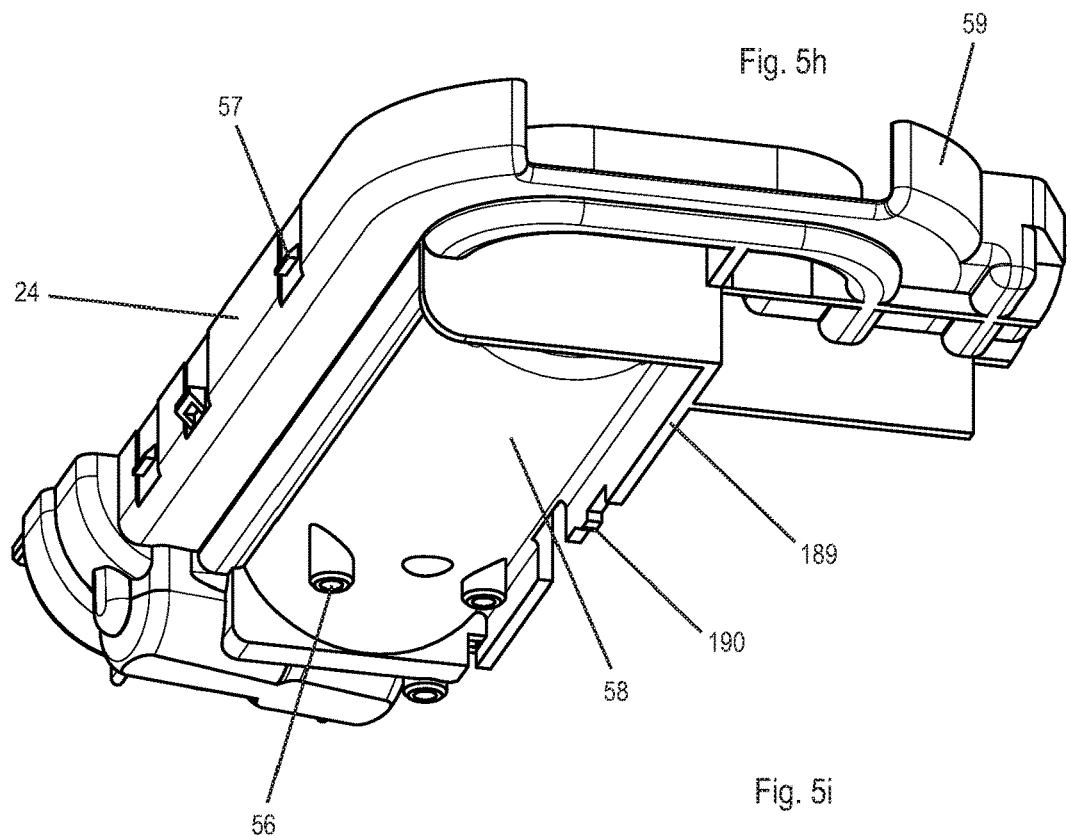
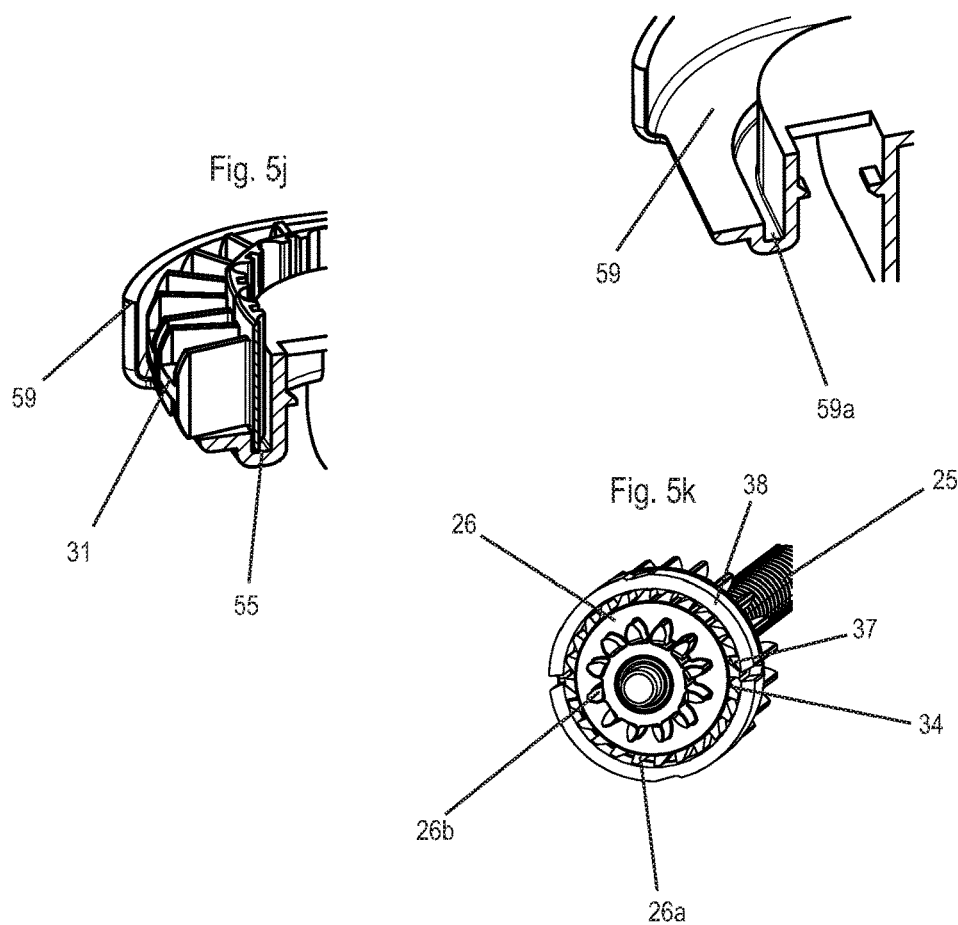

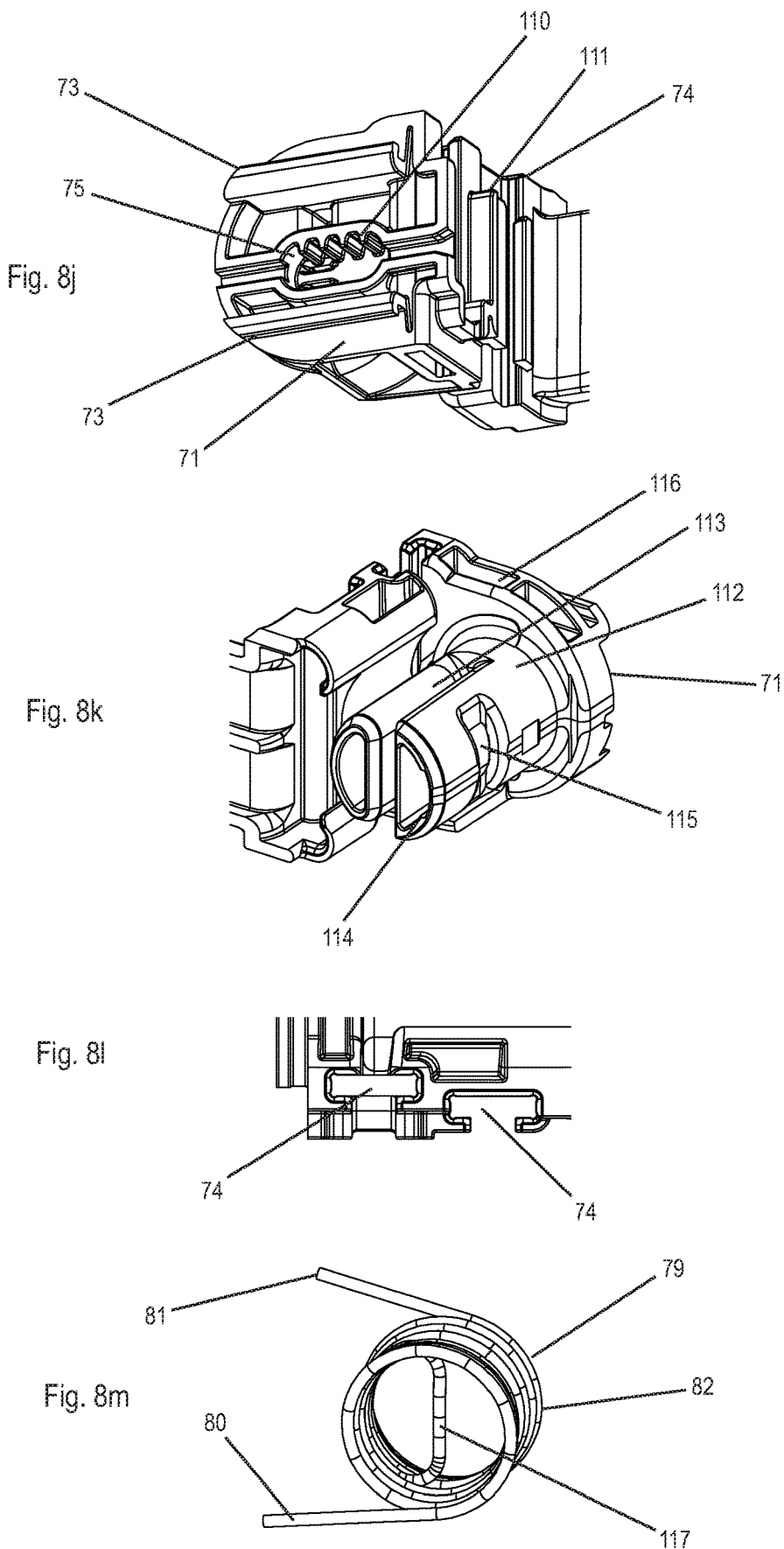

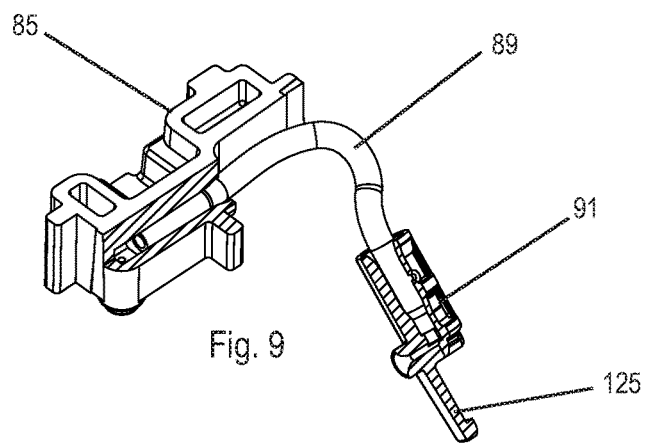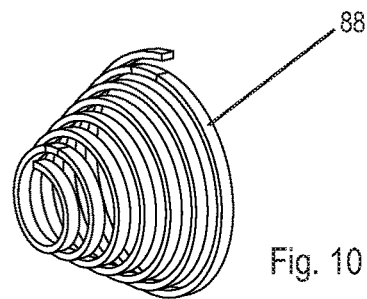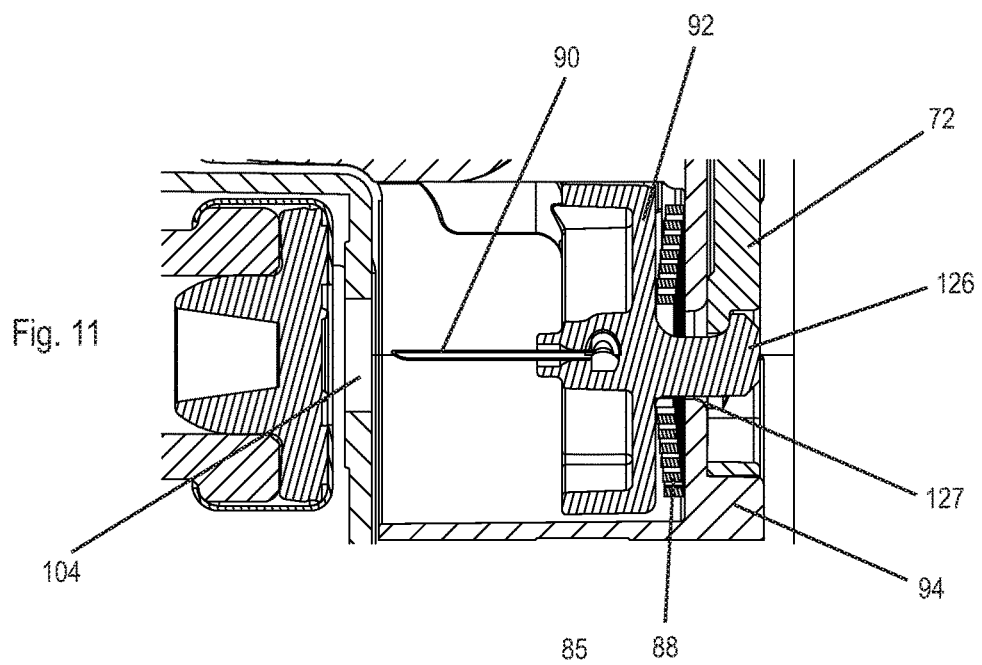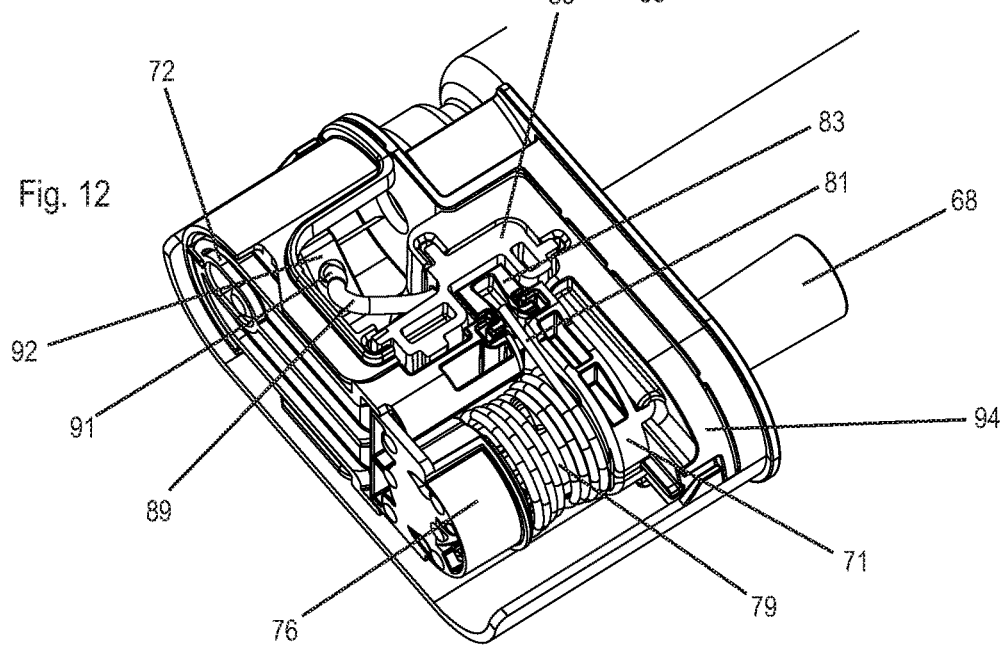

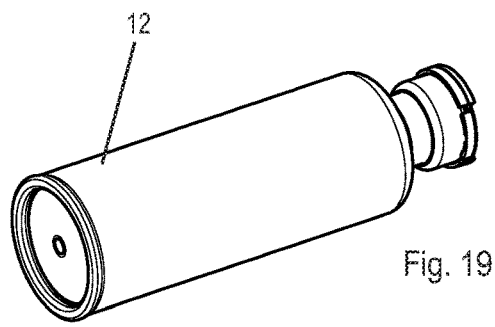
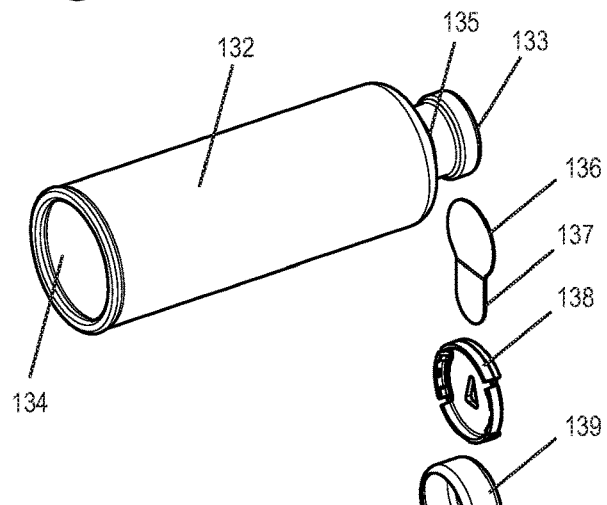
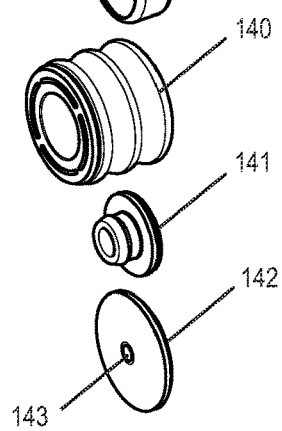

INJECTION OR INFUSION DEVICE COMPRISING AN IMPROVED HOUSING AND RELEASE LINER FOR REMOVING STERILE BARRIER FILMS USING THE RELEASE LINER

CROSS-REFERENCE TO RELATED APPLICATIONS

This application is a continuation of International Patent Application No. PCT/IB2019/051359, filed Feb. 20, 2019, entitled "AN INJECTION OR INFUSION DEVICE COMPRISING AN IMPROVED HOUSING AND RELEASE LINER FOR REMOVING STERILE BARRIER FILMS USING THE RELEASE LINER," which claims priority to European Patent Application No. 18161873.7, filed Mar. 15, 2018, and European Patent Application No. 18164145.7 filed Mar. 27, 2018, and European Patent Application No. 18207849.3 filed Nov. 22, 2018, each of which is incorporated by reference herein, in the entirety and for all purposes.

TECHNICAL FIELD

Injection devices are configured for attachment to the skin of a patient using an adhesive layer. More particularly, the injection devices comprise a release liner covering the adhesive layer, and the release liner is used to remove sterile barrier films located within the housing when the release liner is removed.

BACKGROUND

Injection and infusion devices are used for the subcutaneous delivery of liquid medicaments to a patient. Such injection devices are often pen-shaped, having a long axis and are called injection pens. The injection pens comprise a housing, which can hold a dose setting and dose delivery mechanism. The medication is preferably present in a cartridge or in a prefilled syringe. A cartridge is normally attached to the housing of the injection pen using a cartridge holder. The user sets a dose of medication which is subsequently delivered from the cartridge. Such injection pens are used to deliver separate injections and not intended for continuous delivery of a medicament. The needle is attached to the injection pen each time before use and the needle penetrates a septum that is attached to the cartridge.

Infusion devices deliver the medication from the cartridge using a drive mechanism and a control mechanism that controls the advancement of a piston rod that abuts a moveable plunger present in the cartridge containing the medication. The medication is delivered to the patient via a fluid path and an external infusion set comprising a needle for subcutaneous delivery. With such infusion devices both continuous and temporary medicament delivery profiles can be programmed.

A patch device is an example of an infusion device that is attachable to the skin of the patient. Such patch devices do not need an external infusion set for delivery, as the needle is directly contained in the patch device and may be inserted into the patient therefrom.

The injection and infusion devices comprise a dose setting mechanism, a delivery mechanism, a needle insertion and retraction mechanism or a needle shield protection system which is connected or connectable to a drive mechanism. The drive mechanism is driven by a power source which supplies energy to the injection or infusion device for executing tasks such as medication delivery, establishing a connection between the fluid path and the cartridge, needle insertion, needle retraction, advancing and/or retracting a piston rod, signaling to the user that the medication is in progress and/or complete, signaling to the user that the device can be removed, powering a processor unit in the device or establishing a wireless connection for data transmission to an external device such as a smart phone. The power source used in such injection or infusion devices can be selected from a wide variety of options such as, but not limited to, a spring (compression, torsional spring, and leaf spring), an electric motor, a battery, pressurized gas or liquid-hydraulic systems and the like. In the injection and infusion devices, several operations need to be arranged in a certain sequence for a correct operation and transmission of power from the energy source to final medicament delivery, for example, by advancing the plunger in the cartridge.

For a patch injection device, the needle must be inserted first, either using a steel needle (also called cannula) or a combination of a steel needle with a soft cannula; subsequently the steel needle must be retracted to leave the soft cannula in the subcutaneous tissue of the patient, followed by delivery of medication. Preferably, the needle, either a soft needle or a steel needle is retracted into the device before the patch device can be removed from the body. Alternatively, the needle is not retracted but a needle shield is extended from the body of the device to protect the needle tip and prevent needle sticks by the patient.

The liquid medicament is produced under sterile conditions and enclosed in a container to keep the medicament sterile. Such a container can be the above mentioned cartridge or an ampoule, both of which are preferably made of glass. As an alternative, plastic containers may be used. The cartridge comprises a barrel having two openings, one opening at the end of a neck portion and a second opening opposite to the neck portion. The opening at the neck portion is normally closed by a penetrable septum that is attached to the neck portion using a crimp. The opposite opening is closed by a plunger and the medicament is enclosed by the barrel between the septum and the plunger. During medication delivery, the plunger in the cartridge is advanced in the cartridge by the drive mechanism. The cartridge is filled with the liquid medicament in a fill finish line, and either the plunger is inserted first into the barrel and the medicament is filled via the neck portion followed by closure using the septum crimped onto the neck portion, or the septum is attached first to the cartridge's neck and the medicament is filled from the opposite opening and finally closed by the plunger. The fill finish is done in a sterile environment. The filled cartridge is normally subjected to a visual inspection to ensure that no particulates are present in the liquid.

The filled cartridge is assembled with an injection or infusion device, preferably a patch device, having a fluid path unit that is used for establishing the connection between a fluid path and the liquid medicament. The fluid path unit comprises a compartment or containment for housing a fluid path in the interior. The fluid path may comprise a needle or spike that can pierce through the septum of the cartridge, a tube or conduit for fluid transfer connecting the needle or spike to a second needle (which is either a soft needle and/or a steel needle) intended for penetrating the skin of the patient. Preferably, during storage (e.g., prior to use) there is no connection between the cartridge and the fluid path, and just prior to use the connection is established by penetrating the septum of the cartridge with the spike or needle. The interior of the compartment or containment for the fluid path unit is sterilized during manufacturing and remains in a sterile condition during storage. The fluid path unit and the cartridge can be assembled in a sterile environment which may be cumbersome (for example in view of the visual inspection) and expensive, or it is assembled in a non-sterile environment such as a clean room. The device comprising the assembly of the fluid path unit and cartridge can be in a sterile packaging during the storage, which is removed just before use or it is in a non-sterile packaging. In either option, a sterile connection needs to be established between the content of the cartridge and the fluid path in the compartment or containment of the fluid path unit prior to use, and this is usually done in a non-sterile environment.

US20160199568 discloses an infusion device with a peristaltic pump. The tube of the pump is connected to a connector assembly comprising an ampoule with a liquid medicament and a connector for the tube. Between the ampoule and the connector there are two strips to prevent the liquid passing from the ampoule to the tube. The ampoule is directly closed by a film and not with a septum, and the connector for the tube is always connected to the ampoule— there is no spike or needle for establishing the connection between the liquid medicament just prior to use. Removing the strip simultaneously establishes: a) a fluid connection between the cartridge and the tube, and b) a sterile connection between the ampoule and the tube. The fact that there is no separate closure for the ampoule reduces the reliability of the fixed connection and cannot be used for a modular assembly approach, moreover it will be cumbersome to use standard fill-finish procedures and standard components (such as a cartridge closed by a septum) for the device described in US20160199568.

In U.S. Pat. No. 4,019,512 a sterile connection between two connector ends of two tubes is established in a non-sterile environment by removing two strips from the two connector ends. The two strips keep the ends of the tubes in a sterile environment during storage, and the strips are removed after the two connector ends have been connected. A sterile connection is established between two tubes and is not intended or suitable for establishing a connection between a cartridge and a fluid path of an infusion device.

In WO 2018151890 a drug delivery device comprising a sterile fluid flow path is disclosed. Removable membranes are attached to sealing members that are part of the cartridge, and to an end of a fluid pathway. The membranes ensure that the sealing members remain in a sterile condition during storage and they are removed prior to moving the fluid pathway assembly towards the cartridge or the cartridge towards the fluid path assembly. The removable membranes may be connected to a membrane removal member to remove the membranes from the sealing members. The membrane removal member may be connected to a liner covering an adhesive layer attached to the device, and both removable membranes are attached to one side adjacent a passage in the liner, which may lead to increased mechanical stresses in the liner when removed and potentially lead to liner fracture. Additionally, no details for the passage are disclosed or means to prevent liner fracture.

It is an object of the present invention to overcome the above mentioned drawbacks and provide an injection device comprising an improved housing and release liner for removing sterile barrier films using the release liner and to improve the reliability and usability of the device. Additionally, the improved housing and release liner facilitate the assembly of the device.

These objectives are solved by providing a notch? in the housing, the skin adhesive layer and the release liner which form a passage for the films that are part of the removable sterile barrier and which allow for easy insertion of the films. The notch may be U-shaped and the ends of the films that are connected to the release liner are attached to the release liner at different locations adjacent the notch to reduce the mechanical stresses upon liner removal. The notch may be closed by a cover to guide the films and finally the release liner may be further strengthened using a strengthening sheet.

SUMMARY

In priority European Patent Application EP18161873.7, a cartridge is provided that is closed with a septum, and therefore steps a) and b) that are mentioned above and occur simultaneously in the prior art are separated from each other in the present disclosure. First a sterile connection is established between the fluid path and the standard cartridge, and secondly, the spike or needle of the fluid path penetrates the septum of the cartridge to establish the fluid connection. The advantage of having a standard cartridge closed by a septum and crimp is that standard production procedures can be used for fill-finish of the cartridge using standard components, which increases the reliability of the assembly and the acceptance by pharmaceutical companies. A modular approach can be used, and for instance, the cartridge may be filled at a different location than the assembly with the fluid path unit. Another advantage is that the cartridge with the sterile surface on the septum can be assembled with the sterile fluid path unit in a non-sterile environment. The connection shown in US20160199568, in contrast, must be assembled in a sterile environment.

In priority European Patent application EP18161873.7, the septum of the cartridge is covered by a sterile barrier film and/or a passage inside of the injection device is covered by a sterile barrier film. The films are intended to keep the surface of the septum in a sterile condition and/or to keep a fluid path unit enclosed in a compartment having the passage in a sterile condition. The ends of the films extend through a passage in the housing and through a passage in an adhesive layer configured for attaching the device to the skin of the patient. Prior to use, the adhesive layer is covered with a release liner protecting the skin adhesive layer. The ends of the sterile barrier films are connected to the release liner, and the two sterile barrier films are removed simultaneously from the septum and the passage, respectively, when removing the release liner from the adhesive layer. For a correct attachment of the ends of the sterile barrier films to the release liner, also a passage or aperture in the release liner is required. The sterile barrier films that are attached to the septum and to the passage, respectively, of the fluid path, need to extend through the passages in the housing, the adhesive layer and the release liner before the end of the sterile barrier can be attached to the surface of the release liner. No details for the passage are disclosed or means to further prevent liner fracture.

The injection devices of the present disclosure comprise the following units:

A housing unit (HU) that the user holds for placing and attaching the injection device to the skin and which encloses the other subassemblies is described herein. The housing unit may have a starting button accessible to the user for starting the injection and a sensing patch unit (SU) attached to an outside surface. The housing unit may have a viewing window for viewing a part of a cartridge unit (CU) enclosed within the housing that will be described below as well. Furthermore, the housing unit may have selected areas intended for providing visual signaling to the user. The selected areas may be transparent or semi-transparent to view an optical indicator. The housing unit may have an opening for receiving the cartridge unit and the opening may be closed using a cover.

A control unit or printed circuit board unit (PU) which controls the device based on signals received from the sensing patch unit, from a drive unit (DU) having a power source such as an electric motor or on signals received from an external source via a wireless communication such as a Bluetooth connection. The control unit comprises a printed circuit board (PCB) and the electrical power may be supplied by a battery present in the drive unit. The electronic circuitry of the injection device comprises the battery, the PCB and optionally the sensing patch unit (SU) comprising sensors that will be described below. The electronic circuitry may be open, i.e., switched off during storage and closed just prior to use in order to increase the lifetime of the battery or, alternatively, the electronic circuit is closed, i.e., switched on during storage. In the latter case, the control unit may have means for providing electric pulses applied at a certain frequency or duty cycle to the SU to check the status of the sensors (i.e., receive signals from the sensors) and therewith the status of the device and increase the battery lifetime when the electrical circuitry is always switched on. The PCB may have a push button switch which may be pressed upon by the starting button for starting the injection of the device. The push button switch may be in a disabled (or silent) mode during storage and enabled (activated mode) when the sensing patch unit provides a signal that, for example, the device is attached to the skin of the patient. The control unit may provide signals to the user of the device such as audible, tactile or visual status signals related to the start, progress, and end of the injection, or when there is a malfunctioning of the device. Examples of the malfunctioning include an occlusion in the medicament delivery system, low battery power, removing the device from the injection site prior to finalizing the injection, or failure to insert or retract the needle from the patient's skin. The printed circuit board unit may also send the status signals to an external source such as a smart phone using a Bluetooth connection.

The injection device further comprises a drive unit (DU) comprising a drive housing supporting the components of the drive unit. Once the device and the drive unit is activated or powered, it advances a piston rod from a retracted position to an extended position for delivering a medicament from a cartridge unit (CU) via a needle unit (NU) to the patient. An example of such a power package is a battery powering an electric motor, where both may be part of the DU. Alternative power packages such as pneumatic, hydraulic or spring driven mechanisms may be used as well, which are operated either purely mechanically or are supported by the battery powered electric motor. The housing of the of the drive unit supports and guides the piston rod either for a pure linear advancement, or the piston rod may be segmented and guided to perform a U-turn in order to reduce the dimensions (length) of the device. The segments of the piston rod may be connected to each other using hinges or they may be non-connecting elements that are guided by the housing of the drive unit into the cartridge unit. A gearing mechanism is part of the drive unit and the gearing mechanism transforms a rotation of the electric motor into piston rod advancement. The piston rod may rotate around its axis or slide during advancement. For rotational advancement, the piston rod is threadedly engaged with the housing of the drive unit, for non-rotational advancement the piston rod is splined to the housing of the drive unit. For example, the gear mechanism may rotate a threaded rod which is threadedly engaged with a piston rod that is splined to the housing such that the piston rod advances without rotation as the threaded rod is rotated. The gear mechanism may comprise a plurality of gear wheels including worm wheels and the gear mechanism may engage a gear wheel that is part of a cam shaft (CT) driving the needle insertion and retraction mechanism in the needle unit (NU). The control unit may control the rotation, the rotational speed and the rotational direction, and therewith control and switch between the different operational states of the device, e.g., at rest, needle insertion into the patients skin, establishing a fluid communication between the cartridge unit and the needle unit, delivery of the medicament, and retracting the skin piercing needle into the needle unit upon completion of the injection. The rotation of the electric motor may be switched from non-rotating when the device is sleeping during storage, into rotation in a first rotation direction for activating the needle insertion mechanism of the needle unit comprising the skin piercing needle and cartridge needle to establish the fluid connection between the patient and the cartridge unit. Subsequently the rotation direction is reversed in the second direction to advance the piston rod and expel medicament from the cartridge unit and finally the rotation direction may switch back to the first direction for retracting the skin piercing needle from the patient. The rotation is transmitted from the electric motor to the drive unit (piston rod) and the needle insertion mechanism (needle unit) via the gearing mechanism to gear up or gear down the rotational speed of the electric motor. The electric motor thus may generate different rotational speeds for each rotation direction and for each operation status. The mechanism for advancing the piston rod, for example via the threaded rod described above, may be permanently coupled to the gearing mechanism or there may be a coupling mechanism between the gearing mechanism and the threaded rod such that piston rod advancement mechanism can be decoupled from the operation of the needle unit. The needle unit may be permanently coupled to the gearing mechanism or a second coupling mechanism may couple or decouple the rotation from the gear mechanism to the needle unit. The coupling mechanism may be a one-way coupling mechanism such that rotation in one rotation direction is transmitted either to the needle unit or to the threaded rod of the piston rod drive mechanism. The one-way coupling may be an axial or radial one-way ratchet system.

The drive unit housing may provide structural support to other components of the injection device and may hold the PCB unit, the needle unit or the cartridge unit. The drive unit housing may support and provide guidance to contacting elements that enable the transfer of signals from a sensor layer that is part of the sensing patch unit to the PCB unit. The drive unit is configured to be connected to the housing unit.

A sensing patch unit (SU) is attached to the outside surface of the housing and comprises a multilayered system having at least one adhesive layer for attachment to the housing, one skin adhesive layer for attachment to the skin of the patient, one release liner layer covering the skin adhesive layer, one sensor layer comprising sensors, such as capacitive sensors, one layer having contacts for contacting the sensors in the sensor layer to the control circuit located at the printed circuit board. The sensors in the sensing patch may be capacitive sensors, and the capacity of the sensors may depend on the presence or absence of the release liner and whether the sensors are in close contact with the human skin. The release liner may have electrically conductive areas at least partially shielding the capacitive sensors in the sensor layer and therewith the release liner removal may be detected by the sensors as the dielectric and therewith capacitance is changed due to the removal.

Once the device is attached to the skin, the capacitance may change once again or reach a certain level, which is measured by the sensors in the sensor layer and signaled to the PCB. The capacitive sensors are powered by the battery present in the drive unit via the contacting elements that may be guided through the drive unit. The sensor layer may have a plurality of sensors embedded therein or printed thereon. The capacitance is measured and transmitted to the control unit of the PCB and the data are used to, for example, enable the push button switch or even automatically start the injection procedure. The sensors in the sensor layer may be formed as electrically conductive areas in the sensor layer for example by printing or by galvanic or chemical deposition of metals (such as silver, gold, aluminum, copper or metal alloys) onto a base sheet forming the sensor layer. Alternatively, an electrically conductive carbon layer may be used as the sensor which is, for instance, printed onto the base sheet or formed by local carbonization of the base sheet. Laser light that locally carbonizes a polymeric sheet of base material such as polycarbonate or polyethyleneterephthalate may be used for that purpose.

The sensing patch unit SU may not have a sensor layer but the sensors may be embedded in the housing of the injection device. For example, electrically conductive sensor areas may be injection molded directly onto or into the housing using two-component injection molding techniques, wherein one component is non-conductive whereas the other component is electrically conductive. The other component may, for example, be a carbon black filled plastic or a plastic filled with metal particles and the carbon black or the metal particles form a percolating network. Alternatively, the housing may be treated with laser light to locally carbonize the surface and form the sensor areas. As another alternative, the surface may be heat treated to form the conductive layer.

The multilayered system forming the sensing patch unit SU provides at least one passage for the skin insertion needle or for the films that are connected to the needle unit and/or cartridge unit within the housing. The films are guided via the passage in the housing and the passage in the sensing patch unit to the outside surface of the release liner.

The injection device further comprises the needle unit NU enclosed by a needle housing comprising a compartment enclosing a fluid path that can be sterilized, a receiving section for receiving the cartridge unit, and a needle insertion and retraction mechanism. The needle insertion and retraction mechanism enables the movement of the skin piercing needle from a retracted position inside the fluid path compartment through a passage to the outside of the compartment for skin insertion. The needle retraction mechanism moves the skin piercing needle back into the compartment after delivery of the medicament. The needle retraction mechanism is optional as the skin insertion needle may not be retracted into the device but instead a needle shield may protect the needle after delivery and the shield may move axially or rotationally from the inside of the injection device to the outside, thereby covering the tip of the skin piercing needle and avoid undesired needle sticks. The needle insertion mechanism may further provide means for inserting the cartridge needle from a position within the fluid path compartment to a second position outside the compartment thereby penetrating a septum of the cartridge unit. The needle insertion for the cartridge needle and skin piercing needle may occur simultaneously and the connecting conduit ensures that the medicament can flow to the patient. The cartridge needle and the skin piercing needle are may be oriented perpendicular to another. The cartridge needle and the skin piercing needle may be hollow steel needles that are each engaged with a carrier. Alternatively, hollow plastic needles may be used which may be rigid or flexible. In the latter case, the flexible needle may be inserted together with a rigid needle into the skin of the patient and the rigid needle is subsequently retracted.

The needles may have the opening at the tip and/or may have separate opening on the side (pencil tip configuration). The carriers may be slidably engaged within the fluid path compartment and driven by at least one resilient member from a first to a second position thereby inserting the cartridge needle into the cartridge unit and the skin piercing needle into the patient's skin. As a resilient member, springs may be used such as compression springs, torsional springs, leg springs or Belleville springs. Alternatively elastic elements, compressed gas or pyrogenic means may be used to insert the needles. The resilient member may directly engage with the carriers for the skin piercing needle or the cartridge needle, or the resilient element may engage an intermediate member that engages the carrier, having the advantage that tolerances may be compensated for that arise when the carriers move towards the inserted position. Controlling the release of the resilient member for needle movement is done using a needle control element. The needle control element is part of the needle unit and moves from a first position to at least one intermediate position into an end position. In the initial position, the control element blocks the movement of the needle carriers that are biased to move towards the inserted position. In an intermediate position, the carriers for the cartridge needle or the skin piercing needle may be released and the cartridge needle and/or the skin piercing needle move to the inserted position. In the end position of the needle control element, the skin piercing needle is retracted into the fluid path compartment or the needle shield is released to cover the non-retracted skin piercing needle. The control element may be slidably engaged with the needle housing and may move parallel to the bottom of the injection device from the starting to the end position or the control element may rotate through the several positions. The control element is driven by a cam shaft (CT) that is part of the needle unit and may be engaged with the gearing mechanism of the drive unit. The cam shaft is therefore rotated by the electric motor via the gearing mechanism. The rotation of the cam shaft may be converted into an axial movement of the control element using a gear rack and the rotation of the cam shaft may be converted in a rotation of the control element using a link-motion or another gearing mechanism. The fluid path compartment of the needle housing may have an opening that facilitates the assembly of needle insertion and retraction mechanism and the opening is closed by a needle cover (NC) that is glued, welded (for example laser welded or ultrasonic welded) onto the housing to close the opening after assembly. The fluid path compartment has passages that allows the cam shaft to engage with the drive unit, or allows the cartridge needle to pierce the septum of the cartridge unit, or allows the skin piercing needle to be inserted into the skin of the patient. For a safe operation of the device and to prevent contamination of the medicament, it may be required to sterilize the fluid path compartment and therefore the needle cover must form a sterile barrier for the opening in the fluid path compartment. Additionally, the passages for the cam shaft and the needles need to form a sterile barrier or are covered by a sterile barrier. The cam shaft may be engaged with the needle housing using an air tight seal such as an O-ring thus allowing for rotation of the cam shaft while preventing contamination of the fluid path compartment. The passages for the needle may be covered by a sterile barrier film that may be removed prior to the needle movements, as the needles may punch out a part of the film leading to needle blockage. The fluid path compartment may be sterilized via the passages, as the films covering the passages are porous and enable chemical gas sterilization. Alternatively, the films may be non-porous and radiation sterilization may be used for sterilizing the fluid path compartment or, alternatively, a separate window may be part of the needle housing, which may be covered by a porous film for chemical sterilization. The sterile barrier films require removal prior to use and therefore, the needle housing includes an aperture which may be a closed or a half open aperture, for example a notch, for guiding the ends of the films to the outside of the needle housing. The sterile barrier films may be removed as the user pulls on the end of the film or the ends of the films are attached to the release liner and removed together with the liner. The aperture is part of the fluid path compartment and/or the cartridge receiving section of the needle housing. Alternatively, the sterile barrier films may be removed as the ends of the films are connected to a film removal mechanism that is engaged with, and driven by the gear mechanism of the drive unit. The injection device comprises a cartridge unit (CU) which may be inserted just prior to injection, or the injection device is ready to use and already contains the cartridge unit. The cartridge unit comprises a hollow barrel having two open ends. The barrel may be constructed from glass and optionally constructed from a plastic such as polypropylene. At the distal end, the barrel narrows into a neck section which is configured for attaching a pierceable septum to the barrel. The septum is attached to the neck using a crimp cap. Opposite to the septum, the barrel is closed by a plunger, thereby enclosing the liquid medicament in a fluid tight manner. Advancement of the plunger by the piston rod of the drive unit expels the medicament from the cartridge once a fluid path connection has been established by piercing the septum with the cartridge needle. A cartridge adapter may be positioned between the plunger and the piston rod to compensate for an axial gap between the plunger and the distal end of the piston rod. The cartridge unit is receivable in a cartridge holder which is part of the needle housing or the housing unit. Once the cartridge is received in the cartridge holder, the septum is aligned with the cartridge needle. The barrel of the cartridge unit may be oriented parallel to the bottom of the housing unit intended for attachment to the patients skin. The surface of the septum that is not contacting the medicament may be sterile and protected from contamination during storage. A sterile barrier film may cover the surface of the septum and the septum's surface may be sterilized using chemical sterilization, steam sterilization or heat sterilization. A porous film may be used as sterile barrier film in combination with chemical sterilization such as ETO sterilization. The sterile barrier film may be attached to the crimp of the cartridge unit and the sterile barrier film may be protected by a protective cap that may be removed prior to inserting the cartridge unit into the device. The sterile barrier film may be removed before the cartridge needle pierces the septum. The sterile barrier film may therefore comprise a pull tab that the user removes before inserting the cartridge unit into the device or, for a ready to use device, the pull tab may be removed by the user once the CU is in the device, or the pull tab is attached to the release liner. Alternatively, the sterile barrier may be removed during production, just after the cartridge unit has been inserted. For removing the sterile barrier, the pull tab extends through each of the apertures in the needle unit, the cartridge holder and the housing unit before being available to the user for direct removal or for attachment to the release liner for removal using the liner.

The specific details for the removal of the sterile barrier films from the cartridge unit and the needle unit are described in the following paragraphs.

It is an objective of the disclosure to provide an injection device which is configured for attachment to the skin of a patient using an adhesive layer. The injection device comprises a housing, for example the housing unit (HU) described above, and the skin adhesive layer attached to an outside surface of the housing for attaching the injection device to the skin of a patient which is covered by a release liner thereby preventing skin attachment of the injection device. The skin adhesive layer and the release liner may be part of the sensing patch unit (SU). Furthermore, the injection device comprises a film having two ends, one end is connected to a surface inside of the housing and forming a removable sterile barrier, the other end is connected to an outside surface of the release liner that is not contacting the skin adhesive layer. The injection device may be characterized by a notch in the housing, in the skin adhesive layer and in the release liner defining a passage for the film from the inside to the outside of the housing. The notches in the housing, in the skin adhesive layer and in the release liner may be aligned with respect to each other to form the passage. A notch implies that the open end of the notch is located at a rim or border of the housing, the skin adhesive layer and the release liner, respectively. The notch in the housing may serve as the aperture described above that may be the housing unit, the cartridge holder or the needle unit. The film having two ends where one end is connected to the release liner and the other end inside the housing forming a sterile barrier may ensure that the film, and therewith the sterile barrier, can be removed simultaneously with the release liner in a single step, therewith improving the usability of the device, as the sterile barriers do not have to be removed separately. The notch in the housing and the alignment with the notches in the adhesive layer and the release liner enhances easy assembly of the device as the films can be inserted into the notch, and do not have to be passed through a closed aperture in the housing, which would be cumbersome.

The notch in the housing, the skin adhesive layer and the release liner may comprise a U-shaped aperture ending in a notch opening configured for receiving the film. The notch opening may facilitate the insertion of the film into the U-shaped aperture as it allow sideways insertion. A closed aperture requires insertion in a plane perpendicular to the plane of the U-shaped aperture which would be difficult in view of the amount of space available in the device. The U-shaped aperture includes two legs that may be oriented parallel to another and may facilitate the guidance of the film upon release liner removal when the films are attached to the release liner or even when the films are directly removed by the user.

The injection device may comprise two films, each film having two ends wherein one end of each film is connected each to one of two surfaces inside of the housing forming two removable barrier films and the other end of each film may be connected each to the outside surface of the release liner that is not contacting the skin adhesive layer. One of the two films may be attached to the needle unit (NU) and the other film may be connected to the cartridge unit (CU). The two surfaces inside the housing may be kept in a sterile condition during storage thereby preventing contamination of the surfaces during storage and therewith prevent contamination of the medicament during the injection upon use. Additionally, the fact that two films may be used has the advantage that the two subassemblies (CU and NU) can be produced separately, and if required at different locations, each can be sterilized using an appropriate sterilization technique. For example, the needle unit can be sterilized using radiation sterilization, whereas the cartridge unit comprising the medicament may be damaged by radiation and is sterilized using chemical surface sterilization.

The injection device may be configured such that one of the two other ends is connected to the release liner adjacent to one leg of the U-shaped aperture, whereas the other of the two other ends is connected to the release liner adjacent to the other leg of the U-shaped aperture in the release liner. Each of the two other ends may be each connected to one side of the U-shaped aperture and are therefore opposite to another. The advantage may be that the force that is required to remove the two films is distributed to two locations upon release liner removal thereby reducing the stress concentrations in the release liner and the potential for tear and damage of the release liner leading to partial liner removal. Additionally, the release liner may be unrolled from the skin adhesive layer, and by connecting the ends of the films to two locations surrounding the U-shaped aperture, the two ends that are removably connected to the inside of the housing and forming the sterile barrier can be removed one after another, which again reduces the initial stress in the release liner when the sterile barriers are removed. If the two ends of the films are connected to the same location, or on one side of the U-shaped aperture, then this may lead to undesired stress concentrations as the two films are simultaneously removed and the forces are directed to a single location only.

The notch opening of the injection device may be closed by a cover. When the notch opening is closed by the cover, a closed aperture may be formed surrounding the two films, thereby the play for the films is reduced and the films cannot leave the notch when the release liner is removed leading to a better control of the removal of the sterile barriers within the housing. The cover may be part of the housing unit (HU) and may close-off the opening that is available for receiving the cartridge unit (CU) as well. The cover may slide along the rim having the notch opening when the cover closes the housing.

The cover may be a separate housing cover that can be splined to the housing unit such that the separate housing cover can be guided when closing the housing and notch opening after receipt of the film. The film may be received in the notch opening during insertion of the cartridge unit (CU) into the housing unit. The cover may be engaged with the housing, and the cover already guided while the notch opening is still open and available for receiving one or two films, and subsequently the cover slides to the end position and thereby closing the notch opening forming a closed passage for the one or two films.

The notch in the housing may have rounded edges. During release liner removal the films may slide along the surface of the notch, such as along the surfaces forming the legs of the U-shaped notch, and the rounded edges may facilitate the smooth removal and prevent fracture of the films when the release liner is removed.

The one end of the film forming a removable sterile barrier may be connected to a surface of, and cover a passage in a fluid path compartment located in the housing, such as in the needle housing. The needle housing may comprise a cartridge needle configured to be moved within the fluid path compartment through the passage and the one end of the film forming a removable sterile barrier may keep the fluid path compartment in a sterile condition when covering the passage. The fluid path compartment located in the housing may comprise a fluid path having or consisting of a conduit connecting the cartridge needle to a skin piercing needle. The fluid path should be protected from contamination during storage and upon use the skin piercing needle and cartridge needle connect to the skin and cartridge respectively to provide a safe fluid connection between the medicament and the patient. The fluid path compartment encloses the fluid path and passages are available for the skin piercing needle and the cartridge needle which need to be closed by protective films preventing contamination during storage and which are free for passage of the needles during use. Therefore the films are removable films as otherwise the needles have to extend through the protective films first which may lead to needle blockage as the (hollow) needles may punch out a part of the film.

One end of the film forming a removable sterile barrier may be connected to the end of a cartridge or cartridge unit (CU) that is located within the housing and closed by a pierceable septum, the one end of the film forming a removable sterile barrier may cover the surface of the septum and keep the surface of the septum in a sterile condition while covering the septum. The medicament may be enclosed in a cartridge and kept sterile during storage. The cartridge may be closed by a septum and the outside surface may remain in a sterile condition, too during storage to avoid contamination. The cartridge with attached film may be sterilized prior to filling the medicament into the cartridge such that the film and the surface of the septum are sterile. This is achieved by the end of the film forming a sterile barrier and covering the septum. The film is removed such that the cartridge needle, driven by the insertion mechanism, is driven through the passage into the pierceable septum that is uncovered.

The one end of the film forming a removable sterile barrier may be connected to an end surface of the crimp (or crimp cap) holding the septum to the cartridge. The end of the film may be attached (for example by heat sealing, gluing or ultrasonic sealing) to the end surface of the crimp prior to attaching the septum to the cartridge using the crimp. In a subsequent step, the surface of the septum behind the end of the film is sterilized and remains sterile.

The cartridge needle present in the needle unit (NU) may be configured to be moved through the passage of the fluid path compartment into the pierceable septum of the cartridge unit when the one end of the film forming a removable sterile barrier covering the passage of the fluid path compartment as well as the one end of the film forming a removable sterile barrier connected to the end of the cartridge have been removed. When both ends of the films have been removed the passage of the fluid path compartment and the surface of the septum are free and the cartridge needle can pierce the septum without the risk of needle blockage due to punching of one or both of the ends of the films forming a sterile barrier.

Both films may be removed prior to use of the device such that the two sterile barrier films on the needle unit and the cartridge unit cover the passage of the fluid path compartment and the septum during storage. Alternatively, the films may be removed during production, after insertion of the cartridge and closure of the housing unit using the cover such that there are no sterile barrier films present during storage. In the latter option, the device may be packaged in a suitable packaging, for example a peel pouch or blister to prevent contamination of the surface of the septum during storage.

As another alternative, only one of the two films is removed and the cartridge needle pierces one of the two films that has not been removed. As yet another alternative, the two films are not removed and the needle pierces both films before penetrating the septum.

The film comprising both ends and the sterile barrier film may be a monolithic film, i.e., made of a single sheet of material, or the film comprises a pull-tab attached to the one end of the film forming a sterile barrier whereas the pull tab comprises the other end of the film connected to the outside layer of the release liner. The pull tab is made from a different material then the one end of the film forming a sterile barrier. The use of a separate pull tab ensures that different films for different purposes may be used. For the sterile barrier, porous membranes such as Tyvek® may be used which allow for chemical sterilization techniques (using ETO, Gas plasma (ozone), hydrogen peroxide or nitrogen oxide gases that may flow through the porous membrane) or that can be easily attached to the end of the cartridge, for instance to the end of the crimp. For the pull tab, films may be used that can be properly attached to the release liner or which have a higher tear strength. By using two different films using two different materials the versatility and flexibility during manufacturing and use may be enhanced.

The release liner for the sensing patch unit may be covered by a strengthening sheet adhesively connected to the outside surface of the release liner and covering the notch in the release liner and the other end of the film, e.g., the end of the film that is not forming the sterile barrier film within the housing. The release liner may be subjected to stresses when removing the sterile barriers from the inside of the housing as the forces required to release the removable connections are above the forces to remove the liner from the skin adhesive. These stresses may be concentrated around the notch as the ends of the films are attached adjacent to the notch. The strengthening sheet strengthens the release liner, particularly around the notch to prevent tearing or fracture of the release liner. Additionally, the bonding between the ends of the films connected to the liner may be strengthened as well. The strengthening sheet may be a polymeric sheet that is adhesively attached or welded/heat, or ultrasonic) to the release liner. Alternatively a woven or non-woven fiber material, for example, cotton or paper (cellulose) may be used to strengthen the release liner.

The release liner further comprises an aperture for the skin piercing needle used to pierce the skin, and an end of the skin piercing needle may be configured to be moved from a first position inside the housing to a second position outside the housing. The aperture for the skin piercing needle for piercing the skin may be covered by a removable second sterile barrier film adhesively attached to the strengthening sheet. The skin piercing needle is configured to move into the skin of the patient inserted from the inside of the fluid path compartment into the skin. The fluid path compartment may be kept in a sterile condition using the removable second sterile barrier film which may be attached or bonded to a second aperture of the fluid path compartment. The needle insertion mechanism may be configured for movement and insertion of the cartridge needle as well as the skin piercing needle for piercing the skin before expelling the medicament, whereas the skin piercing needle for piercing the skin can be retracted into the housing after the medicament has been expelled. The second sterile barrier film may be connected to the strengthening sheet and the strengthening sheet may be attached to the release liner such that liner removal also removes the second sterile barrier film.

The skin piercing needle for piercing the skin may be enclosed by the fluid path compartment of the needle unit and connected to the cartridge needle by a conduit.

The films may have at least one fold (U-turn for example) between the two ends of the film. The at least one fold may be close to the sterile barrier film covering the passage of the fluid path compartment or the end of the cartridge. This has the advantage that the film can peel off, or unroll from the passage or the end of the cartridge which reduces the forces required for film removal. If the film is unrolled, then the adhesive strength at a specific location only needs to be overcome and the film is removed step by step. If the film needs to be removed in a single step, for example if there is no fold, then the force required to remove the film is significantly higher A flip-off cap may cover the film that is attached to the end of the cartridge, such as to the end of the crimp. The flip-off cap may protect the film during attachment to the cartridge, transport and handling for the sterilization and fill finish steps. The flip-off cap may be at least partially removed from the crimp prior to insertion of the cartridge into a cartridge holder that is part of the housing and making the film available for insertion into the notch. The flip-off cap may have perforated sections forming predetermined breaking points such that the cap or a part of the cap can be removed easily. A part or portion of the cap may optionally remain attached to the end of the cartridge and may be used for correct alignment and positioning of the cartridge.

The injection device may comprise a sensor layer of the housing or attached to the housing. For example the sensor layer may be part of the skin adhesive layer or may be part of a layer positioned between the skin adhesive layer and the housing. The sensor layer may comprise capacitive sensors that are connected to the control unit within the housing using resilient connecting members. The sensor layer may be at least partially covered by a shielding layer, for example an electrically conductive layer that is part of the release liner or the strengthening sheet attached to the release liner. For example, the release liner may comprise a conductive layer such as a silver ink layer or carbon black layer that is printed or vapor deposited onto the liner. The sensor layer may be configured to detect the release liner removal as the capacitance (dielectric) for, or adjacent to, the sensors changes. Furthermore skin attachment may be detected as the capacitance of the sensors changes once again. The sensor signals may be forwarded to the control unit using the connecting members and may be used for notifying optically and/or acoustically the status of the device ("ready for attachment" or "ready to press the start button") or enable or activate the start button.

BRIEF DESCRIPTION OF THE DRAWINGS

While the invention has been described in detail in the drawings below and foregoing general description, such description is to be considered illustrative or exemplary and not restrictive. Variations to the disclosed embodiments can be understood and effected by those skilled in the art and practicing the claimed invention, from a study of the drawings, the disclosure, and the appended claims.

FIGS. 5a-5k: individual components drive unit DU.

FIG. 9: A fluid path of the injection device without the skin piercing needle and the cartridge needle shown.

FIG. 10: The cartridge needle slider spring of the injection device.

FIG. 11: A detailed view of cartridge needle slider in the mechanism holder of the injection device.

FIG. 12: The needle insertion assembly, cartridge needle and skin piercing needle in a retracted position.

FIG. 19: A cartridge unit CU of the injection device.

FIG. 20: An exploded view showing components of the cartridge unit CU.

FIG. 21: Details of the sterile barrier film, flip-off cap and crimp of the cartridge unit CU.

DETAILED DESCRIPTION

The term "medicament" or "medication" includes any flowable medical formulation suitable for controlled administration through a means such as, for example, a cannula or a hollow needle and comprises a liquid, a solution, a gel or a fine suspension containing one or more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from—or harvested by—biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances, The distal end or distal direction is defined by the direction of the needle configured to penetrate the skin of the patient. For an injection pen this may be the injection needle and the end of the pen holding the needle or being configured to hold the needle is the distal end. For an infusion device the distal end and the distal direction is towards the needle configured to penetrate the skin of the patient, which may be along the axis of the device or tilted or perpendicular to the axis of the device. The distal direction in an infusion device represents the direction in which the medicament flows towards the insertion needle. The proximal direction or end is opposite to the distal direction or end.

Figure 1A:
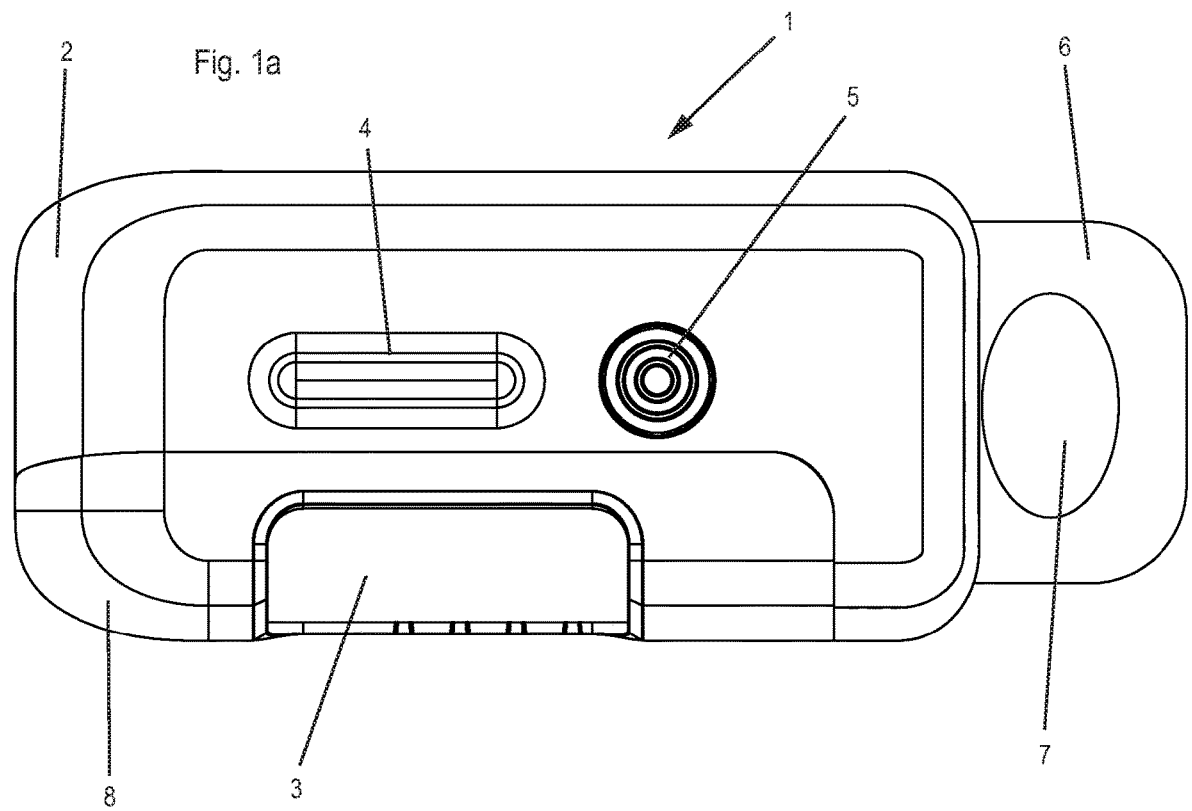
FIGS. 1*a*, 1*b*: Injection device.
Figure 1B:
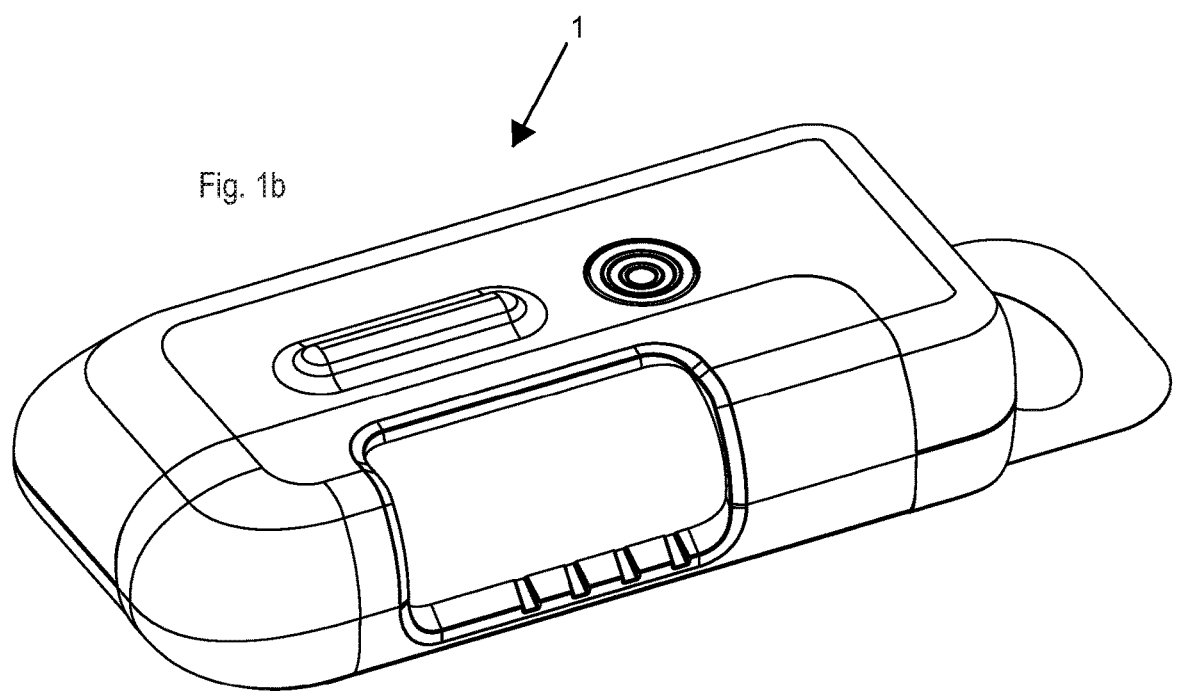

In FIG. 1a, the injection device (1) is shown which comprises a housing unit HU (2) having an indicator (4) and a push button (5). The housing unit HU (2) is closed by a cover (8) having a viewing window (3) for viewing a cartridge (not shown). The injection device can be attached to the skin of the patient by a skin adhesive layer which is part of a sensing patch unit attached to a bottom surface of the housing unit (2). The skin adhesive layer is covered by a release liner (6) which prevents undesired attachment of the injection device such that the patient can first select a suitable location for skin attachment. The release liner is a sheet of material that comprises a gripping area (7) facilitating the removal of the release liner by the user. The gripping area (7) may be roughened or having an elevated area that may be structured. Alternatively, the gripping (7) area may be an aperture in the sheet of material. The gripping area (7) may have visual indicators such as arrows or symbols printed thereon to instruct the user. A 3-dimensional perspective view of the injection device is shown in FIG. 1b.

Figure 2:
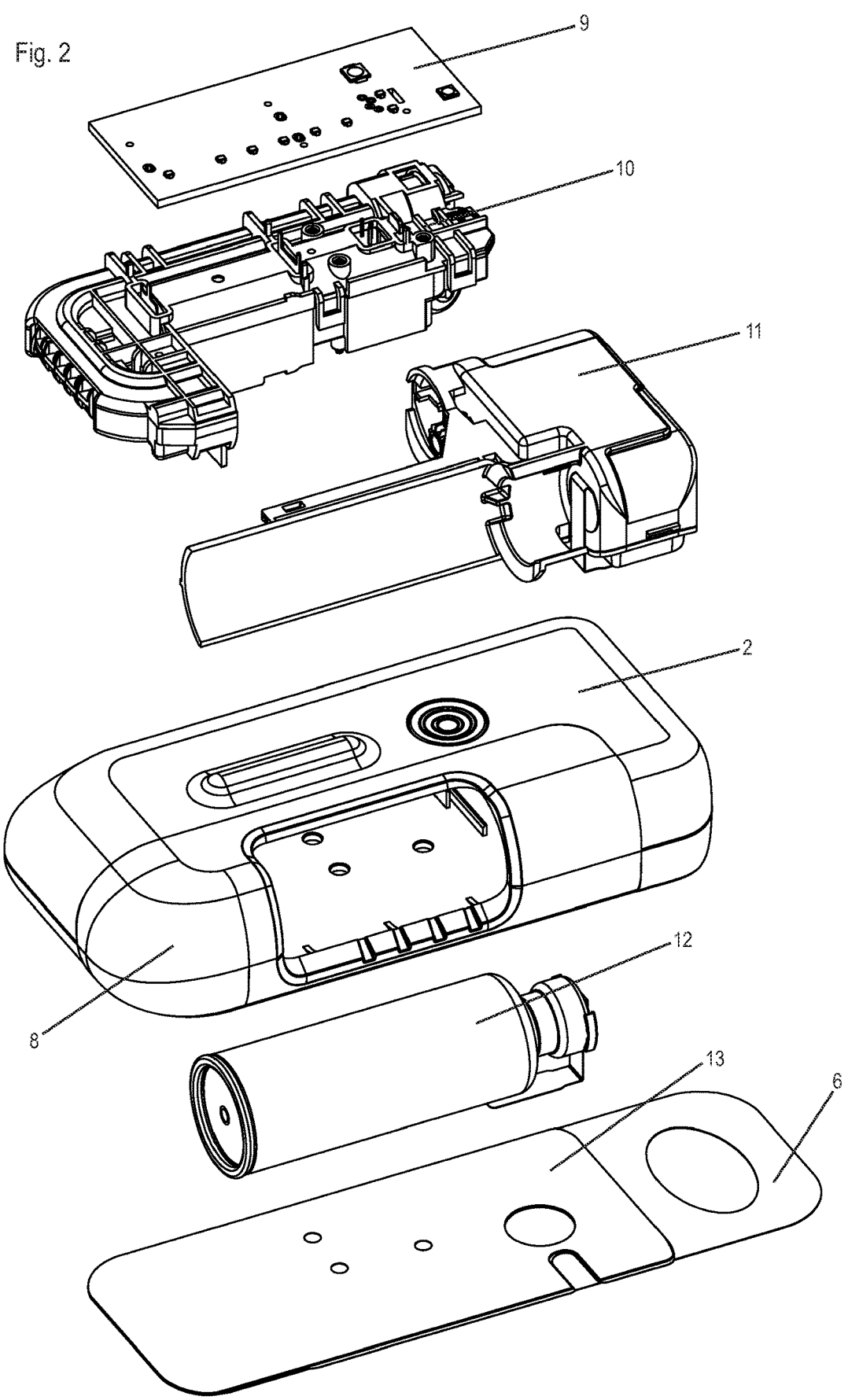
FIG. 2: An exploded view of the injection device showing the subassemblies.

An exploded view of the injection device (1) showing the subassemblies and components forming the injection device (1) is shown in FIG. 2. The injection device (1) comprises a printed circuit board unit PCB (9) for controlling the injection of the device (1), a drive unit DU (10) for driving a piston rod (of the drive unit DU), a needle insertion unit NU (11) with a needle insertion mechanism, the housing unit HU (2), a cartridge unit CU (12) and a sensing patch unit SU (13).

Figure 3:
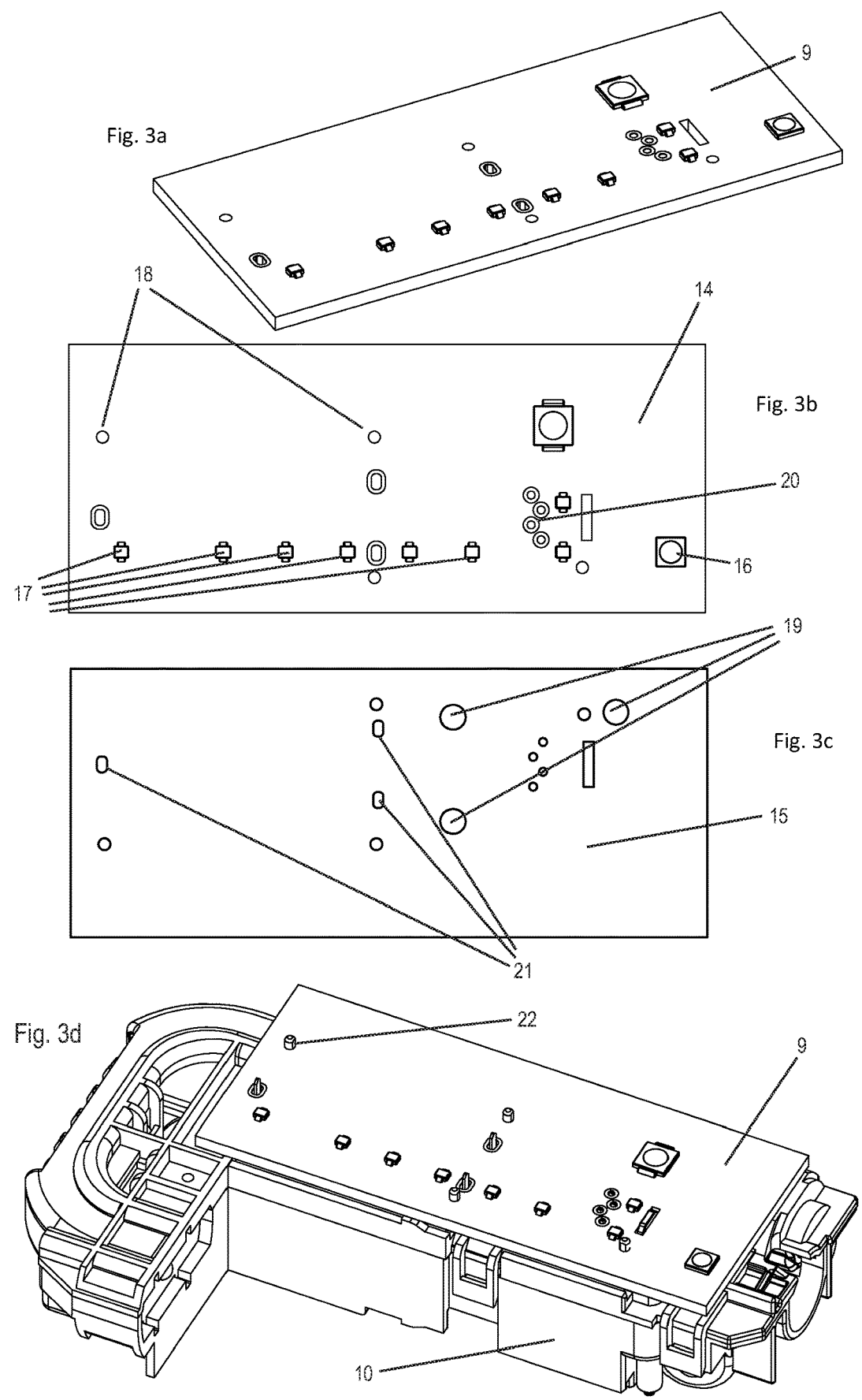
FIGS. 3a, 3b, and 3c: Views of the printed circuit board PCB unit of the injection device.
FIG. 3d: The printed circuit board PCB unit assembled with a drive unit DU of the injection device.

The printed circuit board unit PCB unit (9) is shown in FIGS. 3a, 3b and 3c and comprises a printed circuit board with conductive leads, integrated circuits, contacts for power supply, contacts for receiving signals from the sensing patch unit (13), contacts for sending signals to the electric motor, a switch and in some embodiments a wireless transmitter/receiver unit. The top surface (14) of the PCB unit comprises a push button switch (16), positioning apertures (18), LED light indicators (17) and through holes forming contacts (20) for a stepper motor. The bottom surface (15) comprises contacts (21) for contacting the battery and separate contacts (19) for contacting contact springs. The PCB unit (9) is positioned on top of the drive unit (10) using protrusions (22) of the drive unit that engage the apertures (18) of the PCB unit, see FIG. 3d. The PCB unit may be fixated by plastic deformation and/or melting the protrusions (22) after positioning the PCB unit on top of the drive unit (10). Alternatively, the PCB unit (9) is fixated using a snap-fit connection.

Figure 4:
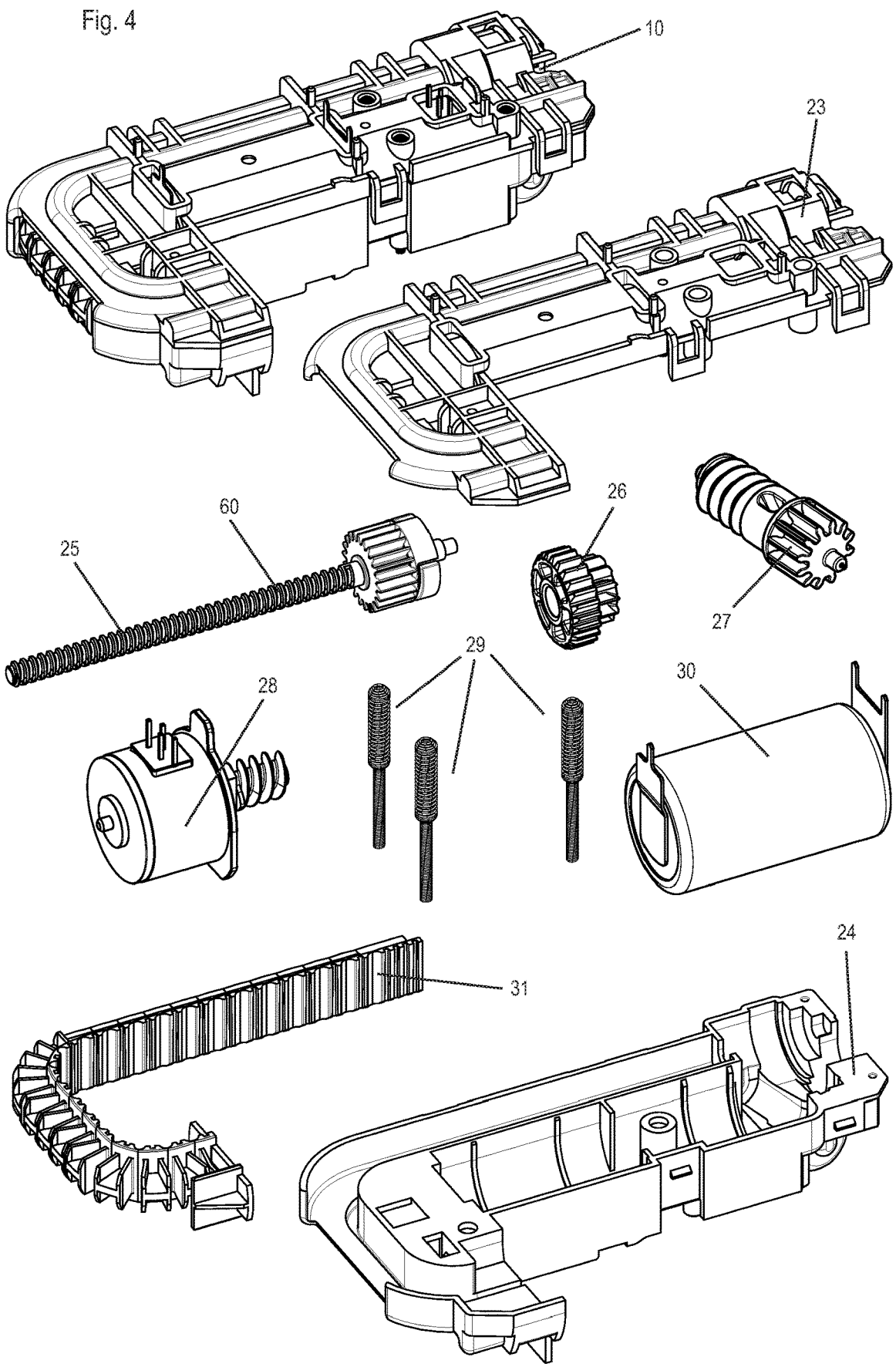
FIG. 4: An exploded view showing all components of drive unit DU.

An exploded view of the parts forming the drive unit DU (10) is depicted in FIG. 4. A drive cover (23) engages a drive carrier (24) thereby forming the housing for the drive unit (10). An elongated threaded rod TR (25) is received by bearings in the drive carrier (24). The threaded rod (25) is driven by an electric motor via a gearing mechanism and rotation of the threaded rod (25) is transformed in axial movement of a piston rod. The gearing mechanism comprises a gear shaft (27) and the gear mechanism is driven by a stepper motor (28). The gear shaft (27) is received by bearings in the drive carrier (24) and the stepper motor (28) is received in a preformed compartment of the drive carrier (24). The stepper motor (28) is powered by a battery (30) which is also enclosed in, and may be attached to the drive carrier (24). For example the battery (30) may be glued or adhesively attached to the drive carrier to prevent battery loosening upon mechanical impact. Alternatively, a press-fit connection is used to fixate the battery (30) using clips or a resilient foam material. A plurality of contact springs (29) are guided through the drive unit (10) establishing contacts between the sensing patch unit SU and the PCB unit. The contact springs (29) are made from an electrically conductive material, may be configured as spiral springs and may directly contact the sensing patch unit SU or the PCB unit or via contacting pins that are biased by the spring. The diameter of the contact springs (29) may vary to facilitate the positioning in one of the drive cover (23) or the drive carrier (24). The drive unit DU has a piston rod (31) which may be guided by the drive carrier (24) to form a U-shaped piston rod that is configured to advance a plunger in a cartridge for expelling the medicament from the device.

Figure 5A:
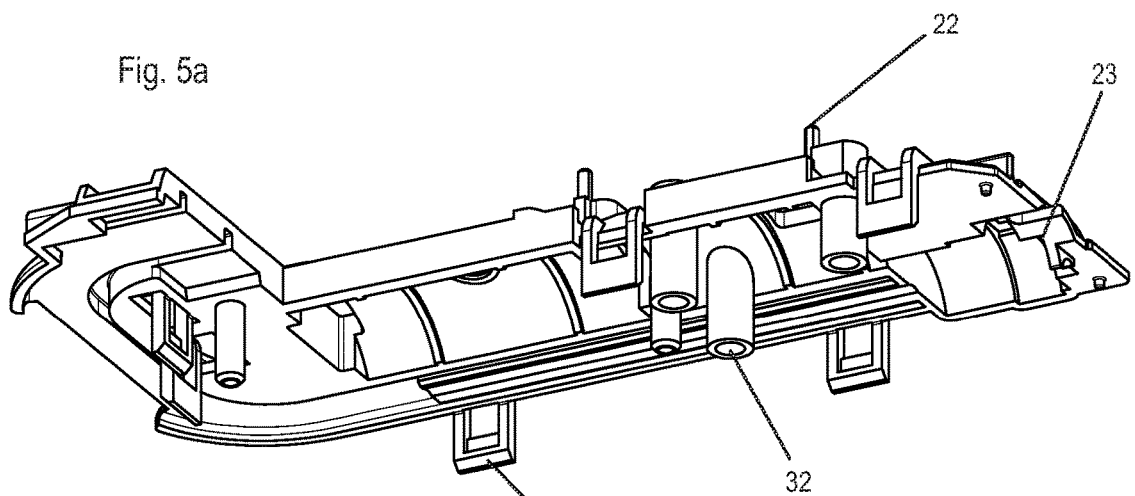
Figure 5B:
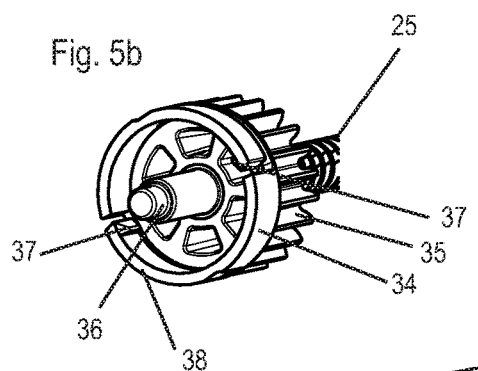
Figure 5C:
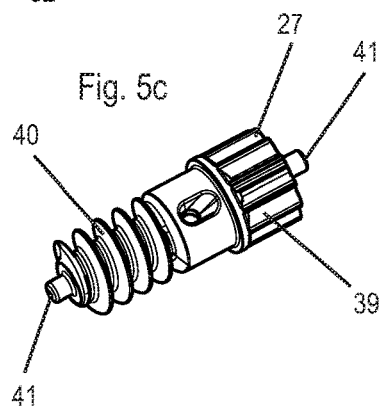
Figure 5D:
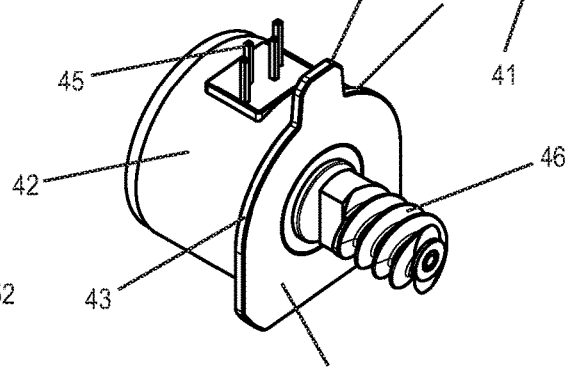

A detailed view of the components forming the drive unit DU (10) is shown in FIGS. 5a to 5k. In FIG. 5a, the drive cover DC (23) comprises the protrusions (22) for positioning and fixation of the PCB unit (9) and a snapper (33) or snap fit connector for connecting the drive cover to the drive carrier (24). The drive cover comprises cylindrically shaped apertures (32) that are aligned with complementary apertures of the drive carrier to form a passage for contacting springs. In FIG. 5b, the threaded rod (25) comprises a threaded rod driver (34), shaped as a gear wheel that is rotationally and axially fixed to the threaded rod (25) and comprises gear teeth (35) on the outside circumferential surface of the driver (34) and which are oriented parallel to the axis of the threaded rod. Adjacent to the gear teeth (35) there is at least one flexible arm (38) having at least one ratchet member (37) pointing towards the central axis of the threaded rod (25) (FIGS. 4 and 5h). The at least one flexible arm (38) surrounds a hollow space within the driver (34) that is available for the ratchet wheel (26). The threaded rod (25) has a shaft end (36) that is received in a bearing formed in the drive carrier (24) (FIGS. 4 and 5h). The shaft of the threaded rod (25) may engage a central opening of the ratchet wheel (26) (FIGS. 4 and 5h). The gear shaft (27) is shown in FIG. 5c and comprises a gear wheel (39) that is configured to engage a worm wheel of the stepper motor. Adjacent to the gear wheel (39), the gear shaft (27) comprises a worm wheel (40) that is configured to engage the gear teeth (35) of the threaded rod driver (34). The gear shaft (27) has shaft ends (41) that are received by bearings in the drive carrier (24). A detailed view of the stepper motor (28) is shown in FIG. 5d, the stepper motor comprises a motor (42) an end plate (44), contacts (45) and worm wheel (46) of the stepper motor. The end plate (44) has edges (43) to rotationally and axially fixate the stepper motor (28) in the drive carrier. The end plate (44) may have a handle (47) facilitating the gripping and automated positioning of the stepper motor (28) in the drive carrier (24). The worm wheel (46) of the stepper motor (46) engages the gear wheel (39) of the gear shaft (27) and the worm wheel (40) of the gear shaft (27) engages the gear teeth (35) of the driver (34) for the threaded rod (25). The worm wheel (46) of the stepper motor (28), the gear wheel (39) of the gear shaft (27), the worm wheel (40) of the gear shaft (27) and the gear teeth (35) of the threaded rod (25) form a gearing mechanism (46,39,40,35) to gear down the rotation of the motor (42) into a rotation of the threaded rod (25).

Figure 5E:
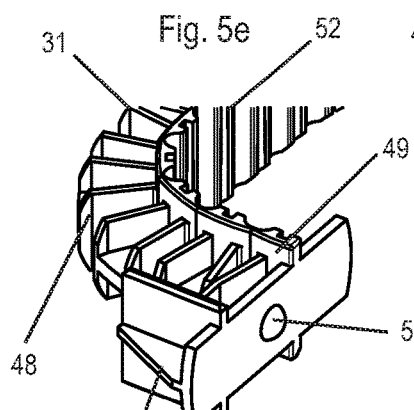
Figure 5F:
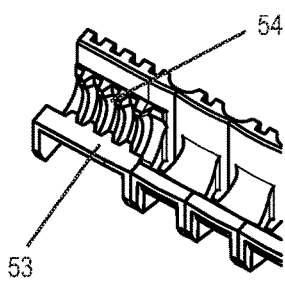
Figure 5G:
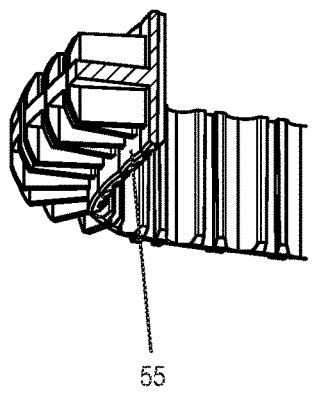

Details of the piston rod (31) are shown in FIGS. 5e, 5f and 5g. The piston rod comprises segments (48) that are connected to each other via hinges (52) such that the individual segments (48) can rotate with respect to each other. The segments (48) have a segment guidance (55) (FIG. 5g) that protrudes from each segment in a direction perpendicular to the direction for advancing the piston rod (31). In FIG. 5e, the last segment (49) of the piston rod comprises a protrusion (50) configured for engaging a spacer that is part of the cartridge unit to form a pivot bearing between the spacer and the last segment (49). The last segment (49) may comprise a guiding fin (51) that is configured to engage the barrel of the cartridge such that the last segment (49), and therewith the segmented piston rod, correctly enters the cartridge. In FIG. 5*f*, the first segment (53) of the segmented piston rod (31) comprises an internal threading (54) that engages an external threading of the threaded rod (25).

In FIG. 5*h*, the drive carrier (24) comprises cylindrical apertures (56) that are aligned with the apertures (32) of the drive cover (23) after assembly to guide the contact springs (29) through the drive unit DU (10). The drive carrier (24) furthermore comprises a holder (58) for the battery (30) and the stepper motor (28), and protrusions or snappers (57) that may connect, for instance irreversibly, to the snappers (33) of the drive cover (23). A guidance (59) guides the segments of the piston rod (31) such that the piston rod (31) may move from a straight or stacked configuration of the individual segments, to a curved configuration, and back to a straight configuration, by rotating the individual hinges between the segments. The piston rod (31) may have a U-shape due to the guidance (59) of the drive carrier. A detail of the segmented piston rod (31) engaging the guidance (59) is shown in FIG. 5*j*. The segment guidance (55) of each segment (48) engages a keyway (59*a*) (FIG. 5*i*) of the drive carrier (24) thereby further guiding the piston rod (31) and preventing rotation of the piston rod (31) around its own axis. The threaded engagement of the first segment (53) of the piston rod (31) with the threaded rod (25) is therefore transferred in axial advancement (or retraction) of the piston rod (31) once the threaded rod (25) is rotated via the gear mechanism (46, 39, 40, 35).

A coupling mechanism between the driver (34) of the threaded rod (25) and the ratchet wheel (26) is shown in FIG. 5*k*. The ratchet wheel (26) is inserted in the hollow space of the driver (34) onto the shaft and ratchet teeth (26*a*) on the outer surface of the ratchet wheel (26) to engage the ratchet member (37) of the driver (34). The interaction between the shaft of the threaded rod (25) and the ratchet wheel (26) is such that the ratchet wheel may rotate in both directions with respect to the shaft. However the ratchet teeth (26*a*) are asymmetrically shaped, such as saw tooth shaped that extend radially outwards, and the engagement with the ratchet member (37) mounted on a flexible arm (38) is such that the ratchet wheel (26) may rotate in one direction only due to the one way ratchet (37, 26*a*). Or, as the driver (34) is rotationally fixed to the threaded rod (25), rotation of the driver (34) in one direction may be transmitted to the ratchet wheel (26) due to the form fit between the teeth (37, 26*a*), whereas the ratchet member (37) ratchets over the teeth (26*a*) of the ratchet wheel (26) in the opposite direction thereby generating audible clicks. In the latter case the ratchet wheel (26) may not rotate or only rotates once a certain frictional resistance has been overcome.

Figure 6:
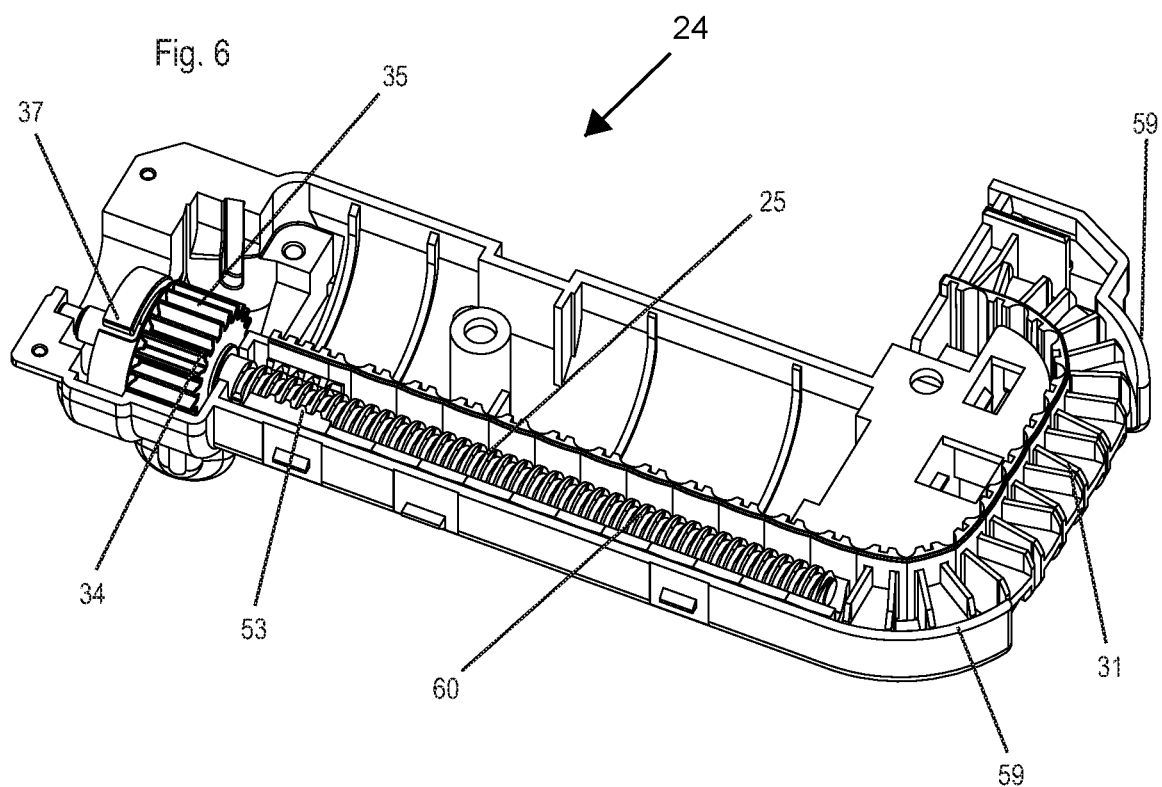
FIG. 6: A threaded rod, piston rod within drive carrier of the drive unit DU.

The drive carrier (24) supporting the threaded rod (25) engaging the segmented piston rod (31) is shown in FIG. 6. The threaded rod (25) comprises an external threading (60) which engages the internal threading (54) of the first segment (53) of the segmented piston rod (31). The segmented piston rod (31) is guided by two guidances (59) that direct the segmented piston rod (31) in a U-shape. Rotation of the threaded rod driver (34) via the gear mechanism (46, 39, 40, 35) will advance the piston rod (31), e.g., slide the piston rod, due to the threaded engagement with the first segment (53).

Figure 7:
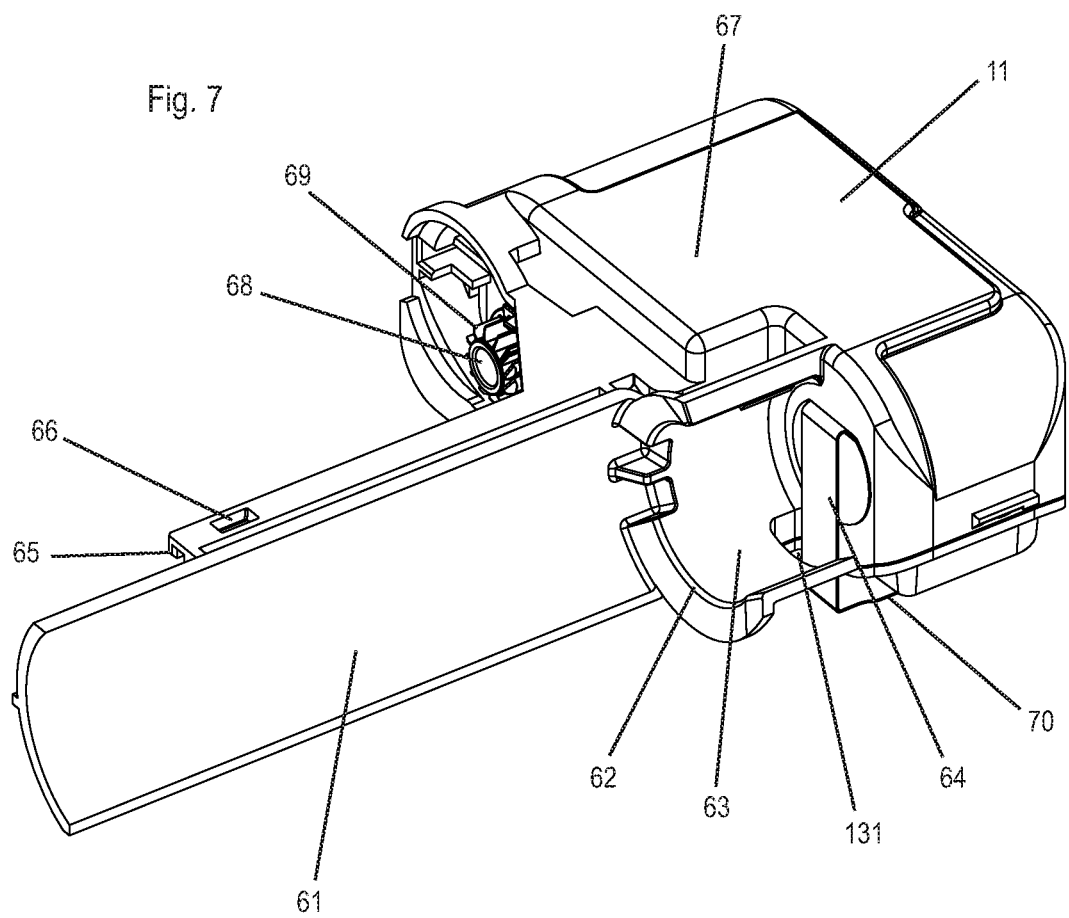
FIG. 7: A needle unit NU of the injection device.

In FIG. 7, the needle unit NU (11) includes a cartridge holder (61) adapted to receive the cartridge unit (12) (see e.g., FIG. 2) whereby a neck of the cartridge holder engages the abutment surface (62) of the cartridge holder (61) to axially position the cartridge unit (12) in the cartridge holder (61). A distal end of the cartridge unit (12) is receivable in the receiving section (63) of the cartridge holder. The housing (67) is closed by a sterile barrier film (64) that is attached to the housing (67) and covers a passage for a cartridge needle. The sterile barrier film (64) has a pull tab (70) that is guided through a notch (131) or an aperture located between the needle housing (67) and the cartridge holder (61) to an outside surface, for example a surface of the release liner (6) of the injection device (1). A rotatable cam shaft (68) having a gear wheel (69) located outside of the needle unit (11) is available for driving the components located inside the needle unit (11). The passage of the cam-shaft (68) is sealed to form a tight barrier (for example using an O-ring) that prevents contamination from outside the needle unit via the cam-shaft surface to the inside of the needle unit (11). The needle unit (11) can be attached or coupled to the drive unit (10) using keys (65) that match corresponding keyways on the drive unit (10) for instance to establish a fixed connection, e.g., a non-reversible connection, using locking aperture (66) of the needle unit (11) that is engagable with a corresponding sloped protrusion on the drive unit (10).

Figure 8A:
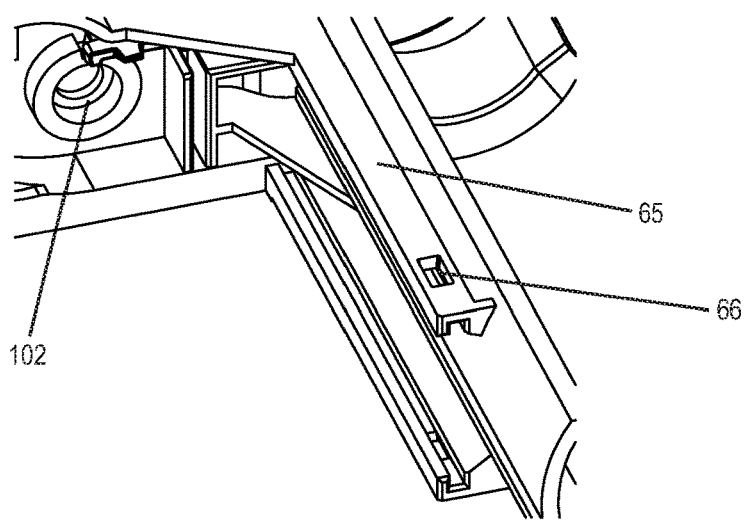
FIGS. 8a-8r: The individual components of the needle unit NU.
Figure 8B:
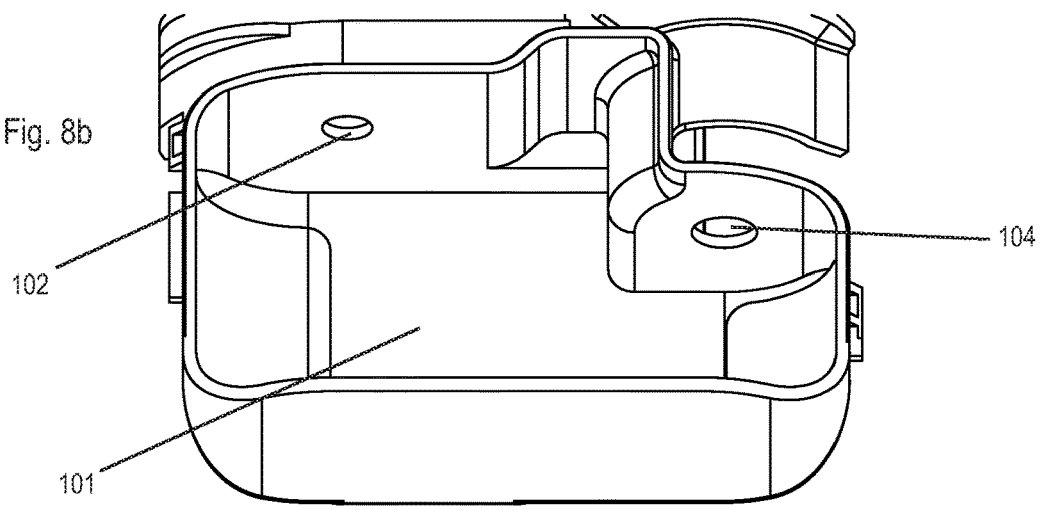
FIG. 8s: An exploded view showing all components of the needle unit NU.
Figure 8C:
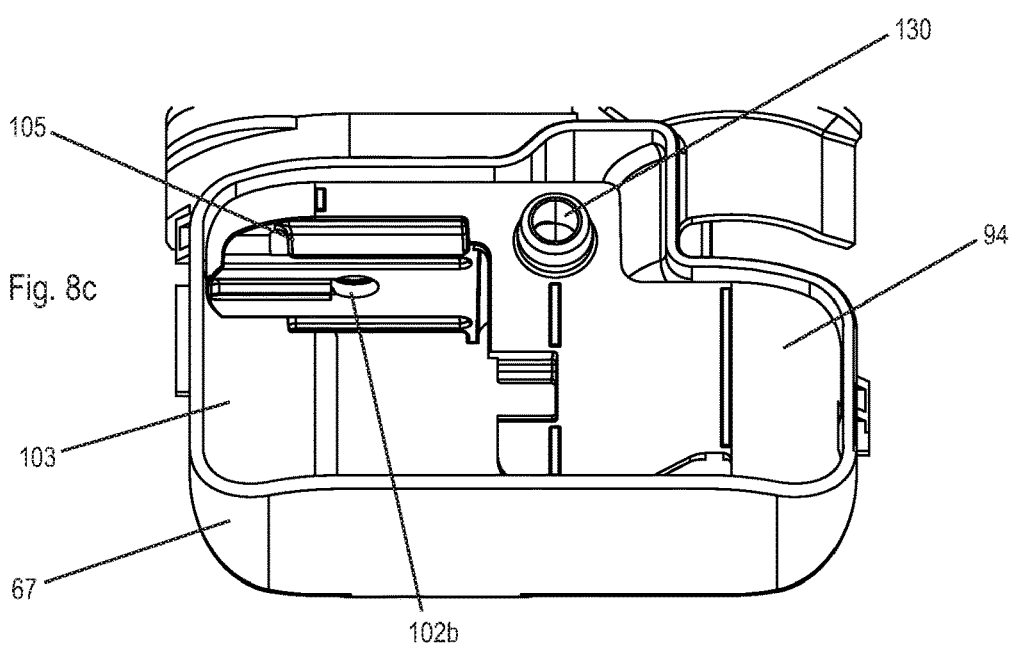
Figure 8D:
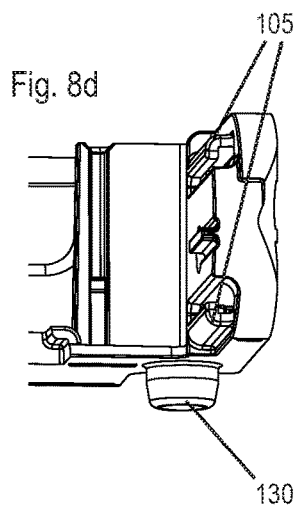
Figure 8E:
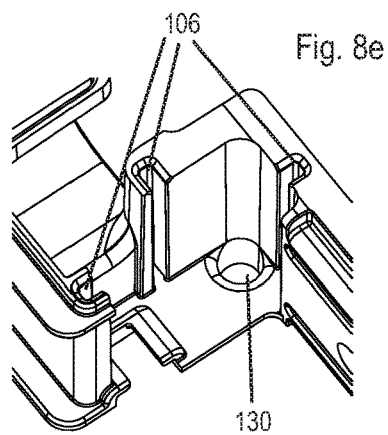
Figure 8F:
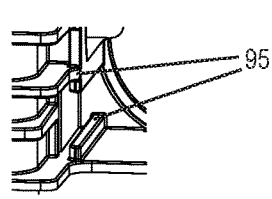
Figure 8G:
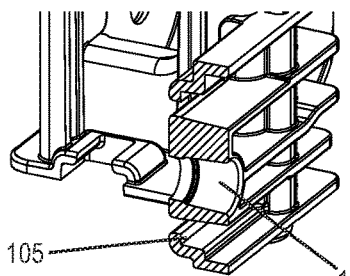
Figure 8H:
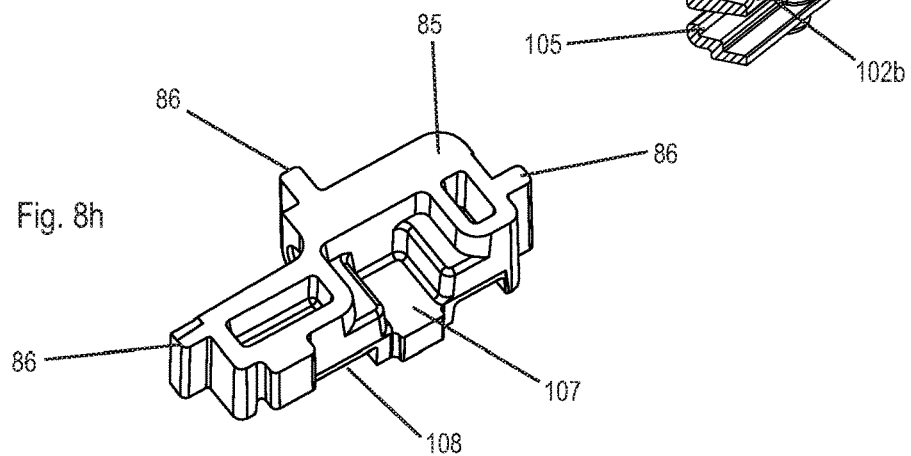
Figure 8I:
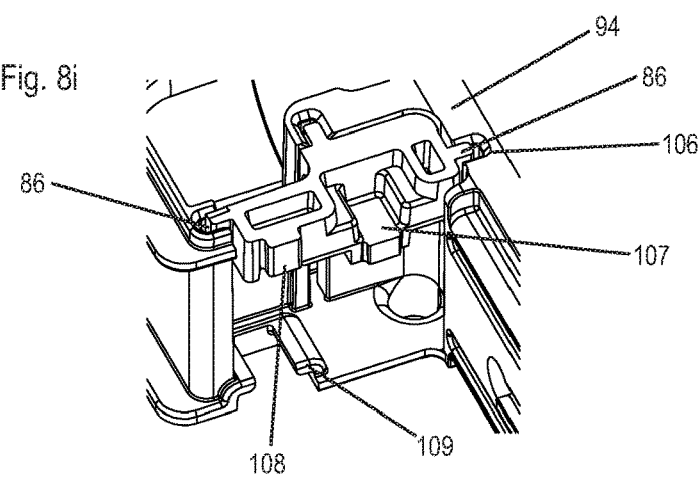
Figure 8N:
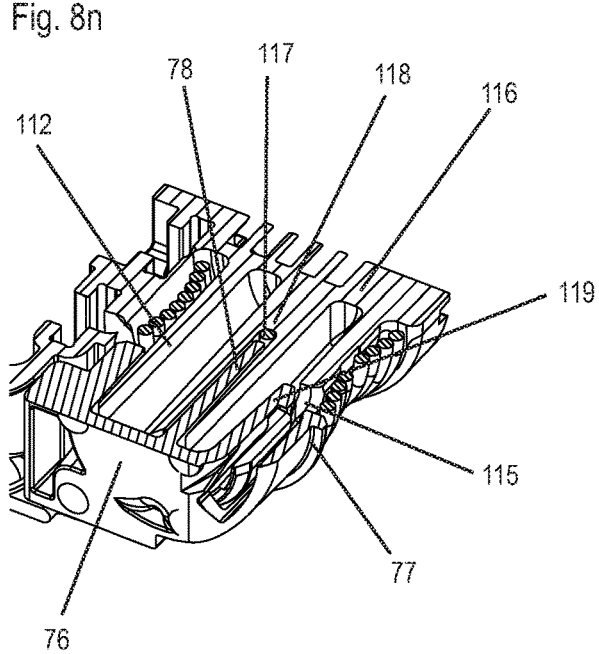
Figure 8O:
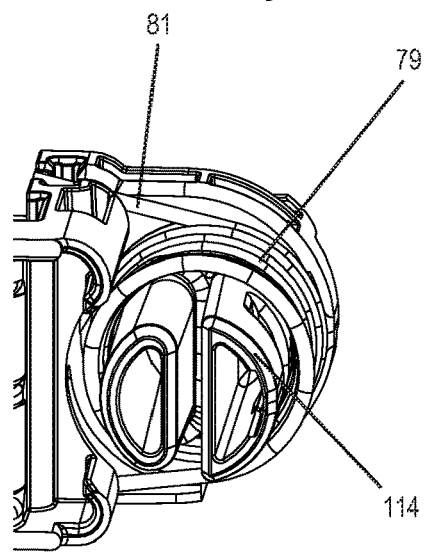
Figure 8P:
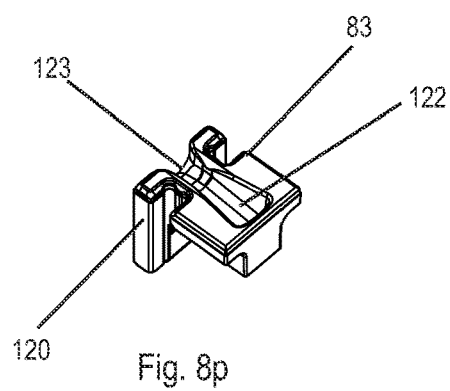
Figure 8Q:
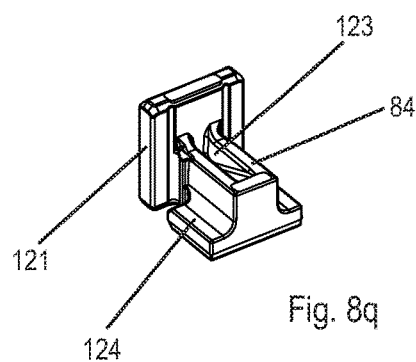
Figure 8R:
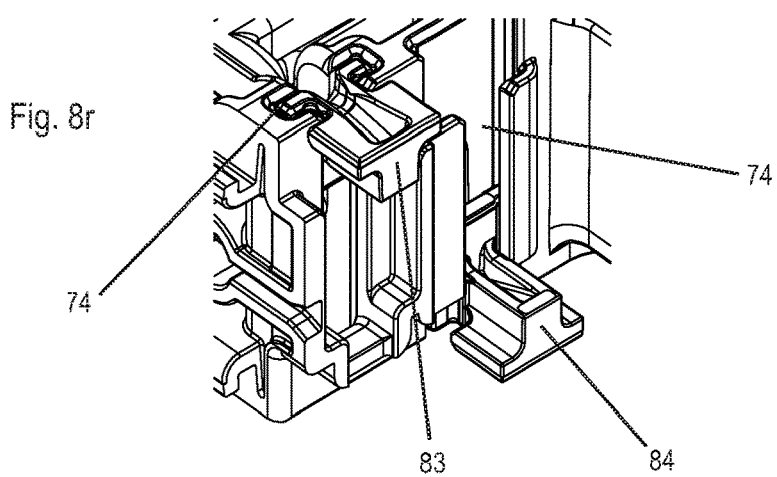
Figure 8S:
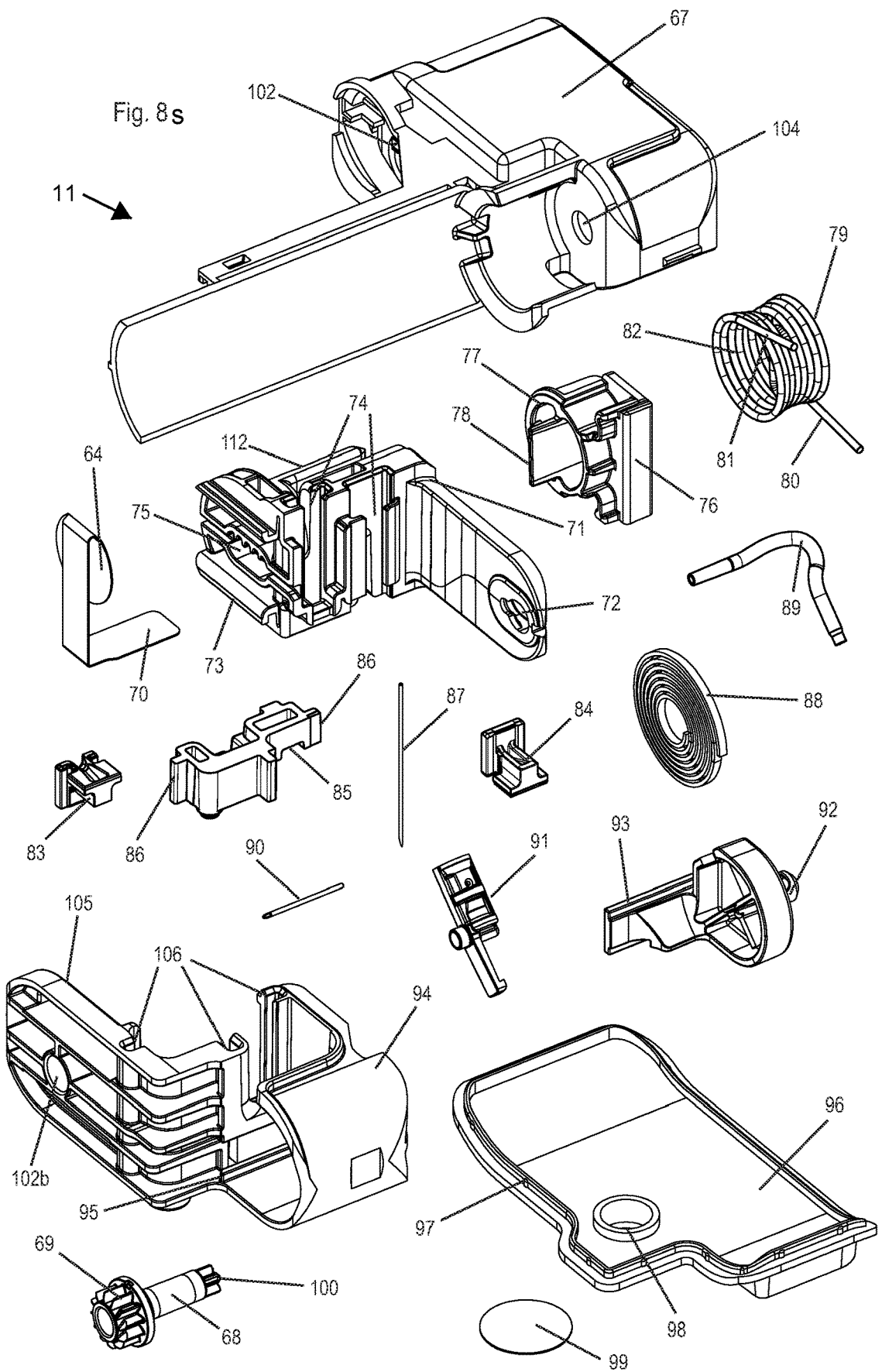

An exploded view with the components forming the needle unit (11) is shown in FIG. 8*s*, and the needle unit (11) comprises a needle housing (67) enclosing a fluid path and the components for the needle insertion and retraction mechanism. The needle housing (67) is part of the enclosure forming a sterile barrier preventing contamination of the fluid path, and passages (102, 104, 98) in the needle housing need to be sealed or covered accordingly. The passage (104) for a cartridge needle (90) is covered by a sterile barrier film (64) that may be removed from the needle housing (67) using a pull tab (70) guided to the outside or an outside surface of the injection device (1).

The needle housing (67) comprises a mechanism holder (94) which provides structural support to a slider (71), a skin piercing needle holder (85), a cartridge needle slider (92) and the cam shaft (68). The mechanism holder (94) is a separate part of the needle housing (67) but functionally behaves as an integrated part of the needle housing (67).

The slider (71) may move parallel to the bottom surface of the housing unit (2) between discrete lateral positions and the movement may be controlled by the PCB unit (9) and driven by the drive unit (10). The lateral movement is guided by linear keys (73) that engage linear guidances (105) of the mechanism holder (94). The slider (71) comprises a gear rack (75) for driving the slider in the lateral direction by a cam shaft (68) that is coupled to the gear mechanism (46,39,40,35) of the drive unit (10). The slider (71) comprises linear guidances (74) that engage spring sliders (83, 84), the linear guidances are oriented perpendicular to the movement direction of the slider, or, in other words, parallel to the skin piercing needle insertion direction. Furthermore, the slider has an extension comprising a locking fork (72) which holds a cartridge needle slider (92) in a retracted position.

The slider (71) comprises a spring holder (112, see FIG. 8*k*) for holding a torsional spring (79), thus the torsional spring (79) follows the lateral movements of the slider (71). The torsional spring (79) is fixed after insertion into the spring holder using a spring fixator (76). The torsional spring (79) has an upper leg (81) and a lower leg (80) connected by a coil (82). The coil (82) biases the two legs towards each other when the torsional spring is assembled in the needle unit (11). The coil (82) has a connecting bar (117) connecting two parts of the coil spring that ensure that the two legs are biased towards each other when tensioned (FIG. 8*m*). The upper leg (81) biases an upper spring slider (83) and the lower leg (80) biases a lower spring slider (84) as will be described in detail below. The connecting bar (117) is configured to be inserted into a receiving pocket (113) of the spring holder (112) and the coil (79) surrounds the spring holder (112).

The mechanism holder (94) supports a skin piercing needle holder (85) and has linear guidances (106) to guide the skin piercing needle holder (85) for moving perpendicular to the bottom surface of the housing unit (2) of the injection device. The skin piercing needle holder (85) has a plurality of keys (86) that engage the linear guidances (106) of the mechanism holder (94) for guiding the skin piercing needle holder (85) from a needle retracted to an inserted position and from the inserted position back to the retracted position. The skin piercing needle holder (85) is driven by the torsional spring (79) between those two positions using the two legs (80, 81). The skin piercing needle holder (85) holds the skin piercing needle (87) which is a hollow steel needle that is fluid tight sealed into the holder (85), for example using a rigid or flexible glue. The skin piercing needle holder (85) comprises a passage connecting the needle to an outlet in the holder adapted to receive a tube (89).

The tube (89) provides a fluid conduit between the skin piercing needle (87) and a cartridge needle (90). The cartridge needle (90) is inserted and attached (for example using an adhesive connection) to a cartridge needle holder (91) which provides mechanical support to the cartridge needle (91) and connects the needle to the tube (89). The cartridge needle holder (91) may be an integrated part of, or inserted into a cartridge needle slider (92). The cartridge needle slider (92) has guidances (93) which engage keyways (95) of the mechanic holder (94) that allow for axial movement of the cartridge needle slider (92) parallel to the bottom of the injection device. The lateral movement of the slider (71) may be perpendicular to the movement of the cartridge needle slider (92). The cartridge needle (90) can be moved from a retracted position inside the needle unit (11) to an extended position outside the needle unit (11) thereby passing through the passage (104), such as after removing the sterile barrier (64). The cartridge needle (90) is may be a hollow steel needle with a sharp tip that is open, or alternatively the steel needle is a pencil tip needle with a closed tip and a lateral opening. Optionally, plastic needles or spikes may be used.

The needle unit (11) further comprises a cam shaft (68) comprising a gear wheel (100) for the gear rack (75) that is located on the slider (71) inside the needle housing (67), and a gear wheel (69) located outside the needle unit and configured for engaging the gear mechanism of the drive unit (10). The cam-shaft (68) is rotatably received by the passage (102) of the needle housing (67) and a corresponding passage (102*b*) in the mechanism holder (94). A seal is present between the cam shaft (68) and the needle housing (67) and/or the mechanism holder (94), to prevent contamination of the fluid path enclosed by the needle housing (67). Such a seal may comprise an elastic element such as an O-ring surrounding the cam shaft (68) and being in a press-fit engagement with a housing part.

The needle housing (67) has an opening or fluid path compartment (101, FIG. 8*b*) that is closed by a needle cover (96) which encloses the fluid path after insertion and mounting of all components into the fluid path compartment (101). The needle cover (96) has a sealing rim (96) which may be fixated in a corresponding recess of the needle housing (67) to form a tight seal preventing contamination of the fluid path compartment (101). The needle cover (96) may be made from a plastic material that is welded, for example laser welded or ultrasonic welded onto the needle housing (67). The needle cover (67) comprises an aperture (98) for the skin piercing needle (87) which is closed by a sterile barrier film (99). The sterile barrier films (99, 64) may be made from a porous membrane allowing for chemical sterilization techniques such as gas plasma or ETO sterilization. An example is a non-woven polyethylene fiber membrane, such as the Tyvek® membrane.

Details of the components forming the needle unit (11) will be described in FIGS. 8*a* to 8*r*. A detail of the key (65) and the locking aperture (66) of the needle unit (67) is shown in FIG. 8*a*. The key (65) may engage a connecting ridge (189) that is part of the drive unit (10) (FIG. 5*h*) and once the locking aperture (66) engages the locking protrusion (190), then the drive unit (10) and needle unit (11) are may be fixedly attached to another (e.g., locked together irreversibly). The fluid path compartment (101) that provides part of the sterile enclosure for the fluid path is shown in FIG. 8*b*. The apertures (102, 104) for the cam shaft (68) and cartridge needle (90) are part of wall sections oriented perpendicular to the bottom surface of the fluid path compartment (101). The passage for the cam shaft (68) on the outside surface of the wall section has a protruding rim for mechanical support and/or fixation of the sealing element as can be seen in FIG. 8*a*. The mechanism holder (94) fits into the fluid path compartment (101), such as by press-fit or by another locking means such as a snapper or by an adhesive connection. See FIG. 8*c*, which represents a view from the below of the device showing the aperture for the skin piercing needle (130). The passage for the cam shaft (102*b*) in the mechanism holder (94) is aligned with the passage (102) of the needle housing (67) and a compartment (103) is available for the slider (71) to move laterally as the slider is guided by the guidances (105) of the mechanism holder (94), see also FIG. 8*d* (representing a view from the side of the mechanism holder). The linear guidances (106) for engaging the skin piercing needle holder (85) is shown from the top of the mechanism holder in FIG. 8*e* whereas details for the keyways (95) guiding the cartridge needle slider and details of the passage for the cam shaft (102*b*) can be seen in cross sections in FIGS. 8*f* and 8*g*, respectively.

The skin piercing needle holder (85) comprises next to the linear keys (86) receiving sections (107, 108) for the upper spring slider (83) and the lower spring slider (84). The key-keyway engagement (86, 106) guides the skin piercing needle holder (85) in the mechanism holder (94) such that the skin piercing needle (85) holder can only move in the needle insertion direction. The receiving sections (107, 108) of the skin piercing needle holder (85) have an engagement surface for the spring sliders such that forces from the legs of the torsional spring (79) may be transferred to the skin piercing needle holder (85) while the spring sliders (83, 84) can move on the engagement surface in a direction that is perpendicular to the skin piercing needle insertion direction. The assembly of the mechanism holder (94) and the skin piercing needle holder (85) is shown in FIG. 8*i*, with the skin piercing needle holder (85) in the needle retracted position.

The slider (71) comprises the linear keys (73) for engaging the mechanism holder (94), and two linear guidances (74) for engaging the spring sliders (83, 84). The slider further comprises a stop surface (111) that is adapted to abut a surface, such as a bottom surface, of the skin piercing needle holder (85) for keeping the skin piercing needle holder (85) in a retracted position. The slider (71) comprises a gear rack (75) having gear teeth (110) that may engage the gear wheel (110) of the cam shaft. The linear guidances together with the gear rack—gear wheel interaction (75, 110) ensure that the slider can move in the lateral direction (FIG. 8j). A top view of a section of the slider (71) showing the two linear guidances (74) that may engage the spring sliders (83, 84) is shown in FIG. 8l. The spring sliders (83, 84) are keyed to the slider (71) such that they can move up and down in the guidance (74) while they have to follow the lateral movement of the slider (71). A spring holder (112) is attached to, and protrudes from a base (116) of the slider (71) (see e.g., FIGS. 8k and 8n). The spring holder (112) has a circular outer shape that is split apart by a receiving pocket (113) and further comprises a cut-out (115) that is configured for attaching the spring fixator (76) thereto. The receiving pocket receives and rotationally fixates the bridging bar (117) of the torsional spring (79) to the slider (71). Furthermore the receiving pocket (113) together with the connecting bar provides the counterbalance for the two legs of the spring when tensioned. Thus the lateral movement of the slider (71) will be followed by the torsional spring (79) with the upper and lower spring legs (84, 85), by the upper and lower spring sliders (83, 84) and by the locking fork (72).

The assembly of the torsional spring (79) onto the spring holder (112) is shown in FIGS. 8n and 8o. First the coil spring (79) is mounted onto the spring holder (112) whereby the bridging bar (117) of the torsional spring (79) is inserted into the receiving pocket (113) of the spring holder (112). The bridging bar (117) abuts a surface (118) of the slider (71) and the spring fixator (76) is mounted onto the end section (114) of the spring holder (112) whereby a wing (78) of the spring fixator (76) fits into the receiving pocket (113) and pushes the bridging bar (117) towards the abutment surface (118) of the slider (71). The spring fixator (76) has a flexible arm with a protrusion that snap fits into the cut-out (115) of the spring holder (112) and locks the torsional spring (79) to the slider (71).

The upper spring slider (83) and the lower spring slider (84) are shown in FIGS. 8p and 8q, respectively. The upper spring slider (83) comprises a key (120) that engages the linear guidance (74) of the slider (71). Furthermore the slider (71) has an opening (123) for receiving the upper leg (81) of the torsional spring (79) into a receiving section (122) of the upper slider (83). The lower spring slider (84) may be identical to the upper spring slider (83) but oriented upside down and showing a holding surface (124) which is intended to engage a locking member (109) present on the mechanism holder (94). The assembly of the upper and lower spring sliders engaging the linear guidances (74) of the slider (71) is shown in FIG. 8r.

The tube or conduit (89) connecting the skin piercing needle holder (85) to the cartridge needle holder (91) is shown in FIG. 9. The ends of the tube (89) are inserted into the holders (85, 91) and a fluid tight connection established by a press-fit of the elastic tube material, or the ends are adhesively connected to the holders. The cartridge needle holder (91) has a locking feature (125), for example a locking arm or a snapper that may engage the cartridge needle slider (92). A detail of the cartridge needle slider (92) is shown in cross sectional view of FIG. 11. The cartridge needle slider (92) is engaged with the mechanism holder (94) through the key-keyway engagement (95, 93, FIGS. 8, 8f) and can move from a retracted position to an extended position parallel to the bottom surface of the device. The cartridge needle slider spring (88) (see e.g., FIGS. 10 and 11) is positioned and compressed between the mechanism holder (94) and the cartridge needle slider (92) thereby biasing the slider (71) to move towards the inserted position. The cartridge needle slider (92) is retained in the retracted position by a knob (126) of the cartridge needle slider (92) which engages a locking fork (72) of the slider (71). Once the slider (71) is moved in a lateral direction, such as from a starting position to an intermediate position, then the engagement between the fork (72) and the knob (126) may be released and the cartridge needle slider (92) moves together with the cartridge needle (90), the cartridge needle holder (91) and the end of the flexible tube (89) towards the passage (104) of the fluid path compartment. The cartridge needle (90) may at least partially extend through the passage for penetrating a septum of the cartridge unit (12). A detailed view of the cartridge needle slider spring (88) is shown in FIG. 10. The spring (88) may be a tapered coil spring having the advantage of a space saving arrangement when the spring (88) is compressed as the coil sections do not abut each other when compressed.

Figure 13:
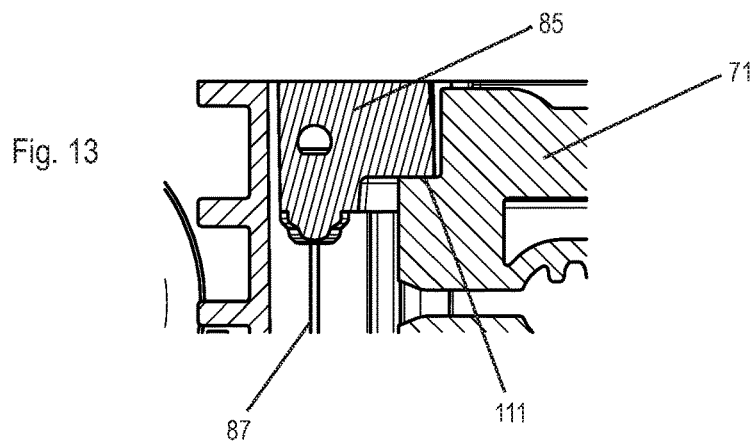
FIG. 13: Detail of the skin piercing needle holder abutting the slider maintaining the holder in the retracted position.

The assembled needle insertion and retraction mechanism and the fluid path is shown in FIG. 12. The slider (71) is in the starting position and can move due to rotation of the cam shaft (68) in the lateral direction as the slider (71) is guided by the mechanism holder (94). The upper leg (81) of the torsional spring (79) presses onto the upper spring slider (83) which itself presses onto the receiving section (107) of the skin piercing needle holder (85). The skin piercing needle holder (85) is kept in the retracted position against the bias of the spring force as will be explained in FIG. 13. The torsional spring (79) is locked to the slider (71) by the spring fixator (76) and the locking fork (72) engages the knob (126) of the cartridge needle slider (92). The skin piercing needle holder (85) is kept in the retracted position when the slider (71) is in the starting position due to the stop surface (111) of the slider (71) abutting the lower surface of the skin piercing needle holder (85), FIG. 13.

Figures 14, 15:
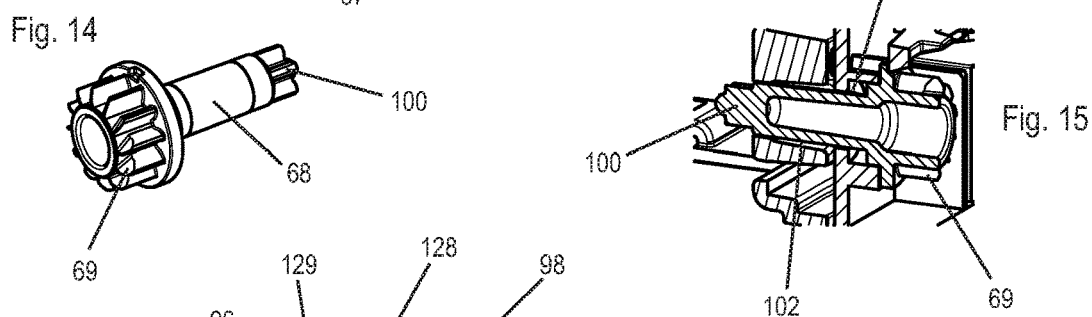
FIG. 14: A cam shaft of the needle unit NU.
FIG. 15: The cam shaft in a passage of the needle unit NU.
Figure 16A:
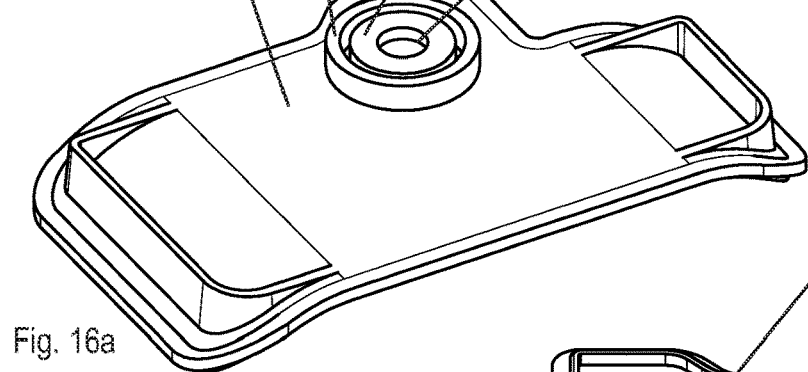
FIGS. 16a, 16b: A needle cover for needle unit NU.
Figure 16B:
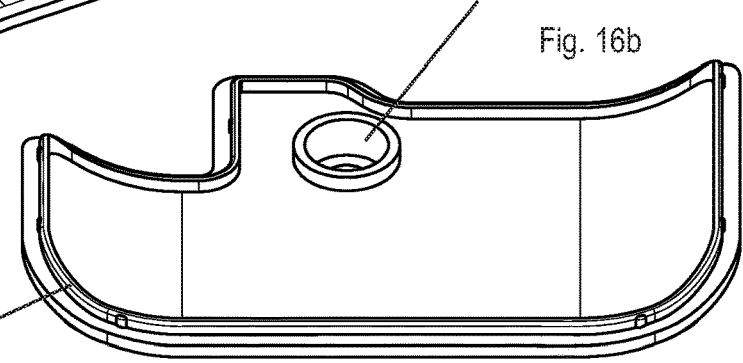
Figure 17:
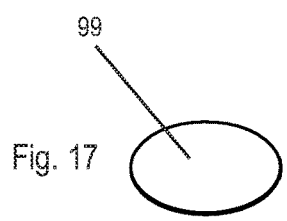
FIG. 17: A sterile barrier film.
Figure 18:
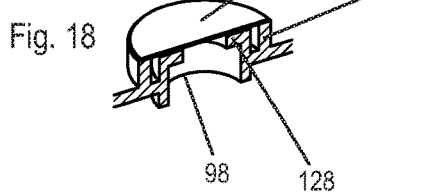
FIG. 18: The sterile barrier film covering aperture skin piercing needle in needle cover of the injection device.
Figure 22:
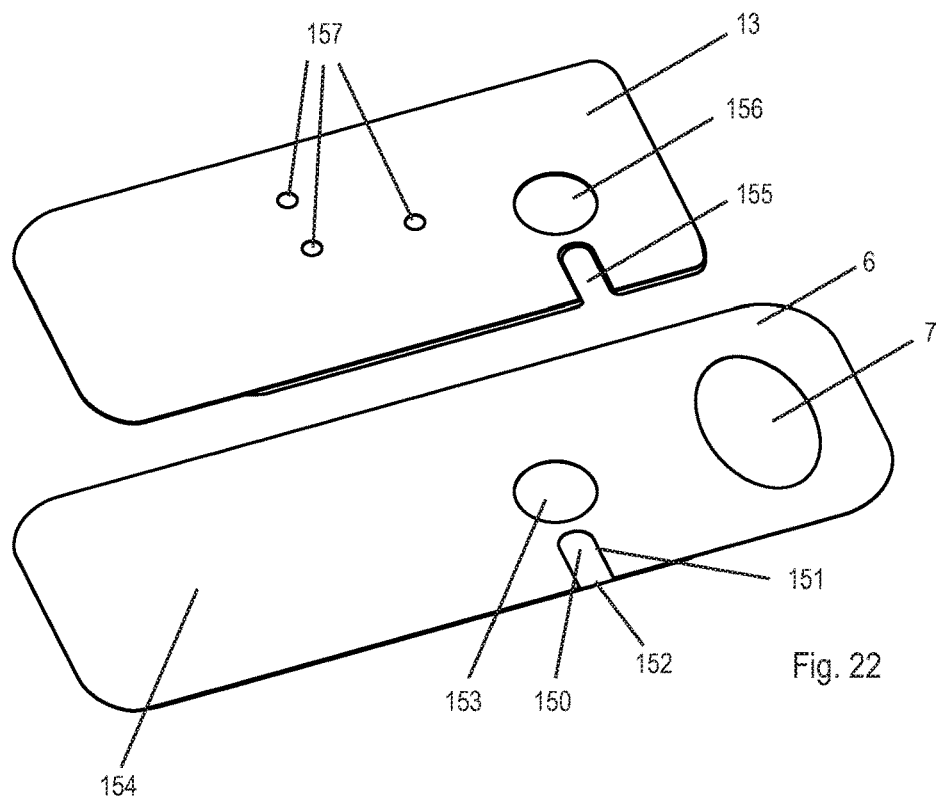
FIG. 22: Components of a sensing patch unit SU of the injection device.

Details of the cam shaft (68) with the two gear wheels (69, 100) at each end is shown in FIG. 14, and a cross section of the cam shaft extending through the passages (102, 102b) of the needle housing and the mechanism holder is shown in FIG. 15. The gear wheel (69) at one end of the cam shaft (68) is located within the interior of the (sterile) fluid path compartment (101), whereas the gear wheel (100) at the other end is located outside of the needle housing (non-sterile). An O-ring forms a seal between the housing and the cam shaft (68) preventing contamination of a sterile fluid path compartment (101) and providing a frictional resistance for rotating the cam shaft (68). The needle cover (96) comprising the aperture (98) for the skin piercing needle is shown in FIG. 16b. The outside surface of the needle cover (96) (FIG. 16a) has a sealing surface (128) and a circumferential rim (129) that surrounds the aperture (98) and sealing surface. The barrier film (99) may be attached to the sealing surface (128) only and not to the rim (129). The rim (129) may act as a support for attaching the surface of the barrier film (99) (FIG. 17) to an adhesive layer, for example a strengthening film or to the release liner (6) itself. During removal of the sterile film (99), either using the release liner or via the strengthening film, then the film (99) is not attached to the circumferential rim (129) as this will facilitate the roll-off or peel-off of the sterile film (99) from the sealing surface (128) (see e.g., FIG. 18).

The assembled cartridge unit (12) is shown in FIG. 19 and a detailed view of the individual parts in FIG. 20. The cartridge unit (12) comprises a barrel (132) which is a hollow cylinder having a distal opening (133) and a proximal opening (134). At the distal end, the barrel has a neck (135) area with a lower diameter compared to the proximal barrel section. The distal opening (133) is closed by a pierceable septum (141) which is attached to the neck using a crimp cap (139). The crimp cap has an opening that is available for a needle or spike for penetrating the septum (141). A sterile barrier film (136) may be connected to an end wall of the crimp cap thereby covering the opening of the crimp cap and the septum's surface underneath. The sterile barrier film (136) may be glued, welded, heat welded or otherwise sealed to the surface of the crimp cap thereby forming a protective layer for the surface of the septum. The connection between the crimp cap and the sterile barrier film (136) is such that the film may be removed easily while still providing a tight seal between the film and the cap. The sterile barrier film (136) may be a film made from porous non-woven fibers and the porosity allows for chemical sterilization agents to pass through. The sterile barrier film (136) has a pull tab (137) which is an integral part of the porous film or a separate film connected to the sterile barrier film (136). The pull-tab (137) may be guided to the outside or an outside surface of the injection device such that the barrier film may be removed by pulling the tab. The sterile barrier film (136) and/or the pull tab (137) may be folded to promote the peel-off, or roll-off, of the sterile barrier film (136) from the crimp cap. The sterile barrier film (136) and/or pull tab (137) may be guided around pins or wheels within the housing unit (2) to facilitate film removal, for example using a pulley system.

The cartridge unit (12) may comprise a flip-off cap (138) covering the sterile barrier film (136). The flip-off cap (138) may be attached to the crimp (139). The flip-off cap (138) protects the sterile barrier film (136) during handling of the cartridge unit (12) and the cap may be removed just prior to inserting the cartridge unit (12) into the housing unit (2) of the injection device (1). The flip-off cap (138) may have openings to enable sterilization of the sterile barrier film (136) and the septum's surface and/or penetration of a needle. The flip-off-cap (138) may be made from a plastic material and attached to the crimp cap (139) using heat welding, laser welding or ultrasonic welding. The crimp cap (139) may be constructed from a metal such as aluminum. Furthermore, the flip-off cap (138) may have perforated sections forming predetermined breaking points for easy flip-off cap removal. The parts of the flip-off cap remaining on the crimp cap may be used to correctly position the cartridge unit (12) in the housing unit (2), for example the angular position.

A plunger (140) is moveably positioned within the proximal opening (134) of the barrel (132) of the cartridge unit (12) thereby forming a sealing for the medicament that is enclosed in the cartridge. The plunger may be moved by the piston rod (31) of the drive unit (10) during medicament delivery. The plunger may be placed at different axial positions in the barrel for cartridges having different fill volumes of the medicament. It may be beneficial to have the piston rod (31) at a fixed starting position (or retracted position) and compensate the gap between the end of the piston rod (31) and the proximal end of the plunger (140) using a spacer (142). The spacer (142) compensates for the gap and is beneficial for a homogeneous distribution of the forces from the piston rod to the plunger (140). Optionally, a pivot bearing (143, 50) is formed between the protrusion (50) on the distal end of the last segment of the piston rod (31) and a bearing surface (143) present on a proximal surface of the spacer (142). The bearing surface (143) may be a recessed section matching a ball shaped protrusion on the end of the piston rod to form a ball in a socket bearing. Alternatively one of the two surfaces is flat and abutting a ball shaped protrusion for a ball on plate bearing.

FIG. 21 shows a detailed view of the flip-off cap (138), the crimp cap (139) and the sterile barrier film (136). The crimp cap has an end surface (148) with an aperture (149) for the cartridge needle. The end surface (148) is used for attaching the sterile barrier film (136) to the crimp cap. The surface (148) may be heat treated, etched, roughened or coated with an adhesion promotor to enhance the connection between the sterile barrier film and the crimp cap. The flip-off cap (138) comprises connectors (146) for connecting to the crimp cap (139) and predetermined breaking points (147) facilitate the controlled release of the flip-off cap from the cartridge unit (12). The sterile barrier film (136) may have an internal fold (145) that is located inside the housing and the pull tab (137) may have an external fold (144) located outside the housing when the device is assembled.

Figure 23:
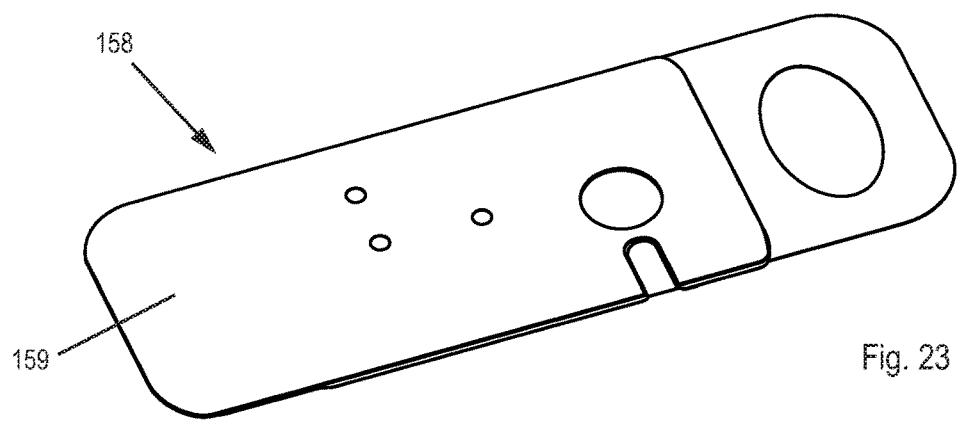
FIG. 23: The sensing patch unit assembled with a release liner of the injection device.
Figure 24:
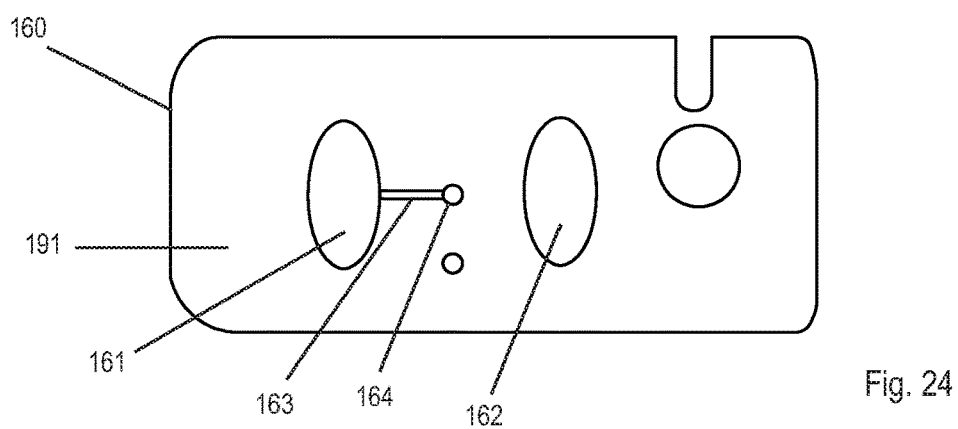
FIG. 24: A sensor layer in a sensing patch of the injection device.

A detailed view of the sensing patch unit (13) is shown in FIGS. 22 to 25. The sensing patch unit (13) comprises an aperture fully enclosed by the film-shaped unit, for example a circular aperture (156) in the film, that is available for the skin piercing needle (87). Furthermore the sensing patch unit (13) has an opening, or at least semi open aperture, such as a notch shaped opening (155) located at a rim of the film-shaped unit, that is available for inserting the sterile barrier films from the needle unit (11) and/or the cartridge unit (12). The sensing patch unit (13) further comprises contact points (157) located in the top surface that may contact the contact springs (29) for connecting the sensing patch unit to the printed circuit board unit (9). The release liner (6) for the sensing patch unit (13) may comprise a conductive layer (154) that at least partially covers one or both of the surfaces of the release liner. The conductive layer (154) may be a coated or a printed metal layer on top of a polymeric sheet of material forming the base for the release liner. Examples are a silver ink layer or an aluminum or gold layer deposited onto the surface. Alternatively a non-metallic coating may be used, for example a carbon black coating. The release liner has an aperture (153) for the skin piercing needle (87) that is aligned with the aperture (156) of the sensing patch unit (13). The release liner (6) has a notch (150) that is located at a rim of the release liner and aligned with the notch (155) of the sensing patch unit (13) such that the sterile barrier films may pass through the sensing patch unit (13) and the release liner (6). The notch (150) has an opening (152) located at an edge of the release liner and the notch may have two legs that start at the opening (152) to form a U-shaped notch. The assembly (158) of the sensing patch unit (13) and the release liner (6) is shown in FIG. 23, an adhesive top layer (159) facing the housing unit (2) comprises an adhesive for attachment to the device. The sensing patch unit (13) comprises at least one sensor layer (160) that is located between the adhesive layer (159) connecting the patch to the housing and the release liner (6) (FIG. 24). The sensor layer (160) comprises a sensor area (161) that is connected to contact (164) using electrically conductive leads (163). The contact (164) is connected to one of the contacts (157) present in the top layer (see FIG. 22) such that signals can be transmitted from and to the sensor (161) via the contact springs (29). The sensor layer (160) may have at least one second sensor area (162) that is connected via a separate lead that is not shown to the contact springs. The sensor area (161) and second sensor area (162) each form a capacitive sensor where each capacitance depends on the dielectric present adjacent to the sensors (skin or air) and/or the presence of an electrical shielding that may be present in the release liner (6). The latter enables the detection of the release liner removal. The sensing patch unit (13) may further comprise additional sensor areas and/or sensor layers and grounding layers present between the several layers to reduce the signal to noise ratio and improve the accuracy of the capacitive measurements. Furthermore isolation layers may be present between two layers having conductive leads.

The sensor layer may have one sensor area (161) only.

The sensing patch unit (13) further comprises a skin adhesive layer (191) that is adjacent to the release liner. The skin adhesive layer (191) is the outermost layer of the sensing patch unit when the sensing patch unit is attached to the housing using the adhesive top layer (159).

Figure 25:
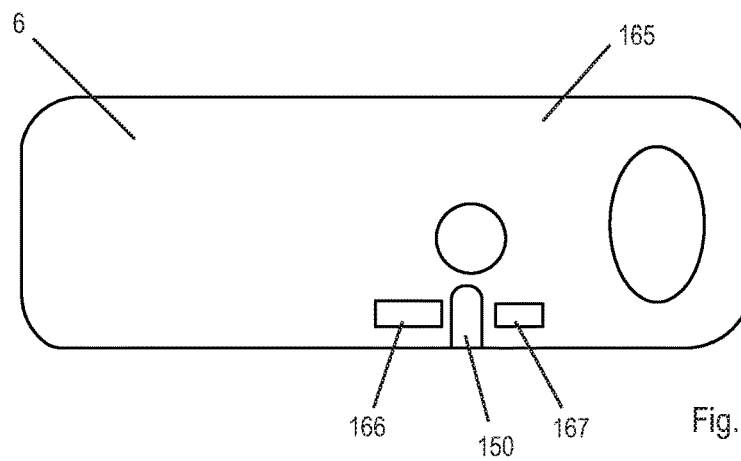
FIG. 25: A bottom view of the release liner prior to attachment to the skin adhesive layer.
Figure 26:
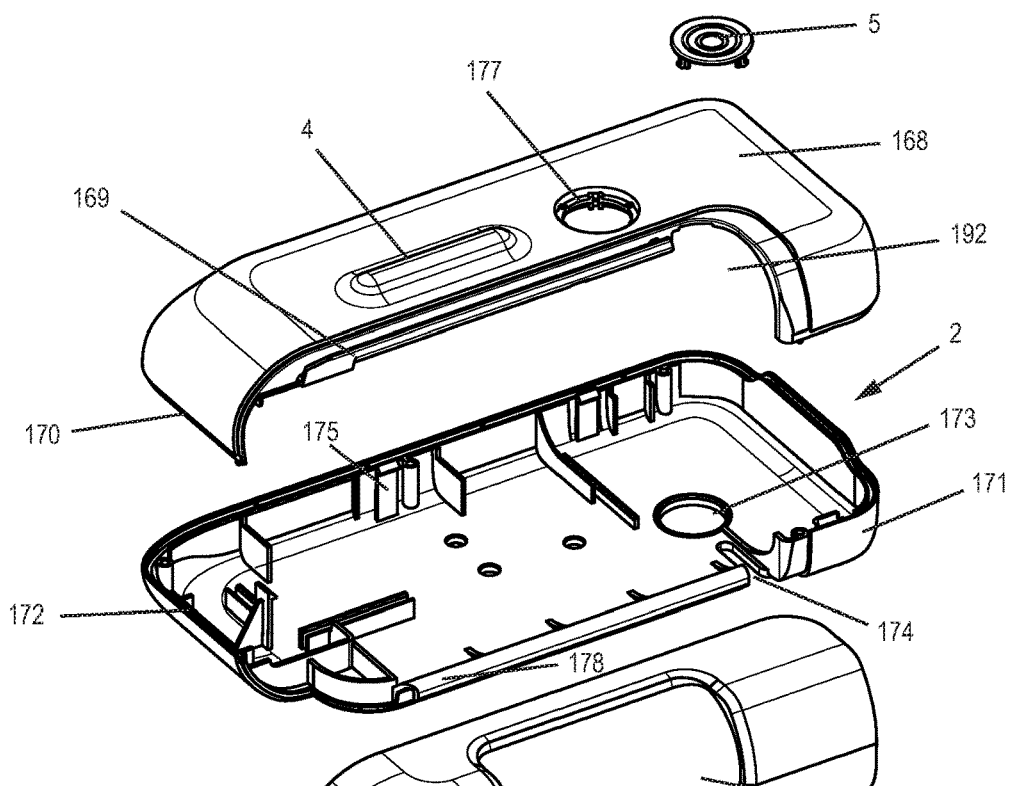
FIG. 26: An exploded view of a housing unit HU of the injection device.

A bottom view of the release liner (6) is shown in FIG. 25. The backside surface (165) that is not in contact with the skin adhesive layer (191) comprises adhesive or connecting spots (166, 167) that are each located adjacent from the notch (150) in the release liner. The adhesive spots are arranged to allow for attaching one or both of the sterile barrier films (64, 136) from the needle unit and/or the cartridge unit to the release liner's backside surface. The spots may be opposite to another to ensure that both ends of the sterile barrier films (for example the ends of the pull tabs) are each connected to one side facing the notch for an even stress distribution upon release liner removal. The adhesive spots may comprise double sided adhesive tape, a hot melt or a spot that is prepared for gluing the ends of the films (or pull tabs) to the backside surface (165) of the release liner. The surface of the release liner may be treated (roughened, etched, heat treated or coated with an adhesion promotor) to enhance the attachment between the release liner and the sterile barrier films, The housing unit (2) is shown in FIG. 26 and comprises a housing cover (168) forming the top surface of the injection device. The housing cover (168) comprises the indicator (4) which may be an elevated and semi-transparent section of the housing cover (16) such that underlying LED lights can shine through the indicator for showing a status of the device or of the injection procedure. The housing cover (168) has an aperture (177) shaped to receive and hold the push button (5). The housing cover further comprises a guiding rib (169) for guiding the cover (8) of the housing unit during device assembly. The housing cover (168) is attached to a housing base (171) via a closure rim (170) engaging a matching rim (172) on the housing base. The connection may be an adhesive connection or the two parts may be welded (heat, laser, ultrasonic) together after assembly of the needle unit and drive unit into the housing unit. The housing base (171) comprises support flanges or snappers (175) to engage the drive unit and/or the needle unit, and an aperture (173) for the skin piercing needle. T housing base (171) has guiding rib (178) which forms together with the guiding rib (169) of the housing cover (168) guiding means to guide the cover (8) when closing the housing unit and fixating the cartridge unit in the cartridge holder. The cover (8) has markings (176) printed onto or embossed in the cover (8) such that the user can monitor the fluid level in the cartridge through the viewing window (3). The housing base (171) comprises a notch (174) that is aligned in the assembled device with the notches in the release liner, the sensing patch unit and the needle housing (150, 155, 131) to form a passage for the sterile barrier film from the inside of the housing unit to the outside of the injection device or to an outside surface of the release liner.

Figure 27:
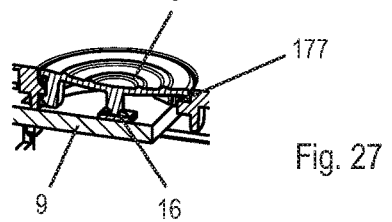
FIG. 27: A detailed view of a push button in the housing unit HU.
Figure 28A:
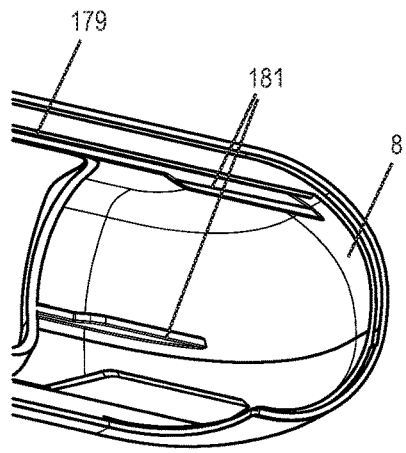
FIGS. 28a, 28b: A cover for the housing unit HU.
Figure 28B:
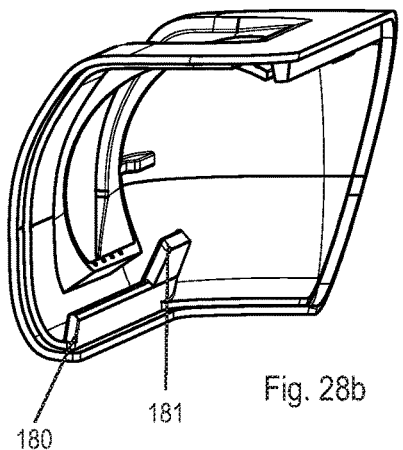
Figure 29:
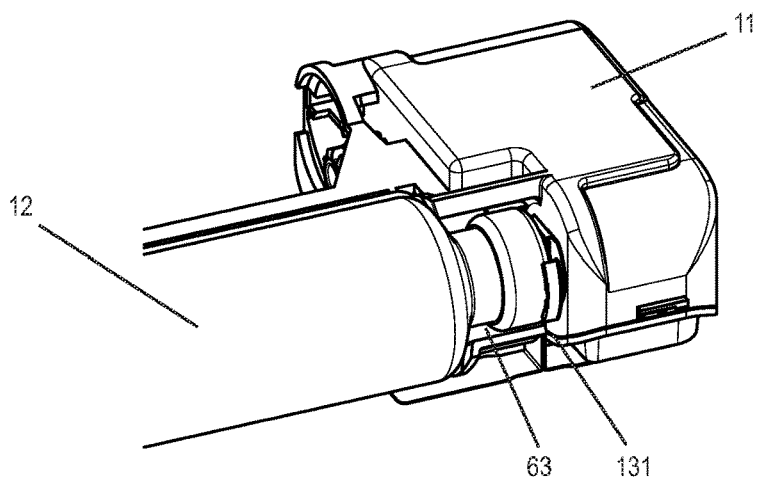
FIG. 29: A cartridge unit CU inserted in the needle unit NU.
Figure 30:
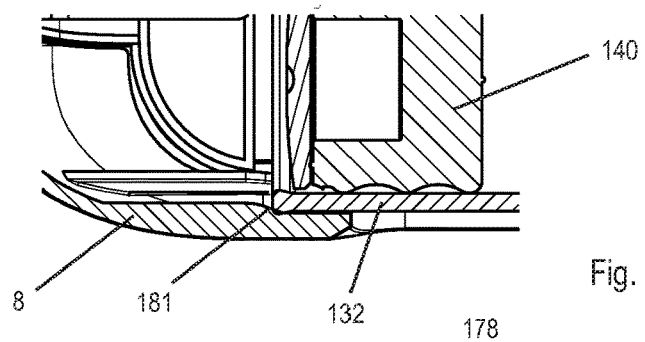
FIG. 30: Detail of a cover of the housing unit HU fixating the cartridge of the cartridge unit CU in the needle unit NU.

A detail of the push button (5) in the assembled device is shown in FIG. 27, showing the aperture (177) in the housing cover and the part of the PCB unit (9) below the aperture having the push button switch (16) contacted by a stem that protrudes from the push button. Once the sensing patch unit (13) detects removal of the release liner (6) or device attachment to the skin, the push button switch is activated such that the injection may be started by pushing the button. Details showing the interior surface of the cover (8) of the housing unit (2) are shown in FIG. 28a and FIG. 28b. A rib or keyway (179) of the cover may engage the guiding rib (169) of the housing cover (168) and another rib or keyway (180) of the cover may engage the guiding rib (178) of the housing base (171), such that the cover (8) may be shifted over the opening (192) in the housing cover. A detail of the needle unit (11) with the cartridge unit (12) inserted into the cartridge holder (61) is shown in FIG. 29. The cover (8) comprises deformable ribs or arresters (181) that engage a rim of the barrel (132) of the cartridge that is located at the proximal opening (134) and thereby fixating the cartridge in the device (FIG. 30).

Figure 31:
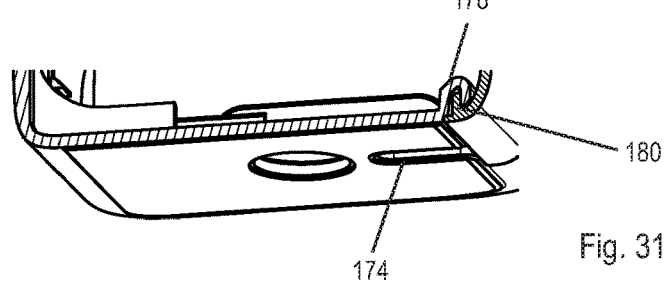
FIG. 31: Detail of the cover of the housing unit HU closing the notch in the housing unit HU.

During assembly, the cartridge unit (12) is inserted in the cartridge holder (61) of the needle unit (11). The sterile membrane (136) and/or the pull tab (137) is inserted into the notch (131) in the needle housing (67), such as from the side, and guided through the notch (174) in the housing base (171), the sensing patch unit (13) and the release liner (6) such that the end of the sterile barrier or the pull tab may be attached to the outside surface of the release liner (6) or is available for the user. The cartridge unit (12) comprising the sterile barrier film (136) may be sideways inserted into the housing. Subsequently, the cover (8) is engaged with the ribs (169, 178) of the housing unit (2) and moved to close the notch and prevent the sterile barriers from leaving the notch (FIG. 31). During closure of the cover (8) the deformable ribs (181) are plastically deformed to axially or rotationally fixate the cartridge unit (12). The cover (8) may have a locking feature such as a protrusion or flexible arm engaging a counter locking feature on the housing cover or housing base to irreversibly lock the cover (8) to the housing unit.

Figure 32:
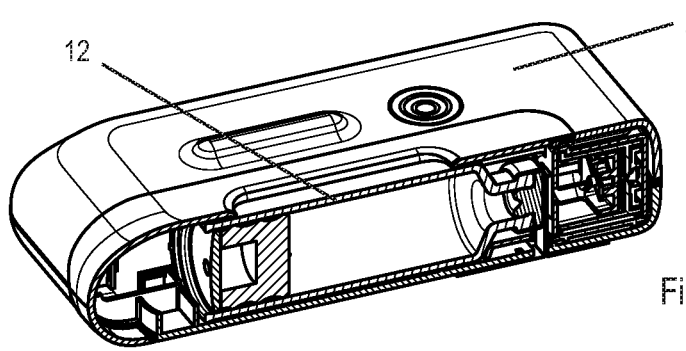
FIG. 32: A cross section of the assembled injection device showing the cartridge unit CU and needle unit NU.
Figure 33:
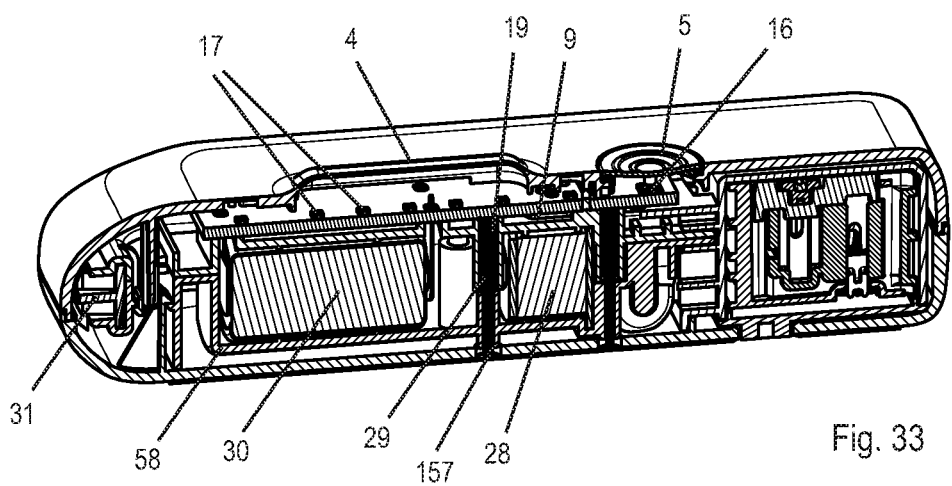
FIG. 33: Cross section of assembled injection device showing battery, electric motor and gear mechanism of the drive unit DU.

The assembled injection device including the cartridge unit (12) is shown in two cross sections taken in a plane through the cartridge unit (FIG. 32) and through the battery/stepper motor (FIG. 33). The cartridge unit (12) is oriented parallel to the bottom surface of the injection device and the septum is aligned with the passage in the needle housing such that the cartridge needle (90) may move through the septum (141). The LED indicators (17) of the PCB unit are located below the indicator section (4) of the housing cover. The lower surface of the PCB unit (9) is contacted with the contacts (157) of the sensor layer in the sensing patch unit (13) via the contact springs (29). The springs (29) are guided through the apertures (32, 56) in the drive unit (10). The battery (30) and the stepper motor (28) are fixated by form fit or an adhesive to the holder (58) of the drive unit (10).

Figure 34:
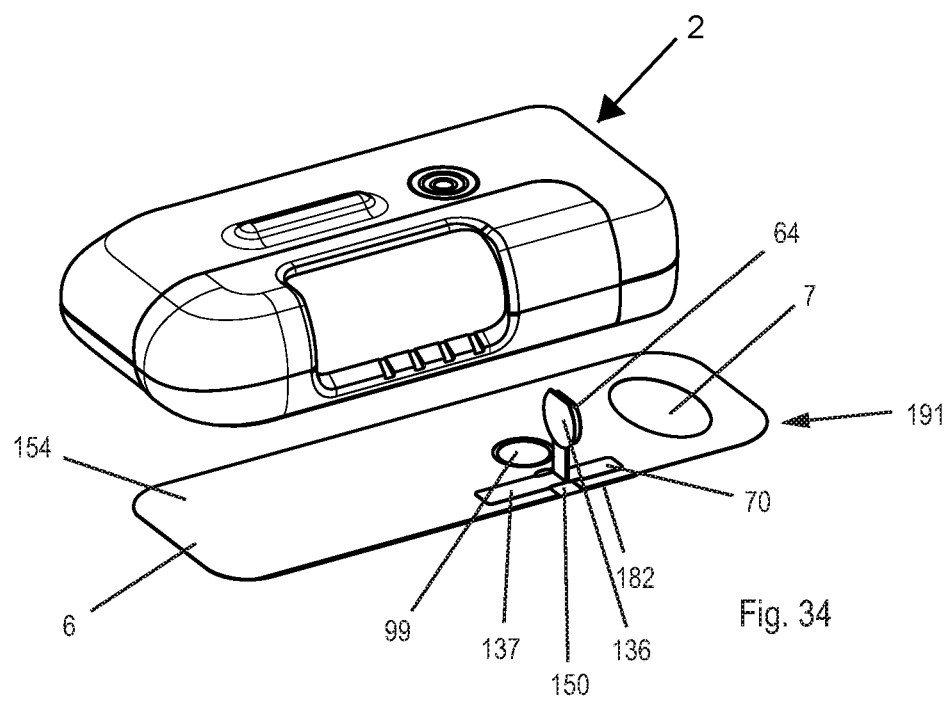
FIG. 34: Release liner removed from the injection device.

The functioning of the injection device will be described in the following. The electronic circuitry of the PCB unit (9) is powered by the battery (30) in the drive unit (10) throughout the lifecycle of the injection device, i.e., there is no separate switch closing the electronic circuit after storage and just prior to using the device. The status of the device is monitored by measuring the signals from the sensor patch unit, such as at a low sampling frequency to save battery power during storage. The user removes the injection device (1) from a packaging and selects a suitable injection location on the body while the release liner (6) is still attached to the skin adhesive layer (191) of the sensing patch unit (13). The user grasps the gripping area (7) of the release liner and peels the release liner (6) from the skin adhesive layer (191) as indicated by the arrow associated with the skin adhesive layer (191) in FIG. 34. As the liner is removed, the sterile barrier film (64) on the needle unit (11) and/or the sterile barrier film (136) on the cartridge unit (12) are peeled-off from the housing (67) of the needle unit (11) and from the crimp cap (139) of the cartridge unit (12), respectively. Both pull tabs (70, 137) may each connected to the exterior surface (165) of the release liner (6) on opposite sides of the notch (150) thereby ensuring that the sterile barrier films (64, 136) are removed one after another, and the forces are directed to different areas on the release liner (6) thereby reducing the risk of liner fracture. The notch (150) in the release liner (6) may be reinforced by a strengthening sheet (182) that is attached to the release liner (6) and covering the notch (150) thereby further reducing the fracture risk. The strengthening sheet (182) may be applied onto the surface of the release liner (6) not contacting the skin adhesive layer (191) and the strengthening sheet may cover one or both ends of the pull tabs (70, 137) for fixating the pull tabs to the release liner in case the pull tabs are not contacted using the adhesive spots (166, 167) (FIG. 25) on the backside of the liner. Alternatively, the strengthening sheet may further enhance the connection between the release liner and the pull tabs (70, 137) if the pull tabs are adhered to the liner using the first and second adhesive spots (166, 167). The strengthening sheet (182) may attach to the barrier film (99) covering the passage (98) in the needle housing such that the release liner removal simultaneously removes the sterile barrier for the skin piercing needle. Thus during release liner removal at least one sterile barrier film is removed either from the needle unit, and/or from the cartridge unit and/or from the passage for the skin piercing needle. Optionally, two strengthening sheets are used, one covering both pull tabs and the other the sterile barrier for the needle housing. As another option three strengthening sheets are used for each pull tab and the sterile barrier for the needle housing.

During release liner removal all three sterile barrier films that cover the passage for the skin piercing needle, the passage for the cartridge needle and the sterile barrier film covering the septum may be removed from the device and both passages of the needle unit and the one passage for the cartridge unit are free.

The release liner (6) and/or the strengthening sheets (182) may be coated with a conductive layer (154) which at least partially shields the sensor areas (161, 162) in the sensor layer (160) of the sensing patch unit (13). Upon removal, the dielectric adjacent and/or between the at least two sensor areas (161, 162) changes as the release liner with the shielding layer is removed and the skin adhesive layer or sensors are exposed (e.g., to the ambient air). The change is measured by the capacitive sensors (161, 162) in the sensor layer (160) and signaled to the PCB unit (9) via the contacting springs (29). In principle the change can be measured with one of the two sensors (161, 162) only. The sampling frequency for the electronic circuit may be low to save energy, and once the change is capacity is processed, the sampling frequency may be increased. Furthermore, the push button switch (16) may be released after the liner removal has been detected by the capacitive sensor. Alternatively, the push button switch (16) is released after attaching the injection device to the skin of the patient. Once attached, the dielectric medium for the sensors (161, 162) in the sensor layer changes again, indicating proper skin attachment of the device. The release liner removal and/or the skin attachment may be notified to the user by the visual LED indicators and/or by audible signals generated by a buzzer, and/or signaled by an external device receiving the information via wireless transmittance.

After the liner removal and the skin attachment, the push button switch (16) of the PCB unit is active and the user may push the button (5) to start the injection sequence. As an alternative, the device does not have a push button (5) and push button switch (16), but starts the injection procedure automatically, such as after a delay time after the sensor patch unit detects that the device is attached to the skin. Safety loops may be included to ensure that the injection is not started too early, for example when the user is still manipulating the device at the injection location. Such a safety loop may require a stable sensor signal for a minimum amount of time before the injection sequence is started automatically. Alternatively, the injection sequence is started based on an audible signal from the user that is detected by a microphone which is connected to the PCB unit. As yet another alternative, the injection device may not have a mechanical push button on the device but a virtual release button is available on a separate device that is wireless connected to the injection device, for example a smart phone. The virtual release button may be pressed on the external device and transmitted to the device which starts the injection sequence.

Figure 35:
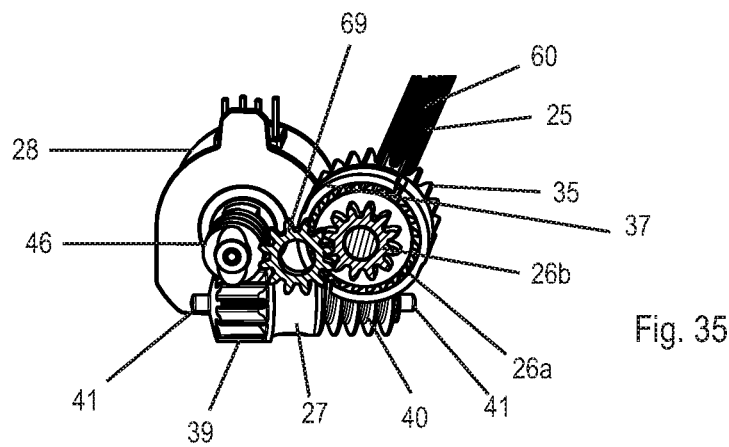
FIG. 35: Detail of the gear mechanism of the injection device.
Figure 36:
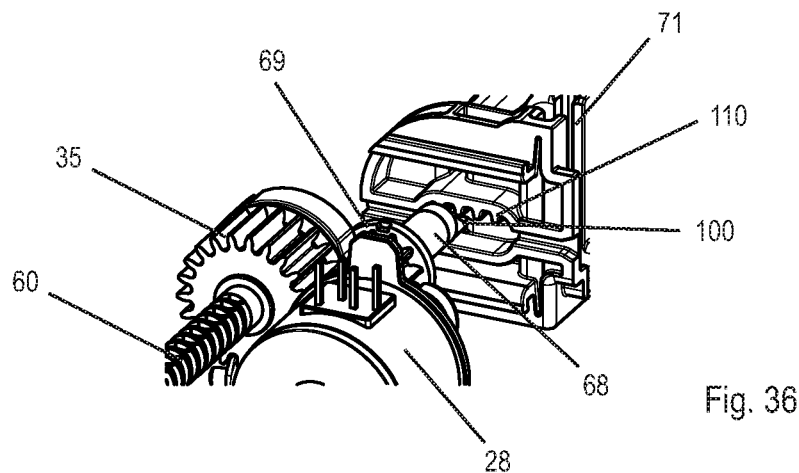
FIG. 36: Detail of the gear mechanism and the electric motor of the drive unit DU engaging the cam shaft and slider of the needle unit NU.
Figure 37A:
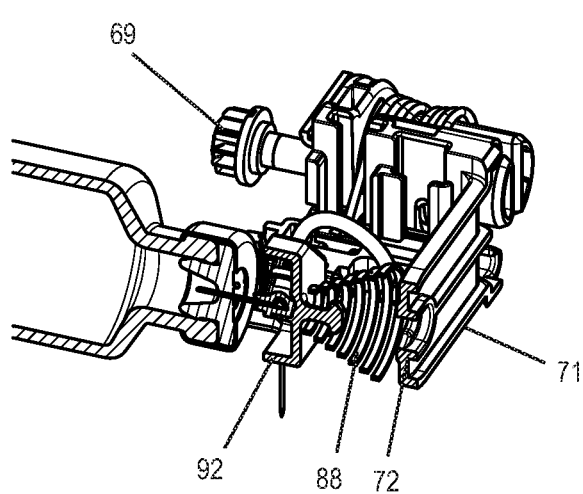
FIGS. 37a, 37b: Cartridge needle slider driven by the cartridge needle slider spring (all needle unit NU) to pierce the septum of the cartridge unit CU.
Figure 37B:
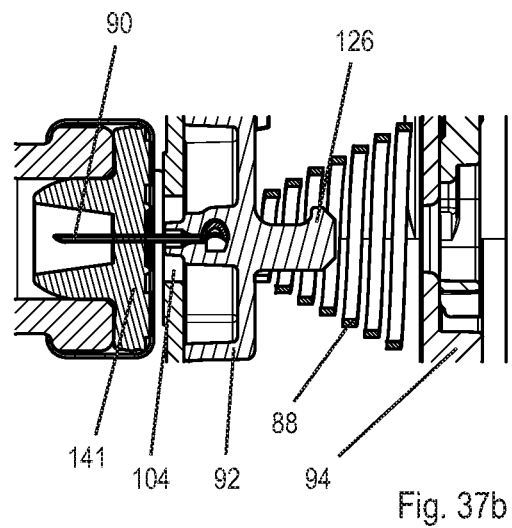

Cartridge needle insertion: When the user pushes the push button, the injection sequence may be started, or the injection sequence may be automatically started if there is no mechanical push button in the device. The stepper motor (28) in the drive unit may be controlled by the PCB unit (9) to rotate in a first rotation direction that may be at a first rotational speed optimized for the needle insertion. The rotation of the stepper motor is transferred by gearing (46, 39, 40, 35) into a rotation of the ratchet wheel (26) as the one-way ratchet (37, 26a) between the driver (34) and the ratchet wheel (26) forces the latter to co-rotate with the driver (34). The cam shaft (68) rotates as well as the drive teeth (26b) of the ratchet wheel (26) engage the gear wheel (69) of the cam shaft (68), see FIG. 35. The rotation of the cam shaft (68) is transferred from the gear wheel (100) of the cam shaft to the gear rack (75) of the slider (71) located in the needle unit. The slider (71) will move from a starting position to a first intermediate position due to the gear teeth (110) of the gear rack (75) engaging the gear wheel (100) of the cam shaft (68), FIG. 36. The slider is guided by the mechanism holder (94) due to the linear guidance formed by the linear keys (73) on the slider and the guidance (105) on the mechanism holder (94). As the slider (71) moves to the first intermediate position, the engagement between the locking fork (72) of the slider and the knob (126) of the cartridge needle slider (92) is released and the cartridge needle slider (92) is moved by the decompressing spring (88) and the cartridge needle (90) pierces the septum (141) of the cartridge unit (FIGS. 37a, 37b). The movement of the assembly of cartridge needle holder (91) and cartridge needle slider (92) may be accompanied by an acoustic signal and/or visual signal (LED light) and/or tactile feedback to the user.

Figure 38:
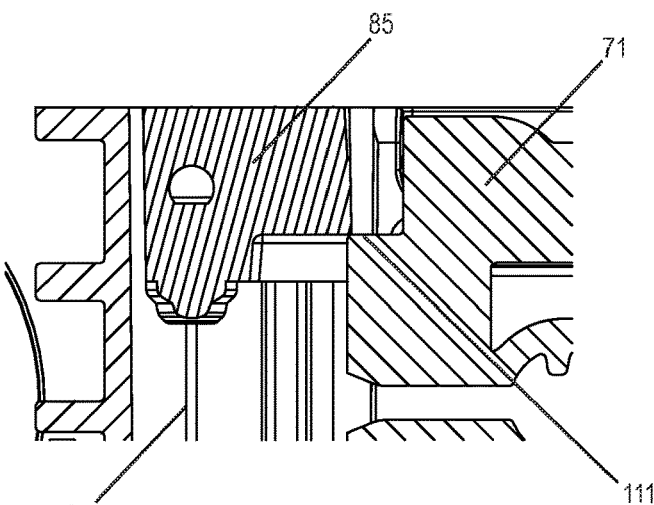
FIG. 38: Skin piercing needle slider abutting the slider for keeping the skin piercing needle in the retracted position.
Figure 39:
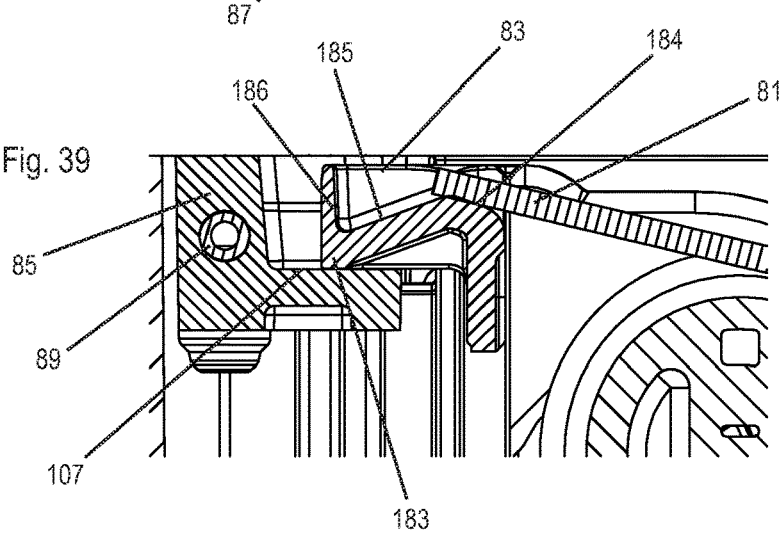
FIG. 39: Upper leg of a torsional spring biasing the skin piercing needle holder towards the inserted position via the upper spring slider
Figure 40:
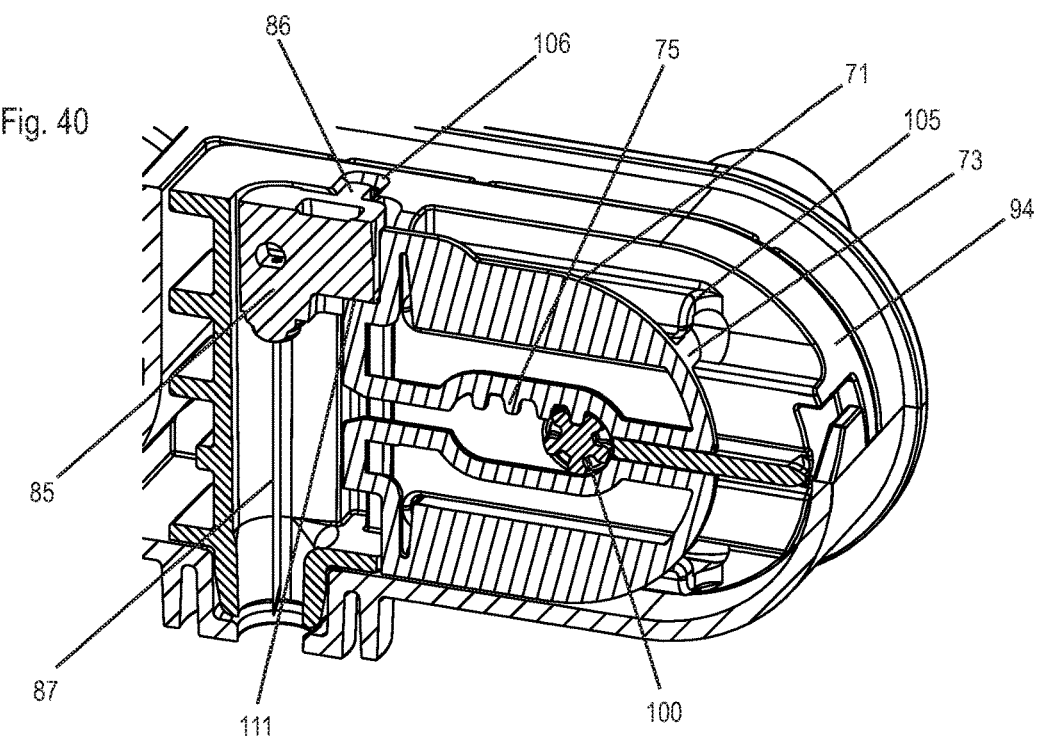
FIG. 40: Cross section of the needle unit with the slider in the starting position.
Figure 41:
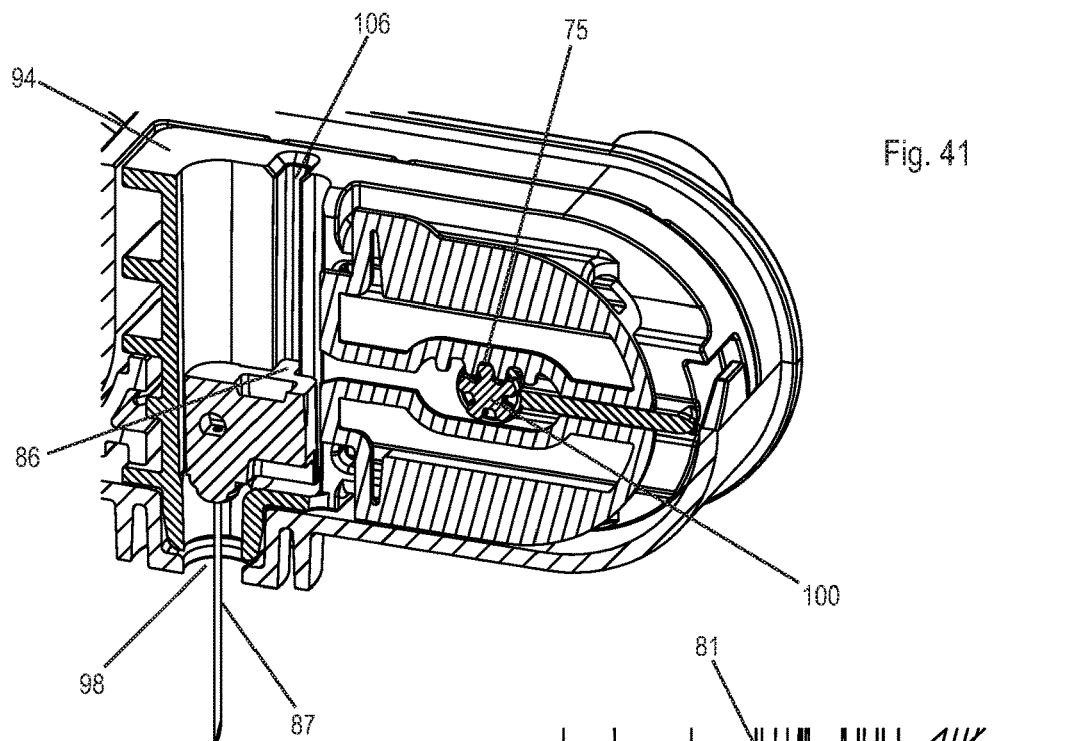
FIG. 41: Cross section of the needle unit with the slider in an intermediate position.
Figure 42:
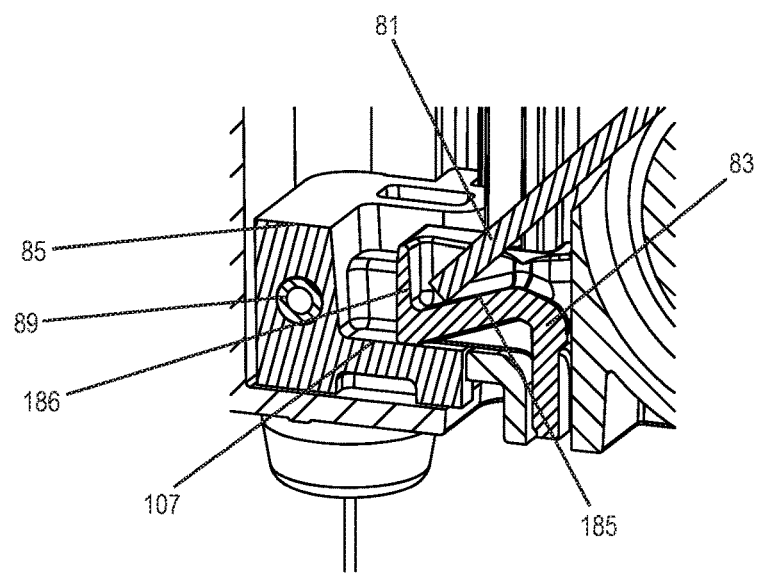
FIG. 42: Leg of the torsional spring has moved the skin piercing needle holder to the inserted position via an upper spring slider.

Skin piercing needle insertion: When the slider (71) is in the starting position (FIGS. 39 and 40), then the stop surface (111) of the slider abuts the skin piercing needle holder (85), (FIG. 40) and keeps the skin piercing needle holder in a needle retracted position against the bias of the upper leg (81) of the torsional spring (79) pushing on the skin piercing needle holder (85) via the upper spring slider (83) and the receiving section (107) of the skin piercing needle holder. The upper leg (81) abuts an abutment surface (184) of the upper spring slider which may be a sloped surface. Upon rotation of the cam shaft, the slider (71) moves towards the first intermediate position (FIG. 41) and the engagement between the slider (71) having stop surface (111) to the skin piercing needle holder is released (see FIG. 38). The skin piercing needle holder (85) will move together with the skin piercing needle (87) towards the inserted position and the tip of the skin piercing needle moves through the aperture (98) in the housing unit as the upper leg (81) of the torsional spring (79) pushes on the upper spring slider (83). The skin piercing needle holder (85) is guided with its keys (86) through guidances (106) of the mechanism holder (94) to insert the needle (87) perpendicular to the bottom surface of the injection device. In FIG. 42, the skin piercing needle holder is in the needle inserted position and the conduit (89) can be observed in the cross sectional view. The cartridge needle has been inserted first in this example followed by the insertion of the skin piercing needle thereby establishing a fluid contact between the patient and the medicament present in the cartridge unit. The situation may also be reversed, e.g., that first the skin piercing needle (87) is inserted followed by the insertion of the cartridge needle (90). The insertion step may also comprise two intermediate positions for the slider (7) a first intermediate position where the cartridge needle is inserted and a second intermediate position where the skin piercing needle is inserted. Alternatively there may be a continuous movement from the starting position to the first intermediate position while to two needles are inserted subsequently.

When the skin piercing needle (87) is in the inserted position then there is an anti-shift back feature for the skin piercing needle holder (85). In the needle inserted position, the end of the upper leg (81) contacts a sloped surface (185) of the upper spring slider (83). When the upper spring slider (83) contacts the skin piercing needle holder (85) via the receiving section (107) then a return movement of the holder will be stopped as the end of the upper leg (81) will abut end surface (186) of the upper spring slider (83). During a return movement, the sloped surface (185) will guide the end of the upper leg into abutment with the end surface (186) of the upper spring slider thereby blocking the upward movement of the skin piercing needle holder (85).

Figure 47:
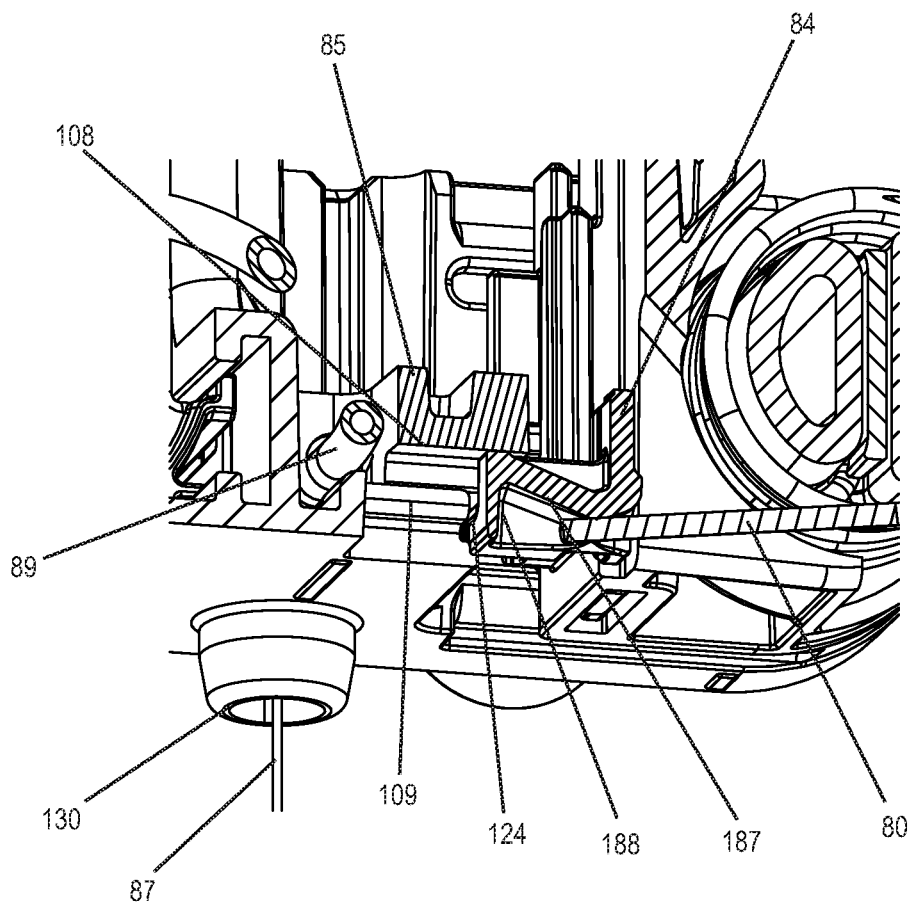
FIG. 47: Lower leg of spring biasing the lower spring slider towards the retracted position, where the locking member prevents movement of the lower spring slider towards the retracted position.

The movement of the skin piercing needle holder (85) in the needle inserted direction is stopped when the skin piercing needle holder (85) abuts a wall or stop surface that is present on the housing of the needle unit. The skin piercing needle holder (85) may engage, for example abut in the inserted position the lower spring slider (84). The lower spring slider (84) may but the receiving section (108) on the skin piercing needle holder (85), see FIG. 47. The lower spring slider (84) is kept in the needle inserted position under the bias of the lower leg (80) of the torsional spring (79) which intends to move the lower spring slider from the inserted position to the retracted position. The lower spring slider (84) is kept in the inserted position (FIG. 47) as the holding surface (124) of the lower spring slider engages the locking member (109) on the mechanism holder. The engagement between the holding surface (124) and the locking member (109) is such that the lower spring slider (84) may axially move together with the slider (71).

During assembly of the device, the upper spring slider (83) is in the needle retracted position and biased by the upper leg (81) towards the needle inserted position and this movement is blocked by the skin piercing needle holder (85) engaging the slider (71). When the upper spring slider is in the needle retracted position, then the lower spring slider (84) is in the needle inserted position and not in abutment with the skin piercing needle holder (85) yet. The lower spring needle slider (84) is kept in the inserted position due the engagement (109, 124) of the slider with the mechanism holder (94).

Figure 43:
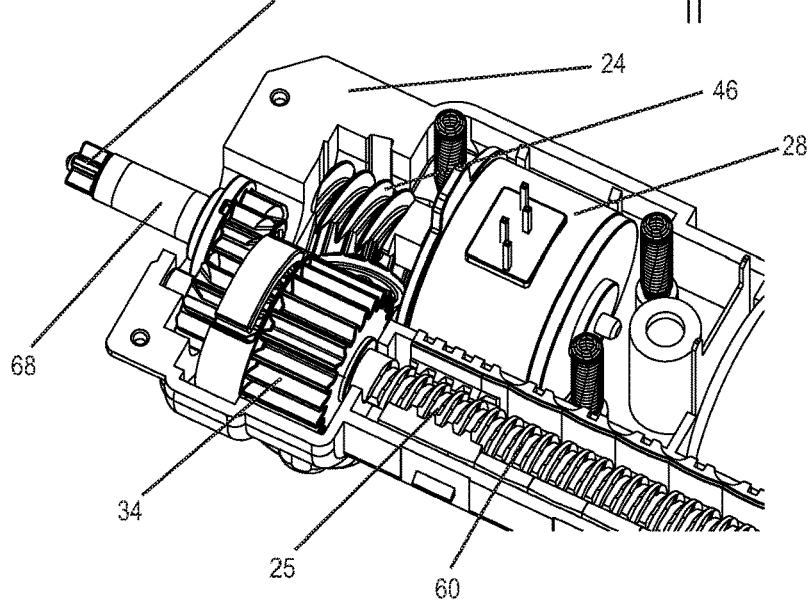
FIG. 43: Gear mechanism driving the threaded rod for piston rod advancement.

Dose delivery: The slider (71) is moved to an intermediate position for needle insertion and that position is defined by the number of revolutions (or steps) of the stepper motor in the first rotation direction and therewith the number of revolutions of the cam shaft (68) for sliding the slider (71). After a certain number of revolutions in one rotation direction the rotation in that direction is stopped. Alternatively a separate sensor that is not shown measures the position of the slider and forwards the information to the PCB unit. After the insertion of both needles, the rotation direction of the stepper motor (28) is reversed. The threaded rod (25) comprising the driver (34) will be rotated in the opposite direction and the rotation of the driver (34) is not transmitted to the ratchet wheel (25) as the torque that is transmitted from the ratchet arms (37) of the driver (34) to the asymmetric ratchet teeth (26a) of the ratchet wheel (26) is below the friction between of the cam-shaft (68) and the housing as, for example, generated by the O-ring (102a). Alternatively, there may be a tight press-fit between the cam shaft and the housing forming a sterile barrier. The ratchet wheel (26) will not rotate and the ratchet member (37) at the end of the flexible arms (38) will ratchet over the ratchet teeth (26a) of the ratchet wheel thereby generating audible clicks during dose delivery (FIG. 43).

The rotation of the driver (34) will rotate the threaded rod (25) and the piston rod (31) will advance due to the threaded engagement (54, 60) between the threaded rod (25) and the first segment (53) of the piston rod (31). The segmented piston rod is prevented from rotation around its own axis and will slide through the guidances (59) during advancement thereby going through a U-shaped configuration. The last segment of the piston rod (49) either abuts the plunger (140) in the cartridge or abuts the spacer (142) abutting the plunger to expel medication through the cartridge needle, the conduit and the skin piercing needle into the patient. The driver (34) is permanently rotationally coupled to the threaded rod (25) independent from the rotation direction that is transmitted from the stepper motor via the gear mechanism. This implies that during the needle insertion step the segmented piston rod may retract as the slider is moved from the first position to the intermediate position. The spacer may comprise a resilient element for keeping the pivot bearing between the last segment and the spacer in engagement during the piston rod retraction.

Figure 44:
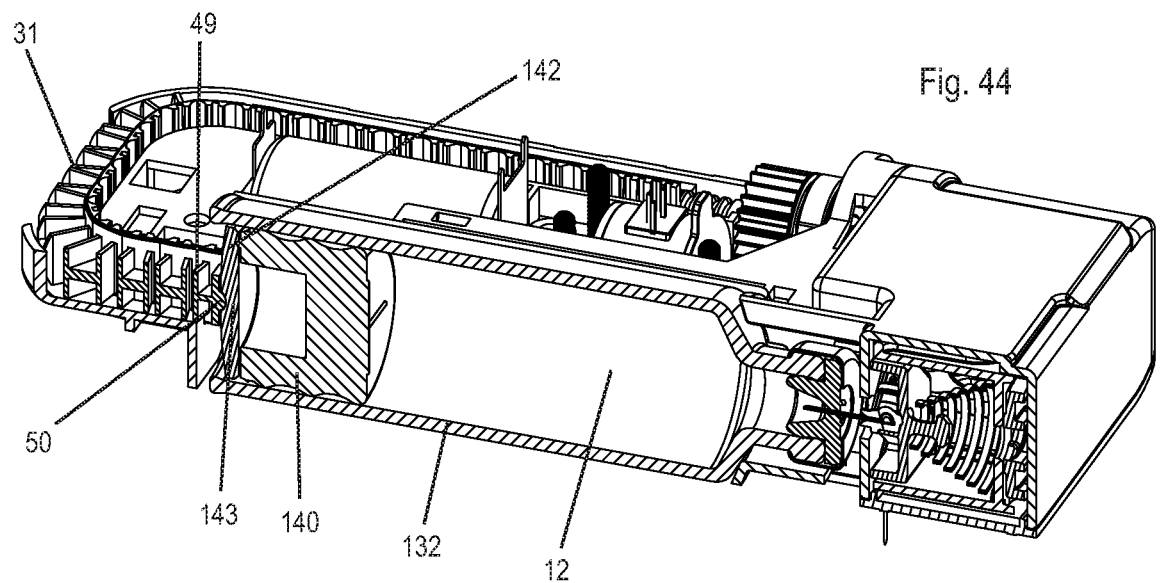
FIG. 44: Drive unit and needle unit, with piston rod in a retracted position, and with a full cartridge.
Figure 45:
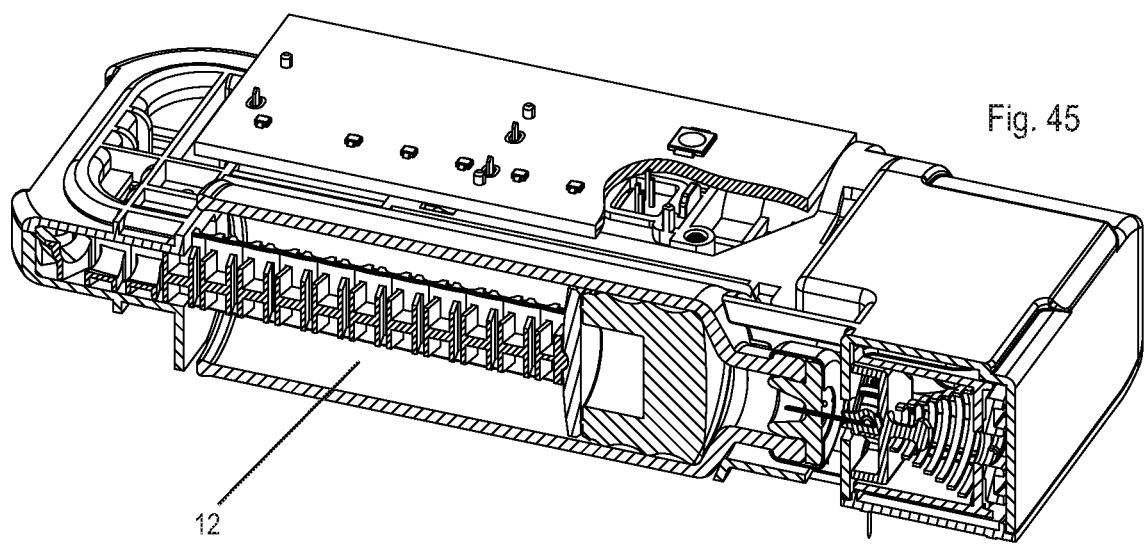
FIG. 45: Drive unit and needle unit, with piston rod in an extended position, and cartridge empty.

The piston rod advancement is shown in FIGS. 44 and 45, where the piston rod (31) advances the plunger (140) in the barrel (132) of the cartridge unit (12). The last segment (49) of the piston rod comprises the protrusion (50) that engages a bearing surface (143) of the spacer (142). The pivot bearing that is established may be a ball-in-a-socket, or a ball-on-plate bearing ensuring that any off-axis loading by the piston rod entering the cartridge is compensated and that the plunger is not subjected to any tilting moment. When the plunger (140) has reached the end of the barrel and enters the neck section (FIG. 45) then the piston rod advancement is stopped. As an alternative and not desired option, the plunger may stop in a position that is between the positions shown in FIGS. 44 and 45, due to an occlusion in the fluid path preventing further advancement of the plunger. The PCB unit may have several options for detecting that the cartridge has been emptied or that there is an occlusion. The electric motor may have an encoder measuring the rotation or steps of the electric motor and a separate sensor (for example a photo sensor, or a sliding contact) following the rotation of the gear mechanism and a control module in the PCB unit measures any differences in rotation between the two for detecting an empty cartridge or an occlusion. This set-up requires separate sensor units. Alternatively, the current is measured to energize the electric motor and used as a signal for the load delivered by the motor. The current signal needs to be processed by the control module for detecting a blocking of the piston rod advancement, which requires additional features in the PCB unit. In another arrangement, the Back Electro Motive Force (BEMF) is measured where the electric motor is operated as a generator for a limited period of time during a cycle and the resultant voltage is measured before the electric motor is switched back to motor operation. This option has the advantage that it does not require any additional components. Finally, the extra load on the electric motor due to blockage of the piston rod advancement can be measured as a phase shift or step-loss due to an axial displacement of the rotor versus the stator in the electric motor and this may be used for detecting an empty cartridge or an occlusion.

The control system in the PCB unit may activate optical (LED) or acoustic (buzzer) or tactile (vibrating signals to the user when the cartridge has been emptied or when the there is an occlusion in the fluid path preventing further piston rod advancement.

Figure 46:
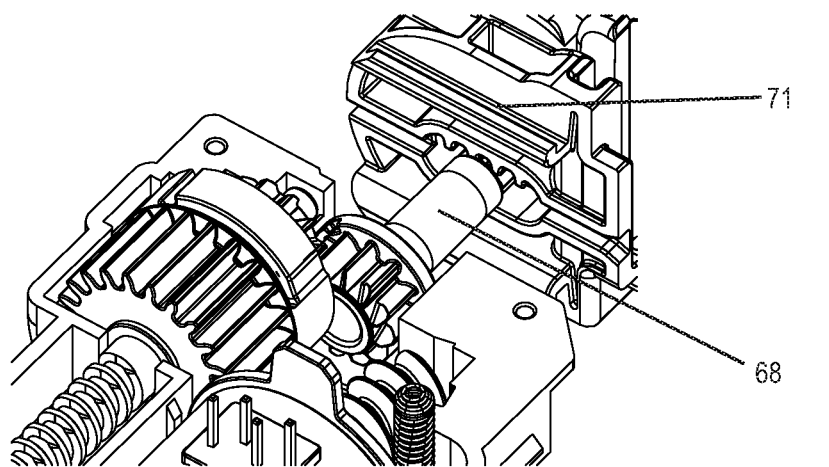
FIG. 46: Gear mechanism and slider in an intermediate position.
Figure 48:
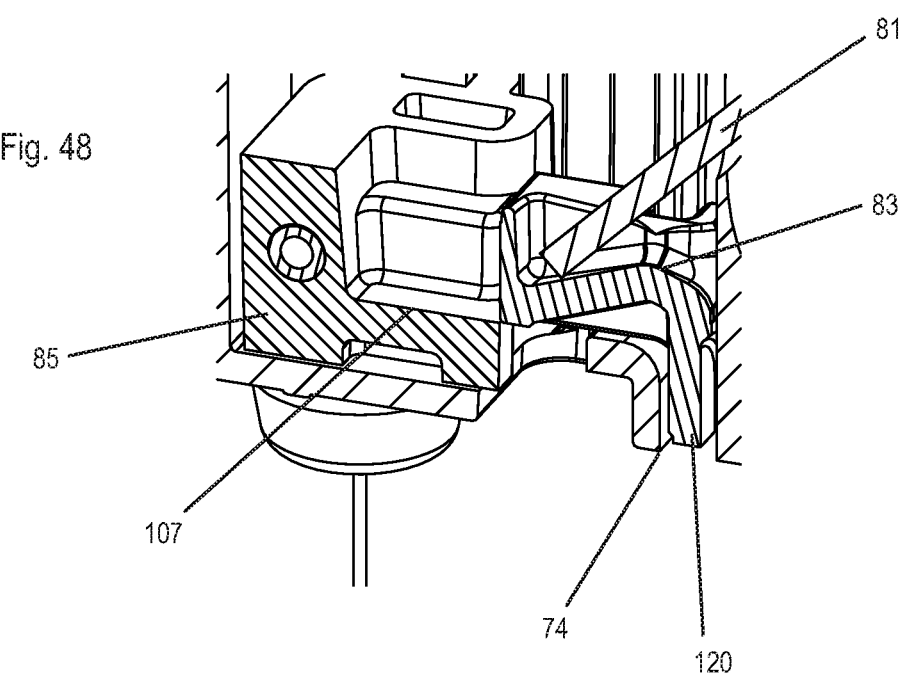
FIG. 48: Upper spring slider released from the skin piercing needle holder.
Figure 49:
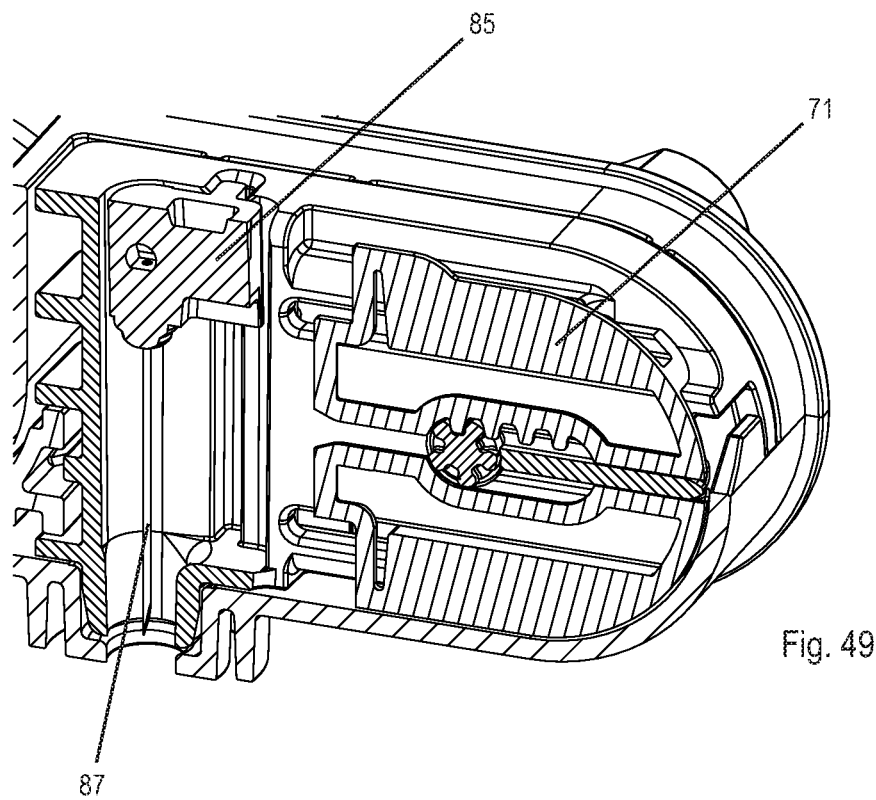
FIG. 49: Cross section of the needle unit with the slider in a final position and the skin piercing needle holder in a retracted position.
Figure 50:
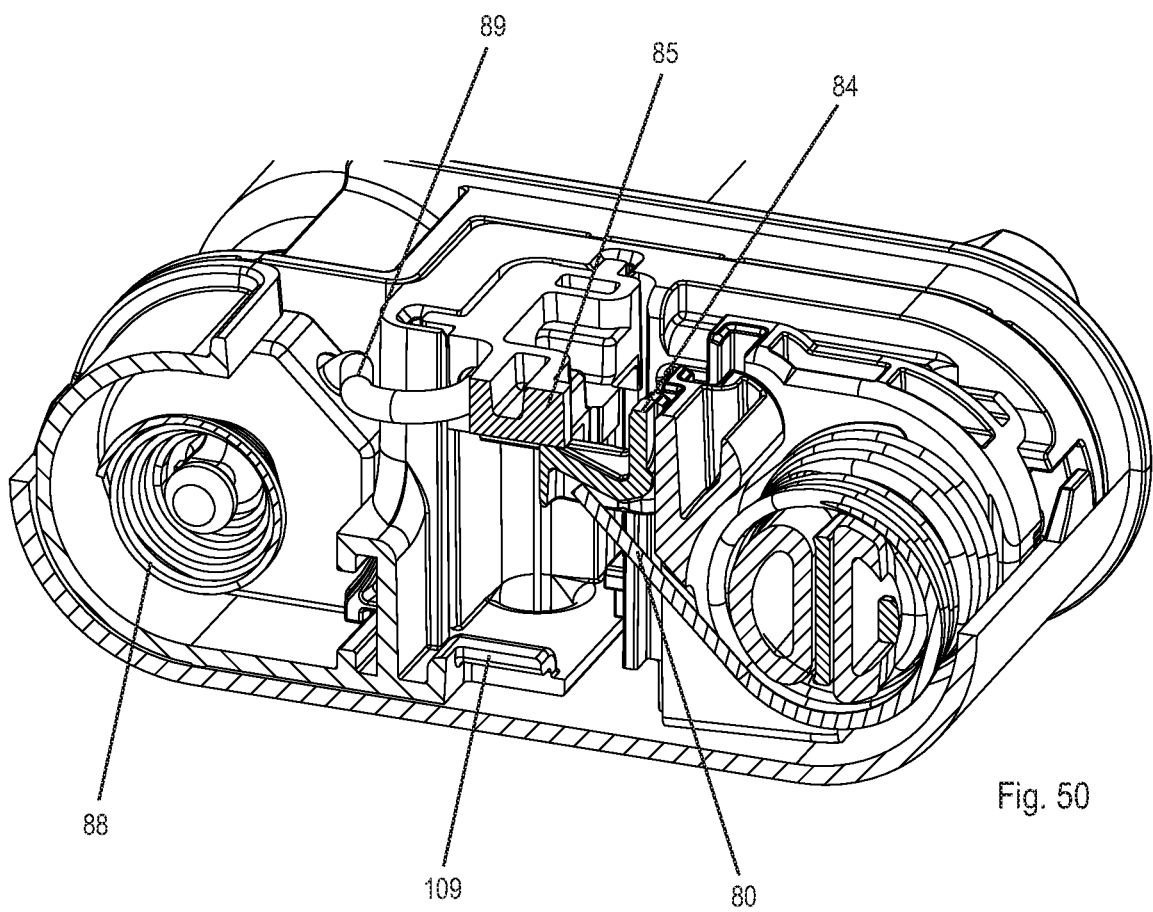
FIG. 50: Cross section of the injection device with a retracted needle.

Retraction of the skin piercing needle: When the plunger has advanced to the end of the cartridge, a signal from a sensor, an encoder or the electric motor is received signaling blockage of the piston rod. The PCB unit controlling the electric motor will reverse the rotation direction from the second rotation (for delivery) back to the first rotation direction that was also used for the needle insertion step. The gear mechanism will rotate the driver (34) and the ratchet wheel (26) as the one way ratchet system is rotationally locked. As a result, the slider (71) will move from the first intermediate position to a next position (FIG. 46). The next position may be the final position or a subsequent intermediate position before moving to the final position. The slider may move from a first intermediate position without any additional stops to the final position. The movement of the slider (71) results in a lateral movement of the upper spring slider (83) and the lower spring slider (84) as the two spring sliders are engaged via the linear guidances (74) to the slider (71), see FIG. 8*i*. The skin piercing needle holder (85) is engaged with the mechanism holder (94) resulting in a relative axial movement between the upper and lower spring sliders (83,84) and the skin piercing needle holder (85) as the slider (71) moves towards the final position. The engagement between the upper spring slider (83) and the engagement section (107) of the skin piercing needle holder (85) may be released first (FIG. 48). The biasing force of the upper leg (81) may move the upper spring slider in a final position, for example in abutment with the mechanism holder and simultaneously the skin piercing needle holder (85) is free to move back into the retracted position. In a subsequent step, while the slider is moving towards the final position, the engagement between the lower spring slider (84) and the mechanism holder (109, 84) is released and the lower spring slider (84) moves towards the retracted position as the slider is guided by linear guidances (74) of the slider due to the torque that is released from the torsional spring and applied to the lower spring slider via the lower leg (80). The lower spring slider (84) engages receiving section (108) of the skin piercing needle holder and therefore the skin piercing needle holder (85) including the needle (87) is moved back to the retracted position as the skin piercing needle holder is guided in the mechanism holder (FIG. 49, FIG. 50). The lower spring slider has an end surface preventing movement back to the inserted position as the end of the lower leg (80) will abut the end surface of the lower spring slider. This mechanism equals the mechanism for preventing the movement the skin piercing needle holder from the inserted to the retracted position using end surface (188) for the upper spring slider, see above.

As an alternative, first the lower spring slider is released from the mechanism holder followed by the release of the upper spring slider from the skin piercing needle holder.

As the slider (71) has reached the final position (FIG. 49), the sensor system described above will signal blocking of the gearing mechanism and this signal may be used by the PCB unit to provide and acoustic, visual or tactile signal to the user that the skin piercing needle has been retracted. The PCB unit may apply a holding time, for example 60 seconds, 30 seconds, or between 5 and 10 seconds during (or after) which a signal is provided to the user before the user may remove the device from the skin. The holding time may enhance the diffusion of the medicament into the (subcutaneous) tissue before removing the device from the skin. The end of injection signal may be directly sent to the user by the device and/or may be sent via a wireless connection (such as Bluetooth) to an external device which provides the end of injection signal.

The signals provided by the sensors and/or the electric motor related to the needle insertion, piston rod advancement to the final position, occlusion in the fluid path unit or needle retraction may be used for the visual, tactile or audible signaling directly to the user. Optionally, the signals are sent to an external device, for example a smart phone and the smart phone provides for the visual, tactile or audible signals. Thus there may be a system were the injection device provides signals to the user, or that one of the device or the external device (smart phone) provides for the signals. The PCB unit may signal an alarm to the user upon malfunctioning of the device such as the occurrence of partial removal of the device as measured by the sensor unit, an occlusion in the fluid path, motor failure, low battery power, failure of the push button switch, failure to insert the cartridge needle into the cartridge unit, failure to insert the skin piercing needle or failure to retract the skin piercing needle. Such a signal may be followed by additional steps in the injection sequence, for example when the sensors in the sensor layer of the sensor patch unit measure partial removal of the device or when an occlusion occurs, then the processor may activate the needle retraction step (by reversing the rotation direction of the motor) before the cartridge has been emptied.

Signals may also be received from an external device to the PCB unit via a wireless communication such that the start of the injection may be triggered by an external device.

The PCB unit may be configured to receive vocal instructions from the user, for example using a voice recognition tool. Alternatively, the PCB unit may provide vocal instructions using a speaker for giving instructions to the user.

The injection device may be used in combination with a wide variety of medicaments each having a specific dosing volume and/or viscosity of the liquid and which require a certain injection time. The injection device may be configured to receive glass cartridges with a nominal volume between 2 mL and 10 mL. Smaller cartridges may use the cartridge holder that is configured for the larger cartridges using a volume adapter that compensates for the space between the smaller cartridge and the cartridge holder. The injection time may be less than 30 minutes, less than 10 minutes or less than 1 minute. The gear ratios of the gearing mechanism between the electric motor and the cam shaft may be adapted to accommodate different viscosities of the medicament in the cartridge unit and/or different needle gauges for the skin piercing needle, respectively the cartridge needle used which may increase the force required to advance the piston rod.

In the claims, the word "comprising" does not exclude other elements or steps, and the indefinite article "a" or "an" does not exclude a plurality. For example "a film" does not exclude the fact that there may be two films that functionally or structurally fulfill the purpose of "a film". The mere fact that certain elements or steps are recited in distinct claims shall not preclude the existence of further meaningful combinations of these elements or steps.

| PART ANNOTATION | | | |
|---|---|---|---|
| 1 | Injection device | 25 | Threaded rod TR |
| 2 | Housing unit HU | 26 | Ratchet wheel RW |
| 3 | Viewing window cover | 26a | Ratchet teeth ratchet wheel |
| 4 | Indicator | 26b | Drive teeth ratchet wheel |
| 5 | Push button | 27 | Gear shaft GS |
| 6 | Release liner sensing patch unit | 28 | Stepper motor SR |
| 7 | Gripping area | 29 | Contact springs CS |
| 8 | Cover HU | 30 | Battery BY |
| 9 | Printed circuit board unit PCB | 31 | Piston rod PR |
| 10 | Drive unit DU | 32 | Cylindrical aperture |
| 11 | Needle unit NU | 33 | Snapper |
| 12 | Cartridge unit CU | 34 | Threaded rod driver |
| 13 | Sensing patch unit SU | 35 | Gear teeth threaded rod driver |
| 14 | Top surface PCB | 36 | Shaft end |
| 15 | Bottom surface PCB | 37 | Ratchet member |
| 16 | Push button switch | 38 | Flexible arm |
| 17 | LED indicators | 39 | Gear wheel gear shaft |
| 18 | Positioning apertures PCB | 40 | Worm wheel gear shaft |
| 19 | Contacts for contact springs | 41 | Shaft ends |
| 20 | Contacts to stepper motor | 42 | Motor |
| 21 | Contacts to battery | 43 | Edge end plate |
| 22 | Protrusions drive unit | 44 | End plate |
| 23 | Drive cover DC | 45 | Contacts |
| 24 | Drive carrier DR | 46 | Worm wheel stepper motor |
| 47 | Handle end plate | 83 | Upper spring slider |
| 48 | Segment piston rod | 84 | Lower spring slider |
| 49 | Last segment piston rod | 85 | Skin piercing needle holder |
| 50 | Protrusion last segment | 86 | Linear keys |
| 51 | Guiding fin | 87 | Skin piercing needle |
| 52 | Hinge piston rod | 88 | Tapered cartridge needle slider spring |
| 53 | First segment piston rod | | |
| 54 | Internal threading | 89 | Tube, conduit |
| 55 | Segment guidance | 90 | Cartridge needle |
| 56 | Cylindrical aperture drive carrier | 91 | Cartridge needle holder |
| 57 | Protrusion, snapper | 92 | Cartridge needle slider CNS |
| 58 | Holder for battery, motor | 93 | Guidance |
| 59 | Guidance piston rod | 94 | Mechanism holder |
| 59a | Key way | 95 | Key ways to guidance CNS |
| 60 | Outside threading piston rod | 96 | Needle cover |
| 61 | Cartridge holder | 97 | Sealing rim |
| 62 | Abutment surface | 98 | Aperture skin piercing needle |
| 63 | Receiving section | 99 | Barrier film |
| 64 | Sterile barrier needle unit | 100 | Gear wheel CT for gear rack |
| 65 | Key | 101 | Fluid path compartment |
| 66 | Locking aperture | 102 | Passage cam shaft |
| 67 | Housing needle unit | 102a | O-ring cam shaft |
| 68 | Cam shaft | 102b | Passage cam shaft |
| 69 | Gear wheel cam shaft | 103 | Slider compartment |
| 70 | Pull tab | 104 | Passage fluid path compartment |
| 71 | Slider | | |
| 72 | Locking fork slider | 105 | Guidance mechanism holder to slider |
| 73 | Linear keys slider | | |
| 74 | Linear guidances to spring slider | 106 | Guidance mechanism holder to skin piercing needle holder |
| 75 | Gear rack slider | | |
| 76 | Spring fixator | 107 | Receiving section upper spring |
| 77 | Aperture slider | | |
| 78 | Wing | 108 | Receiving section for lower spring slider on skin piercing needle holder |
| 79 | Torsional spring | | |
| 80 | Lower leg | | |
| 81 | Upper leg | | |
| 82 | Coil | | |

-continued

| PART ANNOTATION | | | |
|---|---|---|---|
| 109 | Locking member for lower spring slider on mechanic holder | 142 | Spacer |
| | | 143 | Bearing surface |
| | | 144 | External fold |
| 110 | Teeth gear rack | 145 | Internal fold |
| 111 | Stop surface to SNH | 146 | Connector |
| 112 | Spring holder | 147 | Predetermined breaking point |
| 113 | Receiving pocket | 148 | End surface |
| 114 | End section | 149 | Aperture for cartridge needle |
| 115 | Cut out | 150 | Notch release liner |
| 116 | Base slider | 151 | Legs U-shaped notch |
| 117 | Bridging bar | 152 | Opening notch |
| 118 | Abutment surface slider | 153 | Aperture RL skin piercing needle |
| 119 | Flexible arm spring holder | 154 | Conductive layer |
| 120 | Key upper spring slider | 155 | Notch sensing patch unit |
| 121 | Key lower spring slider | 156 | Aperture sensing patch unit |
| 122 | Receiving section | 157 | Contact points |
| 123 | Opening for upper leg | 158 | Assembly |
| 124 | Holding surface lower spring slider | 159 | Adhesive top layer to HU |
| | | 160 | Sensor layer |
| 125 | Locking feature | 161 | Sensor area |
| 126 | Knob | 162 | Second sensor area |
| 127 | Aperture MH | 163 | Lead |
| 128 | Sealing surface | 164 | Contact |
| 129 | Circumferential rim | 165 | Backside surface release liner |
| 130 | Aperture skin piercing needle in MH | 166 | Adhesive spot |
| | | 167 | Second adhesive spot |
| 131 | Notch needle housing for sterile barrier film | 168 | Housing cover HC |
| | | 169 | Guiding rib |
| 132 | Barrel | 170 | Closure rim |
| 133 | Distal opening | 171 | Housing base HB |
| 134 | Proximal opening | 172 | Closing rim |
| 135 | Neck | 173 | Aperture skin piercing needle |
| 136 | Sterile barrier film | 174 | Notch housing base |
| 137 | Pull tab | 175 | Support flange, snapper |
| 138 | Flip off cap | 176 | Marks |
| 139 | Crimp | 177 | Aperture HC push button |
| 140 | Plunger | 178 | Guiding rib |
| 141 | Septum | 187 | Sloped surface lower slider |
| 179 | Rib engager HC | 188 | End surface lower slider |
| 180 | Rib engager HB | 189 | Connector |
| 181 | Deformable ribs, arresters | 190 | Lock protrusion |
| 182 | Strengthening sheet | 191 | Skin adhesive layer |
| 183 | Contact surface spring slider to receiving section | 192 | Opening housing cover |
| | | 46, 39, 40, 35 | Gearing mechanism |
| 184 | Contact surface spring to slider | 37, 26a | One-way ratchet |
| 185 | Sloped surface upper slider | | |
| 186 | End surface upper slider | | |

What is claimed is:

1. An injection device configured for attachment to skin of a patient, comprising
a housing;
a skin adhesive layer coupled to an outside surface of the housing configured for attaching the injection device to the skin of the patient,
a release liner covering the skin adhesive layer thereby preventing skin attachment of the injection device,
a first film comprising a first end and a second end, wherein the first end is coupled to an internal surface of the housing and forms a removable sterile barrier, and wherein the second end is coupled to an exterior surface of the release liner without contacting the skin adhesive layer,
wherein each of the housing, the skin adhesive layer and the release liner comprises a notch or an aperture, wherein the notches or apertures define a passage extending between an interior of the housing to an exterior of the housing, and wherein the second end of the first film extends through the passage to the exterior of the housing, and
wherein at least one of the notches or the apertures comprises a U-shaped aperture defining a notch opening configured to receive the first film.

2. The injection device according to claim 1, further comprising a second film, the second film comprising a first end and a second end, wherein the first end is coupled to another internal surface of the housing and forms a removable sterile barrier, and wherein the second end is coupled to the exterior surface of the release liner without contacting the skin adhesive layer.

3. The injection device according to claim 2, wherein one of the second ends of the first film or the second film is coupled to the release liner adjacent to one leg of the U-shaped aperture, and the other of the second ends of the first film or the second film is connected to the release liner adjacent to another leg of the U-shaped aperture.

4. The injection device according to claim 2, wherein at least one of first film or the second film is configured as a monolithic film, or wherein at least one of first film or the second film comprises a pull tab, wherein the pull tab is arranged at the second end of the at least one of the first film or second film and coupled to the exterior surface of the release liner.

5. The injection device according to claim 2, wherein a portion of the second film forming the removable sterile barrier is coupled to an end of a cartridge closed by a pierceable septum, wherein the removable sterile barrier covers a surface of the pierceable septum to maintain sterility of the surface of the septum, and wherein the cartridge is located within the housing.

6. The injection device according to claim 5, wherein the portion of the second film forming the removable sterile barrier is coupled to an end surface of a crimp of the cartridge, wherein the crimp holds the septum to the cartridge.

7. The injection device according to claim 5, wherein a cartridge needle within the housing is configured to be moved through a passage of a fluid path compartment into a pierceable septum of the cartridge upon removal of the first end of the first film forming the removable sterile barrier and the first end of the second film forming the removable sterile barrier connected to the end of the cartridge.

8. The injection device according to claim 1, wherein the notch opening is closed by a cover of the housing.

9. The injection device according to claim 8, wherein the cover is a separate component of the housing and is configured to be splined to the housing such that the cover can be guided when closing the housing and notch opening upon receipt of the first film.

10. The injection device according to claim 1, wherein the notch or the aperture in the housing comprises rounded edges.

11. The injection device according to claim 1, wherein a portion of the first film forming the removable sterile barrier is coupled to a surface of a passage of a fluid path compartment within the interior of the housing and covers the passage to maintain sterility within the fluid path compartment.

12. The injection device according to claim 11, wherein the fluid path compartment comprises a cartridge needle configured to be moved through the passage.

13. The injection device according to claim 12, wherein the cartridge needle is configured to be moved through the passage of the fluid path compartment into a pierceable septum of a cartridge upon removal of the first end of the first film forming the removable sterile barrier.

14. The injection device according to claim 1, wherein the release liner is covered by a strengthening sheet adhesively coupled to the exterior surface of the release liner and covers the notch or the aperture in the release liner and the other end of the first film.

15. The injection device according to claim 14, wherein the release liner further comprises another aperture for a skin piercing needle, wherein an end of the skin piercing needle is configured to be moved from a first position in the interior of the housing to a second position at the exterior of the housing, and wherein the another aperture is covered by a second film comprising a removable sterile barrier that is adhesively coupled to the strengthening sheet.

16. The injection device according to claim 15, wherein the skin piercing needle is enclosed by a fluid path compartment within the interior of the housing and coupled to a cartridge needle by a conduit.

17. An injection device configured for attachment to skin of a patient, comprising
a housing;
a skin adhesive layer coupled to an outside surface of the housing configured for attaching the injection device to the skin of the patient;
a release liner covering the skin adhesive layer thereby preventing skin attachment of the injection device;
a first film comprising a first end and a second end, wherein the first end is coupled to an internal surface of the housing and forms a removable sterile barrier, and wherein the second end is coupled to an exterior surface of the release liner without contacting the skin adhesive layer;
a second film comprising a first end and a second end, wherein the first end is coupled to another internal surface of the housing and forms a removable sterile barrier, and wherein the second end is coupled to the exterior surface of the release liner without contacting the skin adhesive layer;
wherein each of the housing, the skin adhesive layer and the release liner comprises a notch or an aperture, wherein the notches or the apertures define a passage extending between an interior of the housing to an exterior of the housing, and wherein the second end of each of the first film and the second film extends through the passage to the exterior of the housing, and wherein at least one of the notches or the apertures comprises a U-shaped aperture defining a notch opening configured to receive the first film.

18. The injection device according to claim 17, wherein the removable sterile barrier of the first film covers a surface of a passage of a fluid path compartment within the housing to maintain sterility of the fluid path compartment, and the removable sterile barrier of the second film covers a surface of a pierceable septum of a cartridge within the housing to maintain sterility of the surface, and
wherein a cartridge needle within the housing is configured to be moved through the passage of the fluid path compartment into the pierceable septum of a cartridge upon removal of both the first end of the first film forming the removable sterile barrier and the first end of the second film forming the removable sterile barrier.

19. The injection device according to claim 18, further comprising a skin piercing needle enclosed by the fluid path compartment,
wherein the skin piercing needle is configured to be moved from a first position in the interior of the housing to a second position at the exterior of the housing through another aperture,
wherein the another aperture is covered by a third film comprising a removable sterile barrier, and
wherein removal of the release liner causes the first, second and third films to be removed.

* * * * *